United States Patent
Marziali et al.

(10) Patent No.: US 9,512,477 B2
(45) Date of Patent: Dec. 6, 2016

(54) BIOMARKER ANAYLSIS USING SCODAPHORESIS

(71) Applicants: Boreal Genomics Corp., Mountain View, CA (US); The University of British Columbia, Vancouver (CA)

(72) Inventors: Andrea Marziali, North Vancouver (CA); Matthew Wiggin, Vancouver (CA); Gosuke Shibahara, Vancouver (CA); Valentina S. Vysotskaia, Belmont, CA (US)

(73) Assignees: Boreal Genomics Inc., Vancouver, British Columbia; The University of British Columbia, Vancouver, British Columbia (*) Notice: Subject to any disclaimer, the term of this patent is extended or adjusted under 35 U.S.C. 154(b) by 252 days.

(21) Appl. No.: 13/887,060

(22) Filed: May 3, 2013

(65) Prior Publication Data

US 2013/0296176 A1 Nov. 7, 2013

Related U.S. Application Data

(60) Provisional application No. 61/643,144, filed on May 4, 2012.

(51) Int. Cl.
*C12Q 1/68* (2006.01)
*C07H 21/02* (2006.01)

(52) U.S. Cl.
CPC .......... *C12Q 1/6869* (2013.01); *C12Q 1/6806* (2013.01); *C12Q 1/6816* (2013.01)

(58) Field of Classification Search
CPC ............ C12Q 1/6816; C12Q 2565/607; C12Q 1/6869
See application file for complete search history.

(56) References Cited

U.S. PATENT DOCUMENTS

| | | | |
|---|---|---|---|
| 4,148,703 A | 4/1979 | Trop et al. |
| 4,390,403 A | 6/1983 | Batchelder |
| 4,390,404 A | 6/1983 | Esho et al. |
| 4,732,656 A | 3/1988 | Hurd |
| 4,911,817 A | 3/1990 | Kindlmann |
| 4,971,671 A | 11/1990 | Slater et al. |

(Continued)

FOREIGN PATENT DOCUMENTS

| | | | |
|---|---|---|---|
| CA | 2552262 A1 | 8/2005 |
| CA | 2523089 A1 | 4/2006 |

(Continued)

OTHER PUBLICATIONS

Jorgez, C. J. et al., Fetal Diagn. Ther., vol. 25, pp. 314-319 (2009).*

(Continued)

*Primary Examiner* — Teresa Strzelecka
(74) *Attorney, Agent, or Firm* — Brown Rudnick LLP

(57) ABSTRACT

The invention discloses methods and apparatus for characterizing trace nucleic acids that are biomarkers for disease. The methods and apparatus provide increased sensitivity to such trace nucleic acids, and allow analysis of nucleic acids present in a sample at only 0.01% of the wild-type sequences. The methods and apparatus are also designed for straightforward multiplexing, thus allowing pooling of clinical samples.

21 Claims, 19 Drawing Sheets

(56) References Cited

U.S. PATENT DOCUMENTS

| | | |
|---|---|---|
| 5,084,157 A | 1/1992 | Clark et al. |
| 5,185,071 A | 2/1993 | Serwer et al. |
| 5,286,434 A | 2/1994 | Slater et al. |
| 5,384,022 A | 1/1995 | Rajasekaran |
| 5,453,162 A | 9/1995 | Sabanayagam et al. |
| 5,609,743 A | 3/1997 | Sasagawa et al. |
| 5,641,628 A | 6/1997 | Bianchi |
| 5,938,904 A | 8/1999 | Bader et al. |
| 6,036,831 A | 3/2000 | Bishop |
| 6,110,670 A | 8/2000 | Van Broeckhoven et al. |
| 6,146,511 A | 11/2000 | Slater et al. |
| 6,193,866 B1 | 2/2001 | Bader et al. |
| 6,258,540 B1 | 7/2001 | Lo et al. |
| 6,693,620 B1 | 2/2004 | Herb et al. |
| 6,824,664 B1 | 11/2004 | Austin et al. |
| 6,827,830 B1 | 12/2004 | Slater et al. |
| 6,893,546 B2 | 5/2005 | Jullien et al. |
| 6,927,028 B2 | 8/2005 | Dennis et al. |
| 7,175,747 B2 | 2/2007 | Bayerl et al. |
| 7,198,702 B1 | 4/2007 | Washizu et al. |
| 7,371,533 B2 | 5/2008 | Slater et al. |
| 7,427,343 B2 | 9/2008 | Han et al. |
| 7,442,506 B2 | 10/2008 | Dhallan |
| 7,452,668 B2 | 11/2008 | Boles et al. |
| 7,838,647 B2 | 11/2010 | Hahn et al. |
| 7,888,017 B2 | 2/2011 | Quake et al. |
| 8,008,018 B2 | 8/2011 | Quake et al. |
| 8,133,371 B2 | 3/2012 | Marziali et al. |
| 8,182,666 B2 | 5/2012 | Marziali et al. |
| 8,195,415 B2 | 6/2012 | Fan et al. |
| 2001/0045359 A1 | 11/2001 | Cheng et al. |
| 2002/0036139 A1 | 3/2002 | Becker et al. |
| 2002/0081280 A1 | 6/2002 | Curiel et al. |
| 2002/0119448 A1 | 8/2002 | Sorge et al. |
| 2002/0179445 A1 | 12/2002 | Alajoki et al. |
| 2003/0027178 A1 | 2/2003 | Vasmatzis et al. |
| 2003/0215855 A1 | 11/2003 | Dubrow et al. |
| 2005/0164241 A1 | 7/2005 | Hahn et al. |
| 2005/0164402 A1 | 7/2005 | Belisle et al. |
| 2005/0247563 A1 | 11/2005 | Shuber et al. |
| 2005/0247564 A1 | 11/2005 | Volkel et al. |
| 2007/0215472 A1 | 9/2007 | Slater et al. |
| 2007/0218494 A1 | 9/2007 | Slater et al. |
| 2008/0108063 A1 | 5/2008 | Lucero et al. |
| 2008/0314751 A1 | 12/2008 | Bukshpan et al. |
| 2009/0120795 A1 | 5/2009 | Marziali et al. |
| 2009/0139867 A1 | 6/2009 | Marziali et al. |
| 2009/0152116 A1 | 6/2009 | Boles et al. |
| 2010/0273219 A1 | 10/2010 | May et al. |
| 2010/0285537 A1 | 11/2010 | Zimmermann |
| 2011/0048950 A1 | 3/2011 | Marziali et al. |
| 2011/0152111 A1 | 6/2011 | Fan et al. |
| 2011/0245482 A1 | 10/2011 | Hahn et al. |
| 2011/0272282 A1 | 11/2011 | Marziali et al. |
| 2012/0035062 A1 | 2/2012 | Schultz et al. |
| 2012/0048735 A1 | 3/2012 | Marziali et al. |
| 2012/0160682 A1 | 6/2012 | Marziali et al. |
| 2012/0199481 A1 | 8/2012 | Marziali et al. |

FOREIGN PATENT DOCUMENTS

| | | |
|---|---|---|
| CA | 2496294 A1 | 8/2006 |
| CA | 2641326 A1 | 8/2006 |
| CA | 2713313 A1 | 8/2009 |
| CA | 2742460 A1 | 5/2010 |
| EP | 0356187 A2 | 2/1990 |
| EP | 1720636 A1 | 11/2006 |
| EP | 1859249 AO | 11/2007 |
| EP | 2238434 AO | 10/2010 |
| EP | 2458004 A1 | 5/2012 |
| GB | 2249395 A | 5/1992 |
| JP | 7-167837 A | 7/1995 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 A | 3/2003 |
| JP | 2003-513240 A | 4/2003 |
| JP | 2003-215099 A | 7/2003 |
| JP | 2003-247980 A | 9/2003 |
| WO | 9514923 A1 | 6/1995 |
| WO | 9727933 A1 | 8/1997 |
| WO | 9938874 A2 | 8/1999 |
| WO | 9945374 A2 | 9/1999 |
| WO | 0131325 A1 | 5/2001 |
| WO | 0242500 A2 | 5/2002 |
| WO | 03019172 A2 | 3/2003 |
| WO | 2005072854 A1 | 8/2005 |
| WO | 2006063625 A1 | 6/2006 |
| WO | 2006081691 A1 | 8/2006 |
| WO | 2007092473 A2 | 8/2007 |
| WO | 2009094772 A1 | 8/2009 |
| WO | 2010051649 A1 | 5/2010 |
| WO | 20101104798 A1 | 9/2010 |
| WO | 2010121381 A1 | 10/2010 |
| WO | 201302616 A2 | 1/2013 |

OTHER PUBLICATIONS

Varley, K. E. et al., Genome Res., vol. 18, pp. 1844-1850 (2008).*
Nachman, M. W. et al., Genetics, vol. 156, pp. 297-304 (2000).*
Li-Sucholeiki, X-C. et al., Nucl. Acids Res., vol. 28, e44, pp. i-viii (2000).*
Asbury, et al., "Trapping of DNA by dielectrophoresis", Electrophoresis, 2002, 23:2658-2666.
Asbury, et al., "Trapping of DNA in Nonuniform Oscillating Electric Fields", Biophysical Journal, 1998, 74:1024-1030.
Astumian, et al., "Fluctuation Driven Ratchets: Molecular Motors", Physical Review Letters, 1994, 72(11):1766-1769.
Baba, Yoshinobu, "Capillary Affinity Gel Electrophoresis", Molecular Biotechnology, 1996, (9):1-11.
Bier, Martin, et al., "Biasing Brownian Motion in Different Directions in a 3-State Fluctuating Potential and an Application for the Separation of Small Particles", Physical Review Letters, 1996, 76(22):4277-4280.
Broemeling, D., et al., "An Instrument for Automated Purification of Nucleic Acids from Contaminated Forensic Samples", JALA 2008, 13, 40-48.
Carle, G.F., et al., "Electrophoretic Separations of Large DNA Molecules by Periodic Inversion of the Electric Field", Science, 1986, 232(4726):65-68.
Chacron, M.J., et al., "Particle trapping and self-focusing in temporarily asymmetric ratchets with strong field gradients", Physical Review E, 1997, 56(3):3446-3450.
Chakrabarti, Subrata, et al., "Highly Selective Isolation of Unknown Mutations in Diverse DNA Fragments: Toward New Multiplex Screening in Cancer", American Association for Cancer Reserch, 2000, 60:3732-3737.
Chan, K.C. Allen, et al., "Size Distributions of Maternal and Fetal DNA in Maternal Plasma", Molecular Diagnostics and Genetics, Clinical Chemistry, 2004, 50(1):88-92.
Chu, Gilbert, "Bag model for Dna migration during pulsed-field electrophoresis", Proc. Natl. Acad. Sci., 1991, 88:11071-11075.
European Search Report corresponding to EP11004417, 29 Mar. 2012, 4 pages.
Frumin, L.L., et al., "Anomalous size dependence of the non-linear mobility of DNA", in PhysChemComm, 2000, 11 (3):61-63.
Frumin, L.L., et al., "Nonlinear focusing of DNA macromolecules", Physical Review E—Statistical, Nonlinear and Soft Matter Physics, 2001, 64:021902-1-5.
Griess, Gary A., et al., "Cyclic capillary electrophoresis", Electrophoresis, 2002, 23:2610-2617.
International Preliminary Report on Patentability corresponding to PCT/CA2005/000124, Aug. 7, 2006, 8 pages.
International Preliminary Report on Patentability corresponding to PCT/CA2006/000172, Aug. 7, 2007, 8 pages.
International Preliminary Report on Patentability corresponding to PCT/CA2009/000111, Aug. 3, 2010, 9 pages.

(56) References Cited

OTHER PUBLICATIONS

International Seach Report and Written Opinion for PCT/US13/39553 dated Sep. 18, 2013, pp. 13.
International Search Report dated Feb. 23, 2010 corresponding to PCT/CA2009/001648, 6 pages.
International Search Report for PCT/CA2006/000172, International Searching Authority, Jun. 2, 2006, 4 pages.
International Search Report for PCT/CA20121050576, Feb. 28, 2013 3 pages.
Jorgez, Carolina J., et al., "Quantity versus quality: Optimal methods for cell-free DNA isolation from plasma of pregnant women", American College of Medical Genetics, 2006, 8(10):615-619.
Kitzman, Jacob O., et al., "Noninvasive Whole-Genome Sequencing of a Human Fetus", Sci Trans! Med 4, 137ra76 (2012); DOI: 10.1126/scitranslmed.3004323, 9 pages.
Kopecka, K., et al., "Capillary electrophoresis sequencing of small ssDNA molecules versus the Ogston regime: Fitting data and interpreting parameters", Electrophoresis, 2004, 25(14):2177-2185.
LaLande, Marc, et al., "Pulsed-field electrophoresis: Application of a computer model to the separation of large DNA molecules", Proc. Natl. Acad. Sci. USA, 1987, 84:8011-8015.
Lun, Fiona M. F., et al., "Microfluidics Digital PCR Reveals a Higher than Expected Fraction of Fetal DNA in Maternal Plasma", Molecular Diagnostics and Genetics, Clinical Chemistry, 2008, 54(10):1664-1672.
Magnasco, Marcelo, O., "Forced Thermal Ratchets", Physical Review Letters, 1993, 71(10):1477-1481.
Makridakis, Nick M., "PCR-free method detects high frequency of genomic instability in prostate cancer", Nucleic Acids Research, 2009, 37(22):7441-7446.
Marziali, a., et al., "Novel electrophoresis mechanism based on synchronous alternating drag perturbation", Electrophoresis 2005, 26:82-90, published on-line Dec. 28, 2004 at URL www.3.interscience.wiley.com/cgi-bin/issue/109861245.
Nollau, Peter, et al., "Methods for detection of point mutations: performance and quality assessment", Department of Clinical Chemistry, 1997, 43(7):1114-1128.
Office Action mailed Aug. 19, 2011 for U.S. Appl. No. 11/815,760.
Office Action mailed Dec. 27, 2010 for U.S. Appl. No. 11/815,760.
Pel, J., "A novel electrophoretic mechanism and separation parameter for selective nucleic acid concentration based on synchronous coefficient of drag alteration (SCODA)", (Ph.D. Thesis), Vancouver: University of British Columbia, 2009.
Pel, J., et al., "Nonlinear electrophoretic response yields a unique parameter for separation of biomolecules", PNAS 2009, vol. 106, No. 35, 14796-14801.
Rousseau, J., et al., "Gel electrophoretic mobility of single-stranded DNA: The two reptation field-dependent factors", Electrophoresis, 2000, 21(8):1464-1470.
Sikora, Aleksandra, et al., "Detection of Increased Amounts of Cell-Free DNA with Short PCR Amplicons", Clinical Chemistry, 2010, 56(1):136-138.
Slater, G.W., et al., "Recent developments in DNA electrophoretic separations", Electrophoresis, 1998, 19 (10):1525-1541.
Slater, G.W., et al., "The theory of DNA separation by capillary electrophoresis", Current Opinion in Biotechnology, 2003, 14:58-64.
Slater, G.W., et al., "Theory of DNA electrophoresis: A look at some current challenges", Electrophoresis, 2000, 21:3873-3887.
So. A., et al., "Efficient genomic DNA extraction from low target concentration bacterial cultures using SCODA DNA extraction technology", Cold Spring Harb Protoc, 2010, 1150-1153; 1185-1198.
Supplementary European Search Report corresponding to EP09706657, May 12, 2011, 2 pages.
Supplementary Partial European Search Report corresponding to EP05706448, May 14, 2012, 3 pages.
Tessier, F., et al., "Strategies for the separation of polyelectrolytes based on non-linear dynamics and entropic ratchets in a simple microfluidic device", Applied Physics A—Materials Science & Processing, 2002, 75:285-291.
Turmel, C., et al., "Molecular detrapping and band narrowing with high frequency modulation of pulsed field electrophoresis", Nucleic Acids Research, 1990, 18(3):569-575.
Viovy, J.L., "Electrophoresis of DNA and other polyelectrolytes: Physical mechanisms", Review of Modern Physics, 2000, 72(3):813-872.
Wright, Caroline, "Cell-free fetal nucleic acids for non-invasive prenatal diagnosis", Report of the UK export working group, Jan. 2009, 64 pages.
Yobas, L., et al., "Nucleic Acid Extraction, Amplification, and Detection on Si-Based Microfluidic Platforms," IEEE Journal of Solid-State Circuits, vol. 42, No. 8, Aug. 2007, 12 pages.
Extended European Search Report for European Application No. 13784804.0, Mailed Mar. 22, 2016 (7 Pages).

\* cited by examiner

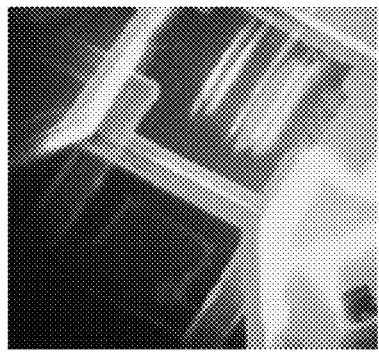 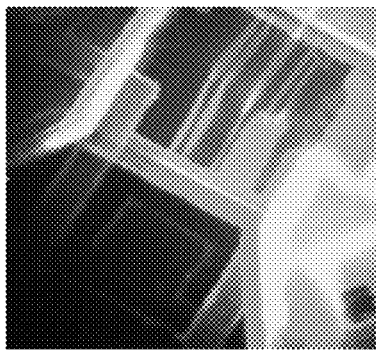 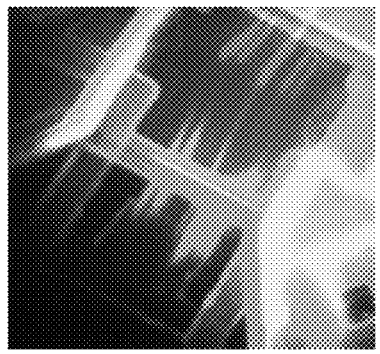
FIGURE 10A    FIGURE 10B    FIGURE 10C
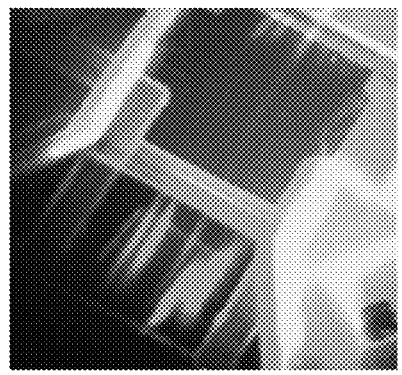 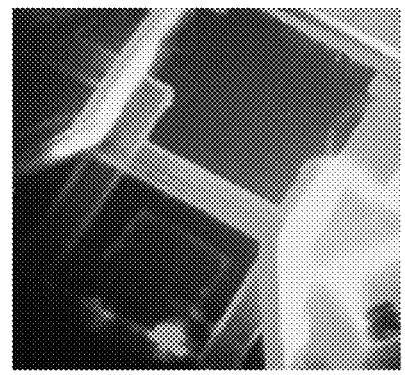
FIGURE 10D    FIGURE 10E

SEQUENCE LISTING

<160> NUMBER OF SEQ ID NOS: 31

<210> SEQ ID NO 1
<211> LENGTH: 2949
<212> TYPE: DNA
<213> ORGANISM: Homo sapiens

<400> SEQUENCE: 1

```
cgcctccctt ccccctcccc gcccgacagc ggccgctcgg gccccggctc tcggttataa      60
gatggcggcg ctgagcggtg gcgtggtggg cggcgcggag ccgggccagg ctctgttcaa     120
cggggacatg gagcccgagg ccggcgccgg cgccggcgcc gcggcctctt cggctgcgga     180
ccctgccatt ccgaggagg tgtggaatat caaacaaatg attaagttga cacaggaaca      240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgatttttc tgtttctagc tctgcatcaa tggataccgt     420
tacatcttct tcctcttcta gcctttcagt gctaccttca tctctttcag tttttcaaaa     480
```

```
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat ccccttccgc   1020
acccgcctcg gactctattg ggccccaaat tctcaccagt ccgtctcctt caaaatccat   1080
tccaattcca cagcccttcc gaccagcaga tgaagatcat cgaaatcaat ttgggcaacg   1140
agaccgatcc tcatcagctc ccaatgtgca tataaacaca atagaacctg tcaatattga   1200
tgacttgatt agagaccaag gatttcgtgg tgatggagga tcaaccacag gtttgtctgc   1260
taccccccct gcctcattac ctggctcact aactaacgtg aaagccttac agaaatctcc   1320
aggacctcag cgagaaagga agtcatcttc atcctcagaa acaggaatc gaatgaaaac    1380 acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta ttgttaccca gtggtgtgag ggctccagct tgtatcacca   1680
tctccatatc attgagacca aatttgagat gatcaaactt atagatattg cacgacagac   1740
tgcacagggc atggattact acacgccaa gtcaatcatc cacagagacc tcaagagtaa    1800
taatatattt cttcatgaag acctcacagt aaaaataggt gattttggtc tagctacagt   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg cagggggata   2340
tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaagaa cacttgtgtg gttaaagact agatataatt tttccccaaa   2520
ctaaaattta tacttaacat tggattttta acatccaagg gttaaaatac atagacattg   2580
ctaaaaattg gcagagcctc ttctagaggc tttactttct gttccgggtt tgtatcattc   2640
acttggttat tttaagtagt aaacttcagt ttctcatgca acttttgttg ccagctatca   2700
catgtccact agggactcca gaagaagacc ctacctatgc ctgtgtttgc aggtgagaag   2760
ttggcagtcg gttagcctgg gttagataag gcaaactgaa cagatctaat ttaggaagtc   2820
agtagaattt aataattcta ttattattct taataatttt tctataacta tttctttta   2880
```

```
taacaatttg gaaaatgtgg atgtcttttta tttccttgaa gcaataaact aagtttctttt    2940 ttataaaaa                                                              2949

<210> SEQ ID NO 2
<211> LENGTH: 5312
<212> TYPE: DNA
<213> ORGANISM: Homo sapiens

<400> SEQUENCE: 2
ggccgcggcg gcggaggcag cagcggcggc ggcagtggcg gcggcgaagg tggcggcggc      60
tcggccagta ctcccggccc ccgccatttc ggactgggag cgagcgcggc gcaggcactg     120
aaggcggcgg cggggccaga ggctcagcgg ctcccaggtg cgggagagag gcctgctgaa     180
aatgactgaa tataaacttg tggtagttgg agctggtggc gtaggcaaga gtgccttgac     240
gatacagcta attcagaatc attttgtgga cgaatatgat ccaacaatag aggattccta     300
caggaagcaa gtagtaattg atggagaaac ctgtctcttg gatattctcg acacagcagg     360
tcaagaggag tacagtgcaa tgagggacca gtacatgagg actggggagg ctttctttg      420 tgtatttgcc ataaataata ctaaatcatt tgaagatatt caccattata gagaacaaat     480
taaaagagtt aaggactctg aagatgtacc tatggtccta gtaggaaata atgtgatttt     540
gccttctaga acagtagaca caaaacaggc tcaggactta gcaagaagtt atggaattcc     600
ttttattgaa acatcagcaa agacaagaca gggtgttgat gatgccttct atacattagt     660
tcgagaaatt cgaaaacata agaaaagat gagcaaagat ggtaaaaaga agaaaaagaa      720
gtcaaagaca aagtgtgtaa ttatgtaaat acaatttgta cttttttctt aaggcatact     780
agtacaagtg gtaattttg tacattacac taaattatta gcatttgttt tagcattacc      840 taatttttt cctgctccat gcagactgtt agcttttacc ttaaatgctt attttaaaat      900
gacagtggaa gttttttttt cctctaagtg ccagtattcc cagagttttg gttttttgaac    960 tagcaatgcc tgtgaaaaag aaactgaata cctaagattt ctgtcttggg gttttttggtg   1020 catgcagttg attacttctt attttttctta ccaattgtga atgttggtgt gaaacaaatt   1080
aatgaagctt tgaatcatc cctattctgt gttttatcta gtcacataaa tggattaatt    1140
actaatttca gttgagacct tctaattggt ttttactgaa acattgaggg aacacaaatt    1200
tatgggcttc ctgatgatga ttcttctagg catcatgtcc tatagtttgt catccctgat    1260
gaatgtaaag ttacactgtt cacaaaggtt ttgtctcctt tccactgcta ttagtcatgg    1320
tcactctccc caaaatatta tattttttct ataaaagaa aaaatggaa aaaaattaca      1380 aggcaatgga aactattata aggccatttc cttttcacat tagataaatt actataaaga    1440
ctcctaatag cttttcctgt taaggcagac ccagtatgaa atgggggatta ttatagcaac   1500 cattttgggg ctatatttac atgctactaa atttttataa taattgaaaa gatttttaaca   1560 agtataaaaa attctcatag gaattaaatg tagtctccct gtgtcagact gctctttcat    1620
agtataactt taaatctttt cttcaacttg agtctttgaa gatagtttta attctgcttg    1680
tgacattaaa agattatttg ggccagttat agcttattag gtgttgaaga gaccaaggtt    1740
gcaaggccag gccctgtgtg aacctttgag ctttcataga gagtttcaca gcatggactg    1800
tgtccccacg gtcatccagt gttgtcatgc attggttagt caaaatgggg agggactagg    1860
gcagtttgga tagctcaaca agatacaatc tcactctgtg gtggtcctgc tgacaaatca    1920
agagcattgc ttttgtttct taagaaaaca aactctttt taaaaattac ttttaaatat     1980
taactcaaaa gttgagattt tggggtggtg gtgtgccaag acattaattt ttttttttaaa   2040
```

```
caatgaagtg aaaaagtttt acaatctcta ggtttggcta gttctcttaa cactggttaa    2100
attaacattg cataaacact tttcaagtct gatccatatt taataatgct ttaaaataaa    2160
aataaaaaca atccttttga taaatttaaa atgttactta ttttaaaata aatgaagtga    2220
gatggcatgg tgaggtgaaa gtatcactgg actaggaaga aggtgactta ggttctagat    2280
aggtgtcttt taggactctg attttgagga catcacttac tatccatttc ttcatgttaa    2340
aagaagtcat ctcaaactct tagtttttt tttttacaac tatgtaattt atattccatt    2400
tacataagga tacacttatt tgtcaagctc agcacaatct gtaaattttt aacctatgtt    2460
acaccatctt cagtgccagt cttgggcaaa attgtgcaag aggtgaagtt tatatttgaa    2520
tatccattct cgttttagga ctcttcttcc atattagtgt catcttgcct ccctaccttc    2580
cacatgcccc atgacttgat gcagttttaa tacttgtaat tcccctaacc ataagattta    2640
ctgctgctgt ggatatctcc atgaagtttt cccactgagt cacatcagaa atgccctaca    2700
tcttatttcc tcagggctca agagaatctg acagatacca taagggatt tgacctaatc    2760
actaattttc aggtggtggc tgatgctttg aacatctctt tgctgcccaa tccattagcg    2820
acagtaggat ttttcaaacc tggtatgaat agacagaacc ctatccagtg aaggagaat    2880
ttaataaaga tagtgctgaa agaattcctt aggtaatcta taactaggac tactcctggt    2940
aacagtaata cattccattg ttttagtaac cagaaatctt catgcaatga aaaatacttt    3000
aattcatgaa gcttactttt tttttttggt gtcagagtct cgctcttgtc acccaggctg    3060
gaatgcagtg gcgccatctc agctcactgc aacctccatc tcccaggttc aagcgattct    3120
cgtgcctcgg cctcctgagt agctgggatt acaggcgtgt gccactacac tcaactaatt    3180
tttgtatttt taggagagac ggggtttcac cctgttggcc aggctggtct cgaactcctg    3240
acctcaagtg attcacccac cttggcctca taaacctgtt ttgcagaact catttattca    3300
gcaaatattt attgagtgcc taccagatgc cagtcaccgc acaaggcact gggtatatgg    3360
tatccccaaa caagagacat aatcccggtc cttaggtagt gctagtgtgg tctgtaatat    3420
cttactaagg cctttggtat acgacccaga gataacacga tgcgtatttt agttttgcaa    3480
agaagggtt tggtctctgt gccagctcta taattgtttt gctacgattc cactgaaact    3540
cttcgatcaa gctactttat gtaaatcact tcattgtttt aaaggaataa acttgattat    3600
attgtttttt tatttggcat aactgtgatt cttttaggac aattactgta cacattaagg    3660
tgtatgtcag atattcatat tgacccaaat gtgtaatatt ccagttttct ctgcataagt    3720
aattaaaata tacttaaaaa ttaatagttt tatctgggta caaataaaca ggtgcctgaa    3780
ctagttcaca gacaaggaaa cttctatgta aaaatcacta tgatttctga attgctatgt    3840
gaaactacag atctttggaa cactgtttag gtagggtgtt aagacttaca cagtacctcg    3900
tttctacaca gagaaagaaa tggccatact tcaggaactg cagtgcttat gagggatat    3960
ttaggcctct tgaattttg atgtagatgg gcattttttt aaggtagtgg ttaattacct    4020
ttatgtgaac tttgaatggt ttaacaaaag atttgttttt gtagagattt taaggggga    4080
gaattctaga aataaatgtt acctaattat tacagcctta aagacaaaaa tccttgttga    4140
agttttttta aaaaaagcta aattacatag acttaggcat taacatgttt gtggaagaat    4200
atagcagacg tatattgtat catttgagtg aatgttccca gtaggcatt ctaggctcta    4260
tttaactgag tcacactgca taggaattta gaacctaact tttataggtt atcaaaactg    4320
ttgtcaccat tgcacaattt tgtcctaata tatacataga aactttgtgg ggcatgttaa    4380
gttacagttt gcacaagttc atctcatttg tattccattg attttttttt tcttctaaac    4440
```

| | | |
|---|---|---|
| atttttctt caaacagtat ataacttttt ttaggggatt ttttttaga cagcaaaaac | 4500 | |
| tatctgaaga tttccatttg tcaaaaagta atgatttctt gataattgtg tagtaatgtt | 4560 | |
| ttttagaacc cagcagttac cttaaagctg aatttatatt tagtaacttc tgtgttaata | 4620 | |
| ctggatagca tgaattctgc attgagaaac tgaatagctg tcataaaatg aaactttctt | 4680 | |
| tctaaagaaa gatactcaca tgagttcttg aagaatagtc ataactagat taagatctgt | 4740 | |
| gttttagttt aatagtttga agtgcctgtt tgggataatg ataggtaatt tagatgaatt | 4800 | |
| taggggaaaa aaaagttatc tgcagatatg ttgagggccc atctctcccc ccacacccccc | 4860 | |
| acagagctaa ctgggttaca gtgttttatc cgaaagtttc caattccact gtcttgtgtt | 4920 | |
| ttcatgttga aaatactttt gcattttttcc tttgagtgcc aatttcttac tagtactatt | 4980 | |
| tcttaatgta acatgtttac ctggaatgta ttttaactat ttttgtatag tgtaaactga | 5040 | |
| aacatgcaca ttttgtacat tgtgctttct tttgtgggac atatgcagtg tgatccagtt | 5100 | |
| gttttccatc atttggttgc gctgacctag gaatgttggt catatcaaac attaaaaatg | 5160 | |
| accactcttt taattgaaat taacttttaa atgtttatag gagtatgtgc tgtgaagtga | 5220 | |
| tctaaaattt gtaatatttt tgtcatgaac tgtactactc ctaattattg taatgtaata | 5280 | |
| aaaatagtta cagtgacaaa aaaaaaaaaa aa | 5312 | |

<210> SEQ ID NO 3
<211> LENGTH: 5616
<212> TYPE: DNA
<213> ORGANISM: Homo sapiens

<400> SEQUENCE: 3

| | | |
|---|---|---|
| ccccggcgca gcgcggccgc agcagcctcc gccccccgca cggtgtgagc gcccgacgcg | 60 | |
| gccgaggcgg ccggagtccc gagctagccc cggcggccgc cgccgcccag accggacgac | 120 | |
| aggccacctc gtcggcgtcc gcccgagtcc ccgcctcgcc gccaacgcca caaccaccgc | 180 | |
| gcacggcccc ctgactccgt ccagtattga tcgggagagc cggagcgagc tcttcgggga | 240 | |
| gcagcgatgc gaccctccgg gacggccggg gcagcgctcc tggcgctgct ggctgcgctc | 300 | |
| tgcccggcga gtcgggctct ggaggaaaag aaagtttgcc aaggcacgag taacaagctc | 360 | |
| acgcagttgg gcacttttga agatcatttt ctcagcctcc agaggatgtt caataactgt | 420 | |
| gaggtggtcc ttgggaattt ggaaattacc tatgtgcaga ggaattatga tcttttccttc | 480 | |
| ttaaagacca tccaggaggt ggctggttat gtcctcattg ccctcaacac agtggagcga | 540 | |
| attcctttgg aaaacctgca gatcatcaga ggaaatatgt actacgaaaa ttcctatgcc | 600 | |
| ttagcagtct tatctaacta tgatgcaaat aaaaccggac tgaaggagct gcccatgaga | 660 | |
| aatttacagg aaatcctgca tggcgccgtg cggttcagca caaccctgc cctgtgcaac | 720 | |
| gtggagagca tccagtggcg ggacatagtc agcagtgact ttctcagcaa catgtcgatg | 780 | |
| gacttccaga accacctggg cagctgccaa aagtgtgatc caagctgtcc caatgggagc | 840 | |
| tgctggggtg caggagagga gaactgccag aaactgacca aaatcatctg tgcccagcag | 900 | |
| tgctccgggc gctgccgtgg caagtccccc agtgactgct gccacaacca gtgtgctgca | 960 | |
| ggctgcacag gccccgggga gcgactgctg gtctgcc gcaaattccg agacgaagcc | 1020 | |
| acgtgcaagg acacctgccc cccactcatg ctctacaacc ccaccacgta ccagatggat | 1080 | |
| gtgaaccccg agggcaaata cagctttggt gccacctgcg tgaagaagtg tccccgtaat | 1140 | |
| tatgtggtga cagatcacgg ctcgtgcgtc cgagcctgtg gggccgacag ctatgagatg | 1200 | |
| gaggaagacg gcgtccgcaa gtgtaagaag tgcgaagggc cttgccgcaa agtgtgtaac | 1260 | |

```
ggaataggta ttggtgaatt taaagactca ctctccataa atgctacgaa tattaaacac    1320
ttcaaaaact gcacctccat cagtggcgat ctccacatcc tgccggtggc atttaggggt    1380
gactccttca cacatactcc tcctctggat ccacaggaac tggatattct gaaaaccgta    1440
aaggaaatca cagggttttt gctgattcag gcttggcctg aaaacaggac ggacctccat    1500
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg ggacctccgg tcagaaaacc aaaattataa gcaacagagg tgaaaacagc    1740
tgcaaggcca caggccaggt ctgccatgcc ttgtgctccc ccgagggctg ctggggcccg    1800
gagcccaggg actgcgtctc ttgccggaat gtcagccgag gcaggaatg cgtggacaag    1860 tgcaaccttc tggagggtga gccaagggag tttgtggaga actctgagtg catacagtgc    1920
cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag tcttgaagg ctgtccaacg    2160 aatgggccta agatcccgtc catcgccact gggatggtgg gggccctcct cttgctgctg    2220
gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc cccacgtgtg ccgcctgctg    2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caagggcat gaactacttg gaggaccgtc gcttggtgca ccgcgacctg    2760
gcagccagga acgtactggt gaaaacaccg cagcatgtca agatcacaga ttttggctg    2820 gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatga agaatgcat ttgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca tcagcctct gaaccccgcg    3600 cccagcagag acccacacta ccaggacccc cacagcactg cagtgggcaa cccgagtat    3660
```

```
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaataccta    3840
agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt cccttgagc agaaatttat     4140
ctttcaaaga ggtatatttg aaaaaaaaaa aaagtatatg tgaggatttt tattgattgg    4200
ggatcttgga gttttcatt gtcgctattg atttttactt caatgggctc ttccaacaag     4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgccctg tcttgctgtc atgaaatcag     4680
caagagagga tgacacatca ataataact cggattccag cccacattgg attcatcagc     4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920
acccccaaa attagtttgt gttacttatg gaagatagtt ttctcctttt acttcacttc     4980
aaaagctttt tactcaaaga gtatatgttc cctccaggtc agctgccccc aaacccctc     5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
agatgtttta gaaggaaaaa agttccttcc taaaataatt tctctacaat tggaagattg    5280
gaagattcag ctagttagga gcccaccttt tttcctaatc tgtgtgtgcc ctgtaacctg    5340
actggttaac agcagtcctt tgtaaacagt gtttttaaact ctcctagtca atatccaccc   5400
catccaattt atcaaggaag aaatggttca gaaatatttt tcagcctaca gttatgttca    5460
gtcacacaca catacaaaat gttccttttg ctttttaaagt aatttttgac tcccagatca   5520
gtcagagccc ctacagcatt gttaagaaag tatttgattt ttgtctcaat gaaaataaaa    5580
ctatattcat ttccactcta aaaaaaaaa aaaaaa                               5616
```

<210> SEQ ID NO 4
<211> LENGTH: 3424
<212> TYPE: DNA
<213> ORGANISM: Homo sapiens

<400> SEQUENCE: 4

```
aggatcagaa caatgcctcc aagaccatca tcaggtgaac tgtggggcat ccacttgatg      60
cccccaagaa tcctagtgga atgtttacta ccaaatggaa tgatagtgac tttagaatgc     120
ctccgtgagg ctacattagt aactataaag catgaactat ttaaagaagc aagaaaatac    180
```

```
cctctccatc aacttcttca agatgaatct tcttacattt tcgtaagtgt tacccaagaa      240
gcagaaaggg aagaattttt tgatgaaaca agacgacttt gtgatcttcg gcttttcaa       300 ccatttttaa aagtaattga accagtaggc aaccgtgaag aaaagatcct caatcgagaa      360
attggttttg ctatcggcat gccagtgtgc gaatttgata tggttaaaga tcctgaagta     420
caggacttcc gaagaaatat tcttaatgtt tgtaaagaag ctgtggatct tagggatctt     480
aattcacctc atagtagagc aatgtatgtc tatccgccac atgtagaatc ttcaccagag     540
ctgccaaagc acatatataa taaattggat agaggccaaa taatagtggt gatttgggta    600
atagtttctc caaataatga caagcagaag tatactctga aaatcaacca tgactgtgtg    660
ccagaacaag taattgctga agcaatcagg aaaaaaacta agagtatgtt gctatcatct    720
gaacaattaa aactctgtgt tttagaatat cagggcaagt acattttaaa agtgtgtgga    780
tgtgatgaat acttcctaga aaaatatcct ctgagtcagt ataagtatat aagaagctgt    840
ataatgcttg ggaggatgcc caatttgaag atgatggcta agaaagcct ttattctcaa    900 ctgccaatgg actgttttac aatgccatct tattccagac gcatttccac agctacacca    960
tatatgaatg gagaaacatc tacaaaatcc ctttgggtta taaatagagc actcagaata    1020
aaaattcttt gtgcaaccta cgtgaatcta aatattcgag acattgacaa gatttatgtt    1080
cgaacaggta tctaccatgg aggagaaccc ttatgtgaca atgtgaacac tcaaagagta    1140
ccttgttcca atcccaggtg gaatgaatgg ctgaattatg atatatacat tcctgatctt    1200
cctcgtgctg ctcgactttg cctttccatt tgctctgtta aaggccgaaa gggtgctaaa    1260
gaggaacact gtccattggc atggggaaat ataaacttgt tgattacac agacactcta    1320 gtatctggaa aaatggcttt gaatctttgg ccagtacctc atggattaga agatttgctg    1380
aaccctattg gtgttactgg atcaaatcca aataaagaaa ctccatgctt agagttggag    1440
tttgactggt tcagcagtgt ggtaaagttc ccagatatgt cagtgattga agagcatgcc    1500
aattggtcta tatcccgaga agcaggattt agctattccc acgcaggact gagtaacaga    1560
ctagctagag acaatgaatt aagggaaaat gacaaagaac agctcaaagc aatttctaca    1620
cgagatcctc tctctgaaat cactgagcag gagaaagatt ttctatggag tcacagacac    1680
tattgtgtaa ctatccccga aattctaccc aaattgcttc tgtctgttaa atggaattct    1740
agagatgaag tagcccagat gtattgcttg gtaaaagatt ggcctccaat caaacctgaa    1800
caggctatgg aacttctgga ctgtaattac ccagatccta tggttcgagg ttttgctgtt    1860
cggtgcttgg aaaaatattt aacagatgac aaactttctc agtatttaat tcagctagta    1920
caggtcctaa aatatgaaca atatttggat aacttgcttg tgagattttt actgaagaaa    1980
gcattgacta tcaaaggat tgggcacttt tctttttggc atttaaaatc tgagatgcac    2040
aataaaacag ttagccagag gtttggcctg cttttggagt cctattgtcg tgcatgtggg    2100
atgtatttga agcacctgaa taggcaagtc gaggcaatgg aaaagctcat taacttaact    2160
gacattctca acaggagag gaaggatgaa acacaaaagg tacagatgaa gttttagtt    2220 gagcaaatga ggcgaccaga tttcatggat gccctacagg gcttgctgtc tcctctaaac    2280
cctgctcatc aactaggaaa cctcaggctt aaagagtgtc gaattatgtc ttctgcaaaa    2340
aggccactgt ggttgaattg ggagaaccca gacatcatgt cagagttact gtttcagaac    2400
aatgagatca tcttaaaaa tggggatgat ttacggcaag atatgctaac acttcaaatt    2460
attcgtatta tggaaaatat ctggcaaaat caaggtcttg atcttcgaat gttaccttat    2520
ggttgtctgt caatcggtga ctgtgtggga cttattgagg tggtgcgaaa ttctcacact    2580
```

| | |
|---|---|
| attatgcaaa ttcagtgcaa aggcggcttg aaaggtgcac tgcagttcaa cagccacaca | 2640 |
| ctacatcagt ggctcaaaga caagaacaaa ggagaaatat atgatgcagc cattgacctg | 2700 |
| tttacacgtt catgtgctgg atactgtgta gctaccttca ttttgggaat tggagatcgt | 2760 |
| cacaatagta acatcatggt gaaagacgat ggacaactgt ttcatataga ttttggacac | 2820 |
| tttttggatc acaagaagaa aaaatttggt tataaacgag aacgtgtgcc atttgttttg | 2880 |
| acacaggatt tcttaatagt gattagtaaa ggagcccaag aatgcacaaa gacaagagaa | 2940 |
| tttgagaggt ttcaggagat gtgttacaag gcttatctag ctattcgaca gcatgccaat | 3000 |
| ctcttcataa atcttttctc aatgatgctt ggctctggaa tgccagaact acaatctttt | 3060 |
| gatgacattg catacattcg aaagacccta gccttagata aaactgagca agaggctttg | 3120 |
| gagtatttca tgaaacaaat gaatgatgca catcatggtg gctggacaac aaaaatggat | 3180 |
| tggatcttcc acacaattaa acagcatgca ttgaactgaa agataactga gaaaatgaaa | 3240 |
| gctcactctg gattccacac tgcactgtta ataactctca gcaggcaaag accgattgca | 3300 |
| taggaattgc acaatccatg aacagcatta gatttacagc aagaacagaa ataaaatact | 3360 |
| atataattta ataatgtaaa acgcaaacag ggtttgatag cacttaaact agttcatttc | 3420 |
| aaaa | 3424 |

<210> SEQ ID NO 5
<211> LENGTH: 6267
<212> TYPE: DNA
<213> ORGANISM: Homo sapiens

<400> SEQUENCE: 5

| | |
|---|---|
| agctgcaagt ggcgggcgcc caggcagatg cgatccagcg gctctggggg cggcagcggt | 60 |
| ggtagcagct ggtacctccc gccgcctctg ttcggagggt cgcggggcac cgaggtgctt | 120 |
| tccggccgcc ctctggtcgg ccacccaaag ccgcgggcgc tgatgatggg tgaggagggg | 180 |
| gcggcaagat tcgggcgcc cctgccctga acgccctcag ctgctgccgc cggggccgct | 240 |
| ccagtgcctg cgaactctga ggagccgagg cgccggtgag agcaaggacg ctgcaaactt | 300 |
| gcgcagcgcg ggggctggga ttcacgccca gaagttcagc aggcagacag tccgaagcct | 360 |
| tcccgcagcg gagagatagc ttgagggtgc gcaagacggc agcctccgcc ctcggttccc | 420 |
| gcccagaccg ggcagaagag cttggaggag ccaaaaggaa cgcaaaaggc ggccaggaca | 480 |
| gcgtgcagca gctgggagcc gccgttctca gccttaaaag ttgcagagat tggaggctgc | 540 |
| cccgagaggg gacagacccc agctccgact gcgggggggca ggagaggacg gtacccaact | 600 |
| gccacctccc ttcaaccata gtagttcctc tgtaccgagc gcagcgagct acagacgggg | 660 |
| gcgcggcact cggcgcggag agcgggaggc tcaaggtccc agccagtgag cccagtgtgc | 720 |
| ttgagtgtct ctggactcgc ccctgagctt ccaggtctgt ttcatttaga ctcctgctcg | 780 |
| cctccgtgca gttggggggaa agcaagagac ttgcgcgcac gcacagtcct ctggagatca | 840 |
| ggtggaagga gccgctgggt accaaggact gttcagagcc tcttcccatc tcggggagag | 900 |
| cgaagggtga ggctgggccc ggagagcagt gtaaacggcc tcctccggcg ggatgggagc | 960 |
| catcgggctc ctgtggctcc tgccgctgct gctttccacg gcagctgtgg gctccgggat | 1020 |
| ggggaccggc cagcgcgcgg gctccccagc tgcggggccg ccgctgcagc cccgggagcc | 1080 |
| actcagctac tcgcgcctgc agaggaagag tctggcagtt gacttcgtgg tgccctcgct | 1140 |
| cttccgtgtc tacgcccggg acctactgct gccaccatcc tcctcggagc tgaaggctgg | 1200 |
| caggcccgag gcccgcggct cgctagctct ggactgcgcc ccgctgctca ggttgctggg | 1260 |

```
gccggcgccg ggggtctcct ggaccgccgg ttcaccagcc ccggcagagg cccggacgct   1320
gtccagggtg ctgaagggcg gctccgtgcg caagctccgg cgtgccaagc agttggtgct   1380
ggagctgggc gaggaggcga tcttggaggg ttgcgtcggg cccccggggg aggcggctgt   1440
ggggctgctc cagttcaatc tcagcgagct gttcagttgg tggattcgcc aaggcgaagg   1500
gcgactgagg atccgcctga tgcccgagaa gaaggcgtcg gaagtgggca gagagggaag   1560
gctgtccgcg gcaattcgcg cctcccagcc ccgccttctc ttccagatct tcggactggg   1620
tcatagctcc ttggaatcac caacaaacat gccttctcct tctcctgatt attttacatg   1680
gaatctcacc tggataatga aagactcctt cccttcctg tctcatcgca gccgatatgg   1740
tctggagtgc agctttgact tcccctgtga gctggagtat tcccctccac tgcatgacct   1800
caggaaccag agctggtcct ggcgccgcat ccctccgag gaggcctccc agatggactt   1860
gctggatggg cctggggcag agcgttctaa ggagatgccc agaggctcct ttctccttct   1920
caacacctca gctgactcca gcacaccat cctgagtccg tggatgagga gcagcagtga   1980
gcactgcaca ctggccgtct cggtgcacag gcacctgcag ccctctggaa ggtacattgc   2040
ccagctgctg ccccacaacg aggctgcaag agagatcctc ctgatgccca ctccagggaa   2100
gcatggttgg acagtgctcc agggaagaat cgggcgtcca gacaacccat ttcgagtggc   2160
cctggaatac atctccagtg gaaaccgcag cttgtctgca gtggacttct ttgccctgaa   2220
gaactgcagt gaaggaacat ccccaggctc caagatggcc ctgcagagct ccttcacttg   2280
ttggaatggg acagtcctcc agcttgggca ggcctgtgac ttccaccagg actgtgccca   2340
gggagaagat gagagccaga tgtgccggaa actgcctgtg ggtttttact gcaactttga   2400
agatggcttc tgtggctgga cccaaggcac actgtcaccc cacactcctc aatggcaggt   2460
caggacccta aaggatgccc ggttccagga ccaccaagac catgctctat tgctcagtac   2520
cactgatgtc cccgcttctg aaagtgctac agtgaccagt gctacgtttc ctgcaccgat   2580
caagagctct ccatgtgagc tccgaatgtc ctggctcatt cgtggagtct tgaggggaaa   2640
cgtgtccttg gtgctagtgg agaacaaaac cgggaaggag caaggcagga tggtctggca   2700
tgtcgccgcc tatgaaggct tgagcctgtg gcagtggatg tgttgcctc tcctcgatgt   2760 gtctgacagg ttctggctgc agatggtcgc atggtgggga caaggatcca gagccatcgt   2820
ggcttttgac aatatctcca tcagcctgga ctgctacctc accattagcg gagaggacaa   2880
gatcctgcag aatacagcac ccaaatcaag aaacctgttt gagagaaacc caaacaagga   2940
gctgaaaccc ggggaaaatt caccaagaca gaccccatc tttgacccta cagttcattg   3000
gctgttcacc acatgtgggg ccagcgggcc ccatggcccc acccaggcac agtgcaacaa   3060
cgcctaccag aactccaacc tgagcgtgga ggtggggagc gagggccccc tgaaaggcat   3120
ccagatctgg aaggtgccag ccaccgacac ctacagcatc tcgggctacg agctgctgg   3180 cgggaaaggc gggaagaaca ccatgatgcg gtcccacggc gtgtctgtgc tgggcatctt   3240
caacctggag aaggatgaca tgctgtacat cctggttggg cagcagggag aggacgcctg   3300
ccccagtaca aaccagttaa tccagaaagt ctgcattgga gagaacaatg tgatagaaga   3360
agaaatccgt gtgaacagaa gcgtgcatga gtgggcagga ggcggaggag gaggggtggg   3420
agccacctac gtatttaaga tgaaggatgg agtgccggtg cccctgatca ttgcagccgg   3480
aggtggtggc agggcctacg gggccaagac agacacgttc cacccagaga gactggagaa   3540
taactcctcg gttctagggc taaacggcaa ttcggagcc gcaggtggtg gaggtggctg   3600
gaatgataac acttccttgc tctgggccgg aaaatctttg caggagggtg ccaccggagg   3660
```

```
acattcctgc ccccaggcca tgaagaagtg ggggtgggag acaagagggg gtttcggagg   3720
gggtggaggg gggtgctcct caggtggagg aggcggagga tatataggcg gcaatgcagc   3780
ctcaaacaat gaccccgaaa tggatgggga agatggggtt tccttcatca gtccactggg   3840
catcctgtac accccagctt taaaagtgat ggaaggccac ggggaagtga atattaagca   3900
ttatctaaac tgcagtcact gtgaggtaga cgaatgtcac atggaccctg aaagccacaa   3960
ggtcatctgc ttctgtgacc acgggacggt gctggctgag gatggcgtct cctgcattgt   4020
gtcacccacc ccggagccac acctgccact ctcgctgatc ctctctgtgg tgacctctgc   4080
cctcgtggcc gccctggtcc tggctttctc cggcatcatg attgtgtacc gccggaagca   4140
ccaggagctg caagccatgc agatggagct gcagagccct gagtacaagc tgagcaagct   4200
ccgcacctcg accatcatga ccgactacaa ccccaactac tgctttgctg gcaagacctc   4260
ctccatcagt gacctgaagg aggtgccgcg gaaaaacatc accctcattc ggggtctggg   4320
ccatggcgcc tttggggagg tgtatgaagg ccaggtgtcc ggaatgccca acgacccaag   4380
cccccctgcaa gtggctgtga agacgctgcc tgaagtgtgc tctgaacagg acgaactgga   4440
tttcctcatg gaagccctga tcatcagcaa attcaaccac cagaacattg ttcgctgcat   4500
tgggggtgagc ctgcaatccc tgccccggtt catcctgctg gagctcatgg cgggggagga   4560
cctcaagtcc ttcctccgag agacccgccc tcgcccgagc cagccctcct ccctggccat   4620
gctggacctt ctgcacgtgg ctcgggacat tgcctgtggc tgtcagtatt tggaggaaaa   4680
ccacttcatc caccgagaca ttgctgccag aaactgcctc ttgacctgtc caggccctgg   4740
aagagtggcc aagattggag acttcgggat ggcccgagac atctacaggg cgagctacta   4800
tagaaaggga ggctgtgcca tgctgccagt taagtggatg ccccagagg ccttcatgga   4860
aggaatattc acttctaaaa cagacacatg gtcctttgga gtgctgctat gggaaatctt   4920
ttctcttgga tatatgccat accccagcaa aagcaaccag gaagttctgg agtttgtcac   4980
cagtggaggc cggatggacc cacccaagaa ctgccctggg cctgtatacc ggataatgac   5040
tcagtgctgg caacatcagc ctgaagacag gcccaacttt gccatcattt tggagaggat   5100
tgaatactgc acccaggacc cggatgtaat caacaccgct tgccgataga atatggtcc    5160
acttgtggaa gaggaagaga aagtgcctgt gaggcccaag gaccctgagg gggttcctcc   5220
tctcctggtc tctcaacagg caaaacggga ggaggagcgc agcccagctg ccccaccacc   5280
tctgcctacc acctcctctg gcaaggctgc aaagaaaccc acagctgcag agatctctgt   5340
tcgagtccct agagggccgg ccgtggaagg gggacacgtg aatatggcat tctctcagtc   5400
caaccctcct tcggagttgc acaaggtcca cggatccaga aacaagccca ccagcttgtg   5460
gaacccaacg tacggctcct ggtttacaga gaaacccacc aaaaagaata atcctatagc   5520
aaagaaggag ccacacgaca ggggtaacct ggggctggag ggaagctgta ctgtcccacc   5580
taacgttgca actgggagac ttccggggc ctcactgctc ctagagccct cttcgctgac   5640
tgccaatatg aaggaggtac ctctgttcag gctacgtcac ttcccttgtg ggaatgtcaa   5700
ttacggctac cagcaacagg gcttgccctt agaagccgct actgcccctg gagctggtca   5760
ttacgaggat accattctga aaagcaagaa tagcatgaac cagcctgggc cctgagctcg   5820
gtcgcacact cacttctctt ccttgggatc cctaagaccg tggaggagag agaggcaatg   5880
gctccttcac aaaccagaga ccaaatgtca cgttttgttt tgtgccaacc tattttgaag   5940
taccaccaaa aaagctgtat tttgaaaatg ctttagaaag gttttgagca tgggttcatc   6000
ctattctttc gaaagaagaa aatatcataa aaatgagtga taaatacaag gcccagatgt   6060
```

```
ggttgcataa ggttttttatg catgtttgtt gtatacttcc ttatgcttct ttcaaattgt    6120
gtgtgctctg cttcaatgta gtcagaatta gctgcttcta tgtttcatag ttggggtcat    6180
agatgtttcc ttgccttgtt gatgtggaca tgagccattt gaggggagag ggaacggaaa    6240
taaaggagtt atttgtaatg actaaaa                                        6267

<210> SEQ ID NO 6
<211> LENGTH: 10740
<212> TYPE: DNA
<213> ORGANISM: Homo sapiens

<400> SEQUENCE: 6
gtattggtgc agcccgccag ggtgtcactg gagacagaat ggaggtgctg ccggactcgg      60
aaatggggtc caagggtagc caaggatggc tgcagcttca tatgatcagt tgttaaagca     120
agttgaggca ctgaagatgg agaactcaaa tcttcgacaa gagctagaag ataattccaa     180
tcatcttaca aaactggaaa ctgaggcatc taatatgaag gaagtactta aacaactaca     240
aggaagtatt gaagatgaag ctatggcttc ttctggacag attgatttat tagagcgtct     300
taaagagctt aacttagata gcagtaattt ccctggagta aaactgcggt caaaaatgtc     360
cctccgttct tatggaagcc gggaaggatc tgtatcaagc cgttctggag agtgcagtcc     420
tgttcctatg ggttcatttc caagaagagg gtttgtaaat ggaagcagag aaagtactgg     480
atatttagaa gaacttgaga aagagaggtc attgcttctt gctgatcttg acaaagaaga     540
aaaggaaaaa gactggtatt acgctcaact tcagaatctc actaaaagaa tagatagtct     600 tccttttaact gaaaatttttt ccttacaaac agatatgacc agaaggcaat ggaatatga     660 agcaaggcaa atcagagttg cgatggaaga caactaggt acctgccagg atatggaaaa     720
acgagcacag cgaagaatag ccagaattca gcaaatcgaa aaggacatac ttcgtatacg     780
acagctttta cagtcccaag caacagaagc agagaggtca tctcagaaca agcatgaaac     840
cggctcacat gatgctgagc ggcagaatga aggtcaagga gtgggagaaa tcaacatggc     900
aacttctggt aatggtcagg gttcaactac acgaatggac catgaaacag ccagtgtttt     960
gagttctagt agcacacact ctgcacctcg aaggctgaca agtcatctgg gaaccaaggt    1020
ggaaatggtg tattcattgt tgtcaatgct tggtactcat gataaggatg atatgtcgcg    1080
aactttgcta gctatgtcta gctcccaaga cagctgtata tccatgcgac agtctggatg    1140
tcttcctctc ctcatccagc ttttacatgg caatgacaaa gactctgtat tgttgggaaa    1200
ttcccggggc agtaaagagg ctcgggccag ggccagtgca gcactccaca acatcattca    1260
ctcacagcct gatgacaaga gaggcaggcg tgaaatccga gtccttcatc ttttggaaca    1320
gatacgcgct tactgtgaaa cctgttggga gtggcaggaa gctcatgaac caggcatgga    1380
ccaggacaaa aatccaatgc cagctcctgt tgaacatcag atctgtcctg ctgtgtgtgt    1440
tctaatgaaa ctttcatttg atgaagagca tagacatgca atgaatgaac taggggggact    1500 acaggccatt gcagaattat tgcaagtgga ctgtgaaatg tatgggctta ctaatgacca    1560
ctacagtatt acactaagac gatatgctgg aatggctttg acaaacttga cttttggaga    1620
tgtagccaac aaggctacgc tatgctctat gaaaggctgc atgagagcac ttgtgggcca    1680
actaaaatct gaaagtgaag acttacagca ggttattgcg agtgttttga ggaatttgtc    1740
ttggcgagca gatgtaaata gtaaaaagac gttgcgagaa gttggaagtg tgaaagcatt    1800 gatgaatgt gctttagaag ttaaaaagga atcaaccctc aaaagcgtat tgagtgcctt    1860
atggaatttg tcagcacatt gcactgagaa taaagctgat atatgtgctg tagatggtgc    1920
```

```
acttgcattt ttggttggca ctcttactta ccggagccag acaaacactt tagccattat    1980
tgaaagtgga ggtgggatat tacggaatgt gtccagcttg atagctacaa atgaggacca    2040
caggcaaatc ctaagagaga acaactgtct acaaacttta ttacaacact taaaatctca    2100
tagtttgaca atagtcagta atgcatgtgg aactttgtgg aatctctcag caagaaatcc    2160
taaagaccag gaagcattat gggacatggg ggcagttagc atgctcaaga acctcattca    2220
ttcaaagcac aaaatgattg ctatgggaag tgctgcagct ttaaggaatc tcatggcaaa    2280
taggcctgcg aagtacaagg atgccaatat tatgtctcct ggctcaagct tgccatctct    2340
tcatgttagg aaacaaaaag ccctagaagc agaattagat gctcagcact tatcagaaac    2400
ttttgacaat atagacaatt taagtcccaa ggcatctcat cgtagtaagc agagacacaa    2460
gcaaagtctc tatggtgatt atgtttttga caccaatcga catgatgata ataggtcaga    2520
caattttaat actggcaaca tgactgtcct ttcaccatat ttgaatacta cagtgttacc    2580
cagctcctct tcatcaagag gaagcttaga tagttctcgt tctgaaaaag atagaagttt    2640
ggagagagaa cgcggaattg gtctaggcaa ctaccatcca gcaacagaaa atccaggaac    2700
ttcttcaaag cgaggtttgc agatctccac cactgcagcc cagattgcca aagtcatgga    2760
agaagtgtca gccattcata cctctcagga agacagaagt tctgggtcta ccactgaatt    2820
acattgtgtg acagatgaga gaaatgcact tagaagaagc tctgctgccc atacacattc    2880
aaacacttac aatttcacta agtcggaaaa ttcaaatagg acatgttcta tgccttatgc    2940
caaattagaa tacaagagat cttcaaatga tagtttaaat agtgtcagta gtagtgatgg    3000
ttatggtaaa agaggtcaaa tgaaaccctc gattgaatcc tattctgaag atgatgaaag    3060
taagttttgc agttatggtc aatacccagc cgacctagcc cataaaatac atagtgcaaa    3120
tcatatggat gataatgatg gagaactaga tacaccaata aattatagtc ttaaatattc    3180
agatgagcag ttgaactctg gaaggcaaag tccttcacag aatgaaagat gggcaagacc    3240
caaacacata atagaagatg aaataaaaca aagtgagcaa agacaatcaa ggaatcaaag    3300
tacaacttat cctgttttata ctgagagcac tgatgataaa cacctcaagt tccaaccaca    3360
ttttggacag caggaatgtg tttctccata caggtcacgg ggagccaatg gttcagaaac    3420
aaatcgagtg ggttctaatc atggaattaa tcaaaatgta agccagtctt tgtgtcaaga    3480
agatgactat gaagatgata agcctaccaa ttatagtgaa cgttactctg aagaagaaca    3540
gcatgaagaa gaagagagac aacaaattta tagcataaaa tataatgaag agaaacgtca    3600
tgtggatcag cctattgatt atagtttaaa atatgccaca gatattcctt catcacagaa    3660
acagtcattt tcattctcaa agagttcatc tggacaaagc agtaaaaccg aacatatgtc    3720
ttcaagcagt gagaatacgt ccacaccttc atctaatgcc aagaggcaga atcagctcca    3780
tccaagttct gcacagagta gaagtggtca gcctcaaaag gctgccactt gcaaagtttc    3840
ttctattaac caagaaacaa tacagactta ttgtgtagaa gatactccaa tatgttttcc    3900
aagatgtagt tcattatcat ctttgtcatc agctgaagat gaaataggat gtaatcagac    3960
gacacaggaa gcagattctg ctaatacccct gcaaatagca gaaataaaag aaaagattgg    4020
aactaggtca gctgaagatc ctgtgagcga agttccagca gtgtcacagc ccctagaac     4080 caaatccagc agactgcagg gttctagttt atcttcagaa tcagccaggc acaaagctgt    4140
tgaattttct tcaggagcga aatctcccct caaaagtggt gctcagacac ccaaaagtcc    4200
acctgaacac tatgttcagg agccccact catgtttagc agatgtactt ctgtcagttc    4260
acttgatagt tttgagagtc gttcgattgc cagctccgtt cagagtgaac catgcagtgg    4320
```

```
aatggtaagt ggcattataa gccccagtga tcttccagat agccctggac aaaccatgcc   4380
accaagcaga agtaaaacac ctccaccacc tcctcaaaca gctcaaacca agcgagaagt   4440
acctaaaaat aaagcaccta ctgctgaaaa gagagagagt ggacctaagc aagctgcagt   4500
aaatgctgca gttcagaggg tccaggttct tccagatgct gatactttat tacattttgc   4560
cacggaaagt actccagatg gattttcttg ttcatccagc ctgagtgctc tgagcctcga   4620
tgagccattt atacagaaag atgtggaatt aagaataatg cctccagttc aggaaaatga   4680
caatgggaat gaaacagaat cagagcagcc taaagaatca aatgaaaacc aagagaaaga   4740
ggcagaaaaa actattgatt ctgaaaagga cctattagat gattcagatg atgatgatat   4800
tgaaatacta gaagaatgta ttatttctgc catgccaaca aagtcatcac gtaaagcaaa   4860
aaagccagcc cagactgctt caaaattacc tccacctgtg gcaaggaaac caagtcagct   4920
gcctgtgtac aaacttctac catcacaaaa caggttgcaa ccccaaaagc atgttagttt   4980
tacaccgggg gatgatatgc cacgggtgta ttgtgttgaa gggacaccta taaacttttc   5040
cacagctaca tctctaagtg atctaacaat cgaatcccct ccaaatgagt tagctgctgg   5100
agaaggagtt agaggagggg cacagtcagg tgaatttgaa aaacgagata ccattcctac   5160
agaaggcaga agtacagatg aggctcaagg aggaaaaacc tcatctgtaa ccatacctga   5220
attggatgac aataaagcag aggaaggtga tattcttgca gaatgcatta attctgctat   5280
gcccaaaggg aaaagtcaca agcctttccg tgtgaaaaag ataatggacc aggtccagca   5340
agcatctgcg tcttcttctg cacccaacaa aaatcagtta gatggtaaga aaaagaaacc   5400
aacttcacca gtaaaaccta taccacaaaa tactgaatat aggacacgtg taagaaaaaa   5460
tgcagactca aaaaataatt taaatgctga gagagttttc tcagacaaca agattcaaa   5520 gaaacagaat ttgaaaaata attccaaggt cttcaatgat aagctcccaa ataatgaaga   5580
tagagtcaga ggaagttttg cttttgattc acctcatcat tacacgccta ttgaaggaac   5640
tccttactgt ttttcacgaa atgattcttt gagttctcta gattttgatg atgatgatgt   5700 tgaccttttcc agggaaaagg ctgaattaag aaaggcaaaa gaaaataagg aatcagaggc   5760
taaagttacc agccacacag aactaacctc caaccaacaa tcagctaata agacacaagc   5820
tattgcaaag cagccaataa atcgaggtca gcctaaaccc atacttcaga aacaatccac   5880
ttttccccag tcatccaaag acataccaga cagaggggca gcaactgatg aaaagttaca   5940
gaattttgct attgaaaata ctccggtttg cttttctcat aattcctctc tgagttctct   6000
cagtgacatt gaccaagaaa acaacaataa agaaaatgaa cctatcaaag agactgagcc   6060
ccctgactca cagggagaac caagtaaacc tcaagcatca ggctatgctc ctaaatcatt   6120
tcatgttgaa gatacccccag tttgtttctc aagaaacagt tctctcagtt ctcttagtat   6180
tgactctgaa gatgacctgt tgcaggaatg tataagctcc gcaatgccaa aaagaaaaa   6240 gccttcaaga ctcaagggtg ataatgaaaa acatagtccc agaaatatgg gtggcatatt   6300
aggtgaagat ctgacacttg atttgaaaga tatacagaga ccagattcag aacatggtct   6360
atcccctgat tcagaaaatt ttgattggaa agctattcag gaaggtgcaa attccatagt   6420
aagtagttta catcaagctg ctgctgctgc atgtttatct agacaagctt cgtctgattc   6480
agattccatc cttttccctga aatcaggaat ctctctggga tcaccatttc atcttacacc   6540
tgatcaagaa gaaaaaccct ttacaagtaa taaaggccca cgaattctaa aaccagggga   6600
gaaaagtaca ttgaaaacta aaagatagaa atctgaaagt aaaggaatca aggaggaaa   6660 aaaagtttat aaaagtttga ttactggaaa agttcgatct aattcagaaa tttcaggcca   6720
```

| | | | | |
|---|---|---|---|---|
| aatgaaacag | ccccttcaag | caaacatgcc | ttcaatctct | cgaggcagga caatgattca | 6780 |
| tattccagga | gttcgaaata | gctcctcaag | tacaagtcct | gtttctaaaa aaggcccacc | 6840 |
| ccttaagact | ccagcctcca | aaagccctag | tgaaggtcaa | acagccacca cttctcctag | 6900 |
| aggagccaag | ccatctgtga | aatcagaatt | aagccctgtt | gccaggcaga catcccaaat | 6960 |
| aggtgggtca | agtaaagcac | cttctagatc | aggatctaga | gattcgaccc cttcaagacc | 7020 |
| tgcccagcaa | ccattaagta | gacctataca | gtctcctggc | cgaaactcaa tttcccctgg | 7080 |
| tagaaatgga | ataagtcctc | ctaacaaatt | atctcaactt | ccaaggacat catcccctag | 7140 |
| tactgcttca | actaagtcct | caggttctgg | aaaaatgtca | tatacatctc caggtagaca | 7200 |
| gatgagccaa | cagaacctta | ccaaacaaac | aggtttatcc | aagaatgcca gtagtattcc | 7260 |
| aagaagtgag | tctgcctcca | aaggactaaa | tcagatgaat | aatggtaatg agccaataa | 7320 |
| aaaggtagaa | ctttctagaa | tgtcttcaac | taaatcaagt | ggaagtgaat ctgatagatc | 7380 |
| agaaagacct | gtattagtac | gccagtcaac | tttcatcaaa | gaagctccaa gcccaacctt | 7440 |
| aagaagaaaa | ttggaggaat | ctgcttcatt | tgaatctctt | tctccatcat ctagaccagc | 7500 |
| ttctcccact | aggtcccagg | cacaaactcc | agttttaagt | ccttcccttc ctgatatgtc | 7560 |
| tctatccaca | cattcgtctg | ttcaggctgg | tggatggcga | aaactcccac ctaatctcag | 7620 |
| tcccactata | gagtataatg | atggaagacc | agcaaagcgc | catgatattg cacggtctca | 7680 |
| ttctgaaagt | ccttctagac | ttccaatcaa | taggtcagga | acctggaaac gtgagcacag | 7740 |
| caaacattca | tcatcccttc | ctcgagtaag | cacttggaga | agaactggaa gttcatcttc | 7800 |
| aattctttct | gcttcatcag | aatccagtga | aaaagcaaaa | agtgaggatg aaaaacatgt | 7860 |
| gaactctatt | tcaggaacca | acaaagtaa | agaaaaccaa | gtatccgcaa aaggaacatg | 7920 |
| gagaaaaata | aagaaaatg | aattttctcc | cacaaatagt | acttctcaga ccgtttcctc | 7980 |
| aggtgctaca | aatggtgctg | aatcaaagac | tctaatttat | caaatggcac ctgctgtttc | 8040 |
| taaaacagag | gatgtttggg | tgagaattga | ggactgtccc | attaacaatc ctagatctgg | 8100 |
| aagatctccc | acaggtaata | ctccccccggt | gattgacagt | gtttcagaaa aggcaaatcc | 8160 |
| aaacattaaa | gattcaaaag | ataatcaggc | aaaaacaaaat | gtgggtaatg gcagtgttcc | 8220 |
| catgcgtacc | gtgggtttgg | aaaatcgcct | gaactccttt | attcaggtgg atgcccctga | 8280 |
| ccaaaaagga | actgagataa | aaccaggaca | aaataatcct | gtccctgtat cagagactaa | 8340 |
| tgaaagttct | atagtggaac | gtaccccatt | cagttctagc | agctcaagca acacagttc | 8400 |
| acctagtggg | actgttgctg | ccagagtgac | tcctttaat | tacaacccaa gccctaggaa | 8460 |
| aagcagcgca | gatagcactt | cagctcggcc | atctcagatc | ccaactccag tgaataacaa | 8520 |
| cacaaagaag | cgagattcca | aaactgacag | cacagaatcc | agtggaaccc aaagtcctaa | 8580 |
| gcgccattct | gggtcttacc | ttgtgacatc | tgtttaaaag | agaggaagaa tgaaactaag | 8640 |
| aaaattctat | gttaattaca | actgctatat | agacattttg | tttcaaatga actttaaaa | 8700 |
| gactgaaaaa | ttttgtaaat | aggtttgatt | cttgttagag | ggttttttgtt ctggaagcca | 8760 |
| tatttgatag | tatactttgt | cttcactggt | cttattttgg | gaggcactct tgatggttag | 8820 |
| gaaaaaaata | gtaaagccaa | gtatgttttgt | acagtatgtt | ttacatgtat ttaaagtagc | 8880 |
| atcccatccc | aacttccttt | aattattgct | tgtcttaaaa | taatgaacac tacagataga | 8940 |
| aaatatgata | tattgctgtt | atcaatcatt | tctagattat | aaactgacta aacttacatc | 9000 |
| agggaaaaat | tggtatttat | gcaaaaaaaa | atgttttttgt | ccttgtgagt ccatctaaca | 9060 |
| tcataattaa | tcatgtggct | gtgaaattca | cagtaatatg | gttcccgatg aacaagttta | 9120 |

| | |
|---|---|
| cccagcctgc tttgctttac tgcatgaatg aaactgatgg ttcaatttca gaagtaatga | 9180 |
| ttaacagtta tgtggtcaca tgatgtgcat agagatagct acagtgtaat aatttacact | 9240 |
| attttgtgct ccaaacaaaa caaaaatctg tgtaactgta aaacattgaa tgaaactatt | 9300 |
| ttacctgaac tagattttat ctgaaagtag gtagaatttt tgctatgctg taatttgttg | 9360 |
| tatattctgg tatttgaggt gagatggctg ctctttatt aatgagacat gaattgtgtc | 9420 |
| tcaacagaaa ctaaatgaac atttcagaat aaattattgc tgtatgtaaa ctgttactga | 9480 |
| aattggtatt tgtttgaagg gtcttgtttc acatttgtat taataattgt ttaaaatgcc | 9540 |
| tcttttaaaa gcttatataa attttttct tcagcttcta tgcattaaga gtaaaattcc | 9600 |
| tcttactgta ataaaaacaa ttgaagaaga ctgttgccac ttaaccattc catgcgttgg | 9660 |
| cacttatcta ttcctgaaat ttcttttatg tgattagctc atcttgattt ttaatatttt | 9720 |
| tccacttaaa ctttttttc ttactccact ggagctcagt aaaagtaaat tcatgtaata | 9780 |
| gcaatgcaag cagcctagca cagactaagc attgagcata ataggcccac ataatttcct | 9840 |
| ctttcttaat attatagaat tctgtacttg aaattgattc ttagacattg cagtctcttc | 9900 |
| gaggctttac agtgtaaact gtcttgcccc ttcatcttct tgttgcaact gggtctgaca | 9960 |
| tgaacacttt ttatcaccct gtatgttagg gcaagatctc agcagtgaag tataatcagc | 10020 |
| actttgccat gctcagaaaa ttcaaatcac atggaacttt agaggtagat ttaatacgat | 10080 |
| taagatattc agaagtatat tttagaatcc ctgcctgtta aggaaacttt atttgtggta | 10140 |
| ggtacagttc tggggtacat gttaagtgtc cccttataca gtggagggaa gtcttccttc | 10200 |
| ctgaaggaaa ataaactgac acttattaac taagataatt tacttaatat atcttccctg | 10260 |
| atttgtttta aaagatcaga gggtgactga tgatacatgc atacatattt gttgaataaa | 10320 |
| tgaaaattta tttttagtga taagattcat acactctgta tttggggagg gaaaaccttt | 10380 |
| ttaagcatgg tggggcactc agataggagt gaatacacct acctggtgcc ttgaaaatca | 10440 |
| catcaagtag ttaattatct accccttacc tgtgtttata acttccaggt aatgagaatg | 10500 |
| attttttta aagctaaaat gccagtaaat aaaagtgcta tgacttgagc taagatattt | 10560 |
| gactccaatg cctgtactgt gtctactgca ccacttttgta aacacttcaa tttactatct | 10620 |
| ttgaaatgat tgacctttaa attttttgcca aatgttatct gaaattgtct atgaatacca | 10680 |
| tctacttctg ttgttttccc aggcttccat aaacaatgga gatacatgca aaaaaaaaa | 10740 |

<210> SEQ ID NO 7
<211> LENGTH: 3720
<212> TYPE: DNA
<213> ORGANISM: Homo sapiens
<400> SEQUENCE: 7

| | |
|---|---|
| aggatacagc ggcttctgcg cgacttataa gagctccttg tgcggcgcca ttttaagcct | 60 |
| ctcggtctgt ggcagcagcg ttggcccggc cccgggagcg gagagcgagg ggaggcggag | 120 |
| acggaggaag gtctgaggag cagcttcagt ccccgccgag ccgccaccgc aggtcgagga | 180 |
| cggtcggact cccgcggcgg gaggagcctg ttcccctgag ggtatttgaa gtataccata | 240 |
| caactgtttt gaaaatccag cgtggacaat ggctactcaa gctgatttga tggagttgga | 300 |
| catggccatg gaaccagaca gaaaagcggc tgttagtcac tggcagcaac agtcttacct | 360 |
| ggactctgga atccattctg gtgccactac cacagctcct tctctgagtg gtaaaggcaa | 420 |
| tcctgaggaa gaggatgtgg atacctccca gtcctgtat gagtgggaac agggattttc | 480 |
| tcagtccttc actcaagaac aagtagctga tattgatgga cagtatgcaa tgactcgagc | 540 |

```
tcagagggta cgagctgcta tgttccctga gacattagat gagggcatgc agatcccatc    600
tacacagttt gatgctgctc atcccactaa tgtccagcgt ttggctgaac catcacagat    660
gctgaaacat gcagttgtaa acttgattaa ctatcaagat gatgcagaac ttgccacacg    720
tgcaatccct gaactgacaa aactgctaaa tgacgaggac caggtggtgg ttaataaggc    780
tgcagttatg gtccatcagc tttctaaaaa ggaagcttcc agacacgcta tcatgcgttc    840
tcctcagatg tgtctgcta ttgtacgtac catgcagaat acaaatgatg tagaaacagc    900
tcgttgtacc gctgggacct tgcataacct ttcccatcat cgtgagggct tactggccat    960 cttttaagtct ggaggcattc ctgccctggt gaaaatgctt ggttcaccag tggattctgt   1020
gttgttttat gccattacaa ctctccacaa cctttattta catcaagaag gagctaaaat   1080
ggcagtgcgt ttagctggtg ggctgcagaa aatggttgcc ttgctcaaca aaacaaatgt   1140
taaattcttg gctattacga cagactgcct tcaaatttta gcttatggca accaagaaag   1200
caagctcatc atactggcta gtggtggacc ccaagcttta gtaaatataa tgaggaccta   1260
tacttacgaa aaactactgt ggaccacaag cagagtgctg aaggtgctat ctgtctgctc   1320
tagtaataag ccggctattg tagaagctgg tggaatgcaa gctttaggac ttcacctgac   1380
agatccaagt caacgtcttg ttcagaactg tctttggact ctcaggaatc tttcagatgc   1440
tgcaactaaa caggaaggga tggaaggtct ccttgggact cttgttcagc ttctgggttc   1500
agatgatata aatgtggtca cctgtgcagc tggaattctt tctaacctca cttgcaataa   1560
ttataagaac aagatgatgg tctgccaagt gggtggtata gaggctcttg tgcgtactgt   1620
ccttcgggct ggtgacaggg aagacatcac tgagcctgcc atctgtgctc ttcgtcatct   1680
gaccagccga caccaagaag cagagatggc ccagaatgca gttcgccttc actatggact   1740
accagttgtg gttaagctct tacacccacc atcccactgg cctctgataa aggctactgt   1800
tggattgatt cgaaatcttg cccttttgtcc cgcaaatcat gcacctttgc gtgagcaggg   1860
tgccattcca cgactagttc agttgcttgt tcgtgcacat caggataccc agcgccgtac   1920
gtccatgggt gggacacagc agcaatttgt ggaggggtc cgcatggaag aaatagttga   1980
aggttgtacc ggagcccttc acatcctagc tcgggatgtt cacaaccgaa ttgttatcag   2040
aggactaaat accattccat gtttgtgca gctgctttat tctcccattg aaaacatcca   2100
aagagtagct gcaggggtcc tctgtgaact tgctcaggac aaggaagctg cagaagctat   2160
tgaagctgag ggagccacag ctcctctgac agagttactt cactctagga atgaaggtgt   2220
ggcgacatat gcagctgctg tttttgttccg aatgtctgag acaagccac aagattacaa   2280 gaaacggctt tcagttgagc tgaccagctc tctcttcaga acagagccaa tggcttggaa   2340
tgagactgct gatcttggac ttgatattgg tgcccaggga gaaccccttg gatatcgcca   2400
ggatgatcct agctatcgtt cttttcactc tggtggatat ggccaggatg ccttgggtat   2460
ggaccccatg atggaacatg agatgggtgg ccaccaccct ggtgctgact atccagttga   2520
tgggctgcca gatctggggc atgcccagga cctcatggat gggctgcctc caggtgacag   2580
caatcagctg gcctggtttg atactgacct gtaaatcatc ctttaggtaa aagttttaa   2640 aaagccagtt tgggtaaaat actttactc tgcctacaga acttcagaaa gacttggttg   2700
gtagggtggg agtggtttag gtatttgta aatctgccac aaaaacaggt atatactttg   2760
aaaggagatg tcttggaaca ttggaatgtt ctcagattc tggttgttat gtgatcatgt   2820
gtggaagtta ttaactttaa tgttttttgc cacagctttt gcaacttaat actcaaatga   2880
gtaacatttg ctgtttttaaa cattaatagc agcctttctc tctttataca gctgtattgt   2940
```

| | |
|---|---:|
| ctgaacttgc attgtgattg gcctgtagag ttgctgagag ggctcgaggg gtgggctggt | 3000 |
| atctcagaaa gtgcctgaca cactaaccaa gctgagtttc ctatgggaac aattgaagta | 3060 |
| aacttttgt tctggtcctt tttggtcgag gagtaacaat acaaatggat tttgggagtg | 3120 |
| actcaagaag tgaagaatgc acaagaatgg atcacaagat ggaatttatc aaaccctagc | 3180 |
| cttgcttgtt aaattttttt ttttttttt ttaagaatat ctgtaatggt actgactttg | 3240 |
| cttgctttga gtagctctt tttttttttt ttttttttt tttgcagtaa ctgttttta | 3300 |
| agtctctcgt agtgttaagt tatagtgaat actgctacag caatttctaa tttttaagaa | 3360 |
| ttgagtaatg gtgtagaaca ctaattcata atcactctaa ttaattgtaa tctgaataaa | 3420 |
| gtgtaacaat tgtgtagcct ttttgtataa aatagacaaa tagaaaatgg tccaattagt | 3480 |
| ttccttttta atatgcttaa aataagcagg tggatctatt tcatgttttt gatcaaaaac | 3540 |
| tatttgggat atgtatgggt agggtaaatc agtaagaggt gttatttgga accttgtttt | 3600 |
| ggacagttta ccagttgcct tttatcccaa agttgttgta acctgctgtg atacgatgct | 3660 |
| tcaagagaaa atgcggttat aaaaaatggt tcagaattaa acttttaatt cattcgattg | 3720 |

<210> SEQ ID NO 8
<211> LENGTH: 2339
<212> TYPE: DNA
<213> ORGANISM: Homo sapiens

<400> SEQUENCE: 8

| | |
|---|---:|
| cctgtggtcc cgggtttctg cagagtctac ttcagaagcg gaggcactgg gagtccggtt | 60 |
| tgggattgcc aggctgtggt tgtgagtctg agcttgtgag cggctgtggc gccccaactc | 120 |
| ttcgccagca tatcatcccg gcaggcgata aactacattc agttgagtct gcaagactgg | 180 |
| gaggaactgg ggtgataaga aatctattca ctgtcaaggt ttattgaagt caaaatgtcc | 240 |
| aaaaaaatca gtggcggttc tgtggtagag atgcaaggag atgaaatgac acgaatcatt | 300 |
| tgggaattga ttaaagagaa actcattttt ccctacgtgg aattggatct acatagctat | 360 |
| gatttaggca tagagaatcg tgatgccacc aacgaccaag tcaccaagga tgctgcagaa | 420 |
| gctataaaga agcataatgt tggcgtcaaa tgtgccacta tcactcctga tgagaagagg | 480 |
| gttgaggagt tcaagttgaa acaaatgtgg aaatcaccaa atggcaccat cgaaatatt | 540 |
| ctgggtggca cggtcttcag agaagccatt atctgcaaaa atatccccg gcttgtgagt | 600 |
| ggatgggtaa aacctatcat cataggtcgt catgcttatg gggatcaata cagagcaact | 660 |
| gattttgttg ttcctgggcc tggaaaagta gagataaacct acacaccaag tgacggaacc | 720 |
| caaaaggtga catacctggt acataacttt gaagaaggtg gtggtgttgc catggggatg | 780 |
| tataatcaag ataagtcaat tgaagatttt gcacacagtt ccttccaaat ggctctgtct | 840 |
| aagggttggc ctttgtatct gagcaccaaa aacactattc tgaagaaata tgatgggcgt | 900 |
| tttaaagaca tctttcagga gatatatgac aagcagtaca agtcccagtt tgaagctcaa | 960 |
| aagatctggt atgagcatag gctcatcgac gacatggtgg cccaagctat gaaatcagag | 1020 |
| ggaggcttca tctgggcctg taaaaactat gatggtgacg tgcagtcgga ctctgtggcc | 1080 |
| caagggtatg gctctctcgg catgatgacc agcgtgctgg tttgtccaga tggcaagaca | 1140 |
| gtagaagcag aggctgccca cgggactgta acccgtcact accgcatgta ccagaaagga | 1200 |
| caggagacgt ccaccaatcc cattgcttcc atttttgcct ggaccagagg gttagcccac | 1260 |
| agagcaaagc ttgataacaa taagagctt gccttctttg caaatgcttt ggaagaagtc | 1320 |
| tctattgaga caattgaggc tggcttcatg accaaggact tggctgcttg cattaaaggt | 1380 |

```
ttacccaatg tgcaacgttc tgactacttg aatacatttg agttcatgga taaacttgga    1440
gaaaacttga agatcaaact agctcaggcc aaactttaag ttcatacctg agctaagaag    1500
gataattgtc ttttggtaac taggtctaca ggtttacatt tttctgtgtt acactcaagg    1560
ataaaggcaa aatcaatttt gtaatttgtt tagaagccag agtttatctt ttctataagt    1620
ttacagcctt tttcttatat atacagttat tgccacctttt gtgaacatgg caagggactt   1680
ttttacaatt tttattttat tttcagtac cagcctagga attcggttag tactcatttg     1740
tattcactgt cactttttct catgttctaa ttataaatga ccaaaatcaa gattgctcaa    1800
aagggtaaat gatagccaca gtattgctcc ctaaaatatg cataaagtag aaattcactg    1860
ccttcccctc ctgtccatga ccttgggcac agggaagttc tggtgtcata gatatcccgt    1920
tttgtgaggt agagctgtgc attaaacttg cacatgactg gaacgaagta tgagtgcaac    1980
tcaaatgtgt tgaagatact gcagtcattt ttgtaaagac cttgctgaat gtttccaata    2040
gactaaatac tgtttaggcc gcaggagagt ttggaatccg gaataaatac tacctggagg    2100
tttgtcctct ccattttct ctttctcctc ctggcctggc ctgaatatta tactactcta     2160
aatagcatat ttcatccaag tgcaataatg taagctgaat cttttttgga cttctgctgg    2220
cctgttttat ttcttttata taaatgtgat ttctcagaaa ttgatattaa acactatctt    2280
atcttctcct gaactgttga ttttaattaa aattaagtgc taattaccaa aaaaaaaaa     2339
```

<210> SEQ ID NO 9
<211> LENGTH: 1740
<212> TYPE: DNA
<213> ORGANISM: Homo sapiens

<400> SEQUENCE: 9

```
ccagcgttag cccgcggcca ggcagccggg aggagcggcg cgcgctcgga cctctcccgc      60
cctgctcgtt cgctctccag cttgggatgg ccggctacct gcgggtcgtg cgctcgctct     120
gcagagcctc aggctcgcgg ccggcctggg cgccggcggc cctgacagcc cccacctcgc     180
aagagcagcc gcggcgccac tatgccgaca aaaggatcaa ggtggcgaag cccgtggtgg     240
agatggatgg tgatgagatg acccgtatta tctggcagtt catcaaggag aagctcatcc     300
tgccccacgt ggacatccag ctaaagtatt ttgacctcgg gctcccaaac cgtgaccaga     360
ctgatgacca ggtcaccatt gactctgcac tggccaccca gaagtacagt gtggctgtca     420
agtgtgccac catcaccct gatgaggccc gtgtggaaga gttcaagctg aagaagatgt      480
ggaaaagtcc caatggaact atccggaaca tcctgggggg gactgtcttc cgggagccca     540
tcatctgcaa aaacatccca cgcctagtcc ctggctggac caagcccatc accattggca     600
ggcacgccca tggcgaccag tacaaggcca cagactttgt ggcagaccgg ccggcacttt     660
tcaaaatggt cttcaccca aaagatggca gtggtgtcaa ggagtgggaa gtgtacaact     720
tccccgcagg cggcgtgggc atgggcatgt acaacaccga cgagtccatc tcaggttttg      780
cgcacagctg cttccagtat gccatccaga agaaatggcc gctgtacatg agcaccaaga     840
acaccatact gaaagcctac gatgggcgtt tcaaggacat cttccaggag atctttgaca     900
agcactataa gaccgacttc gacaagaata agatctggta tgagcaccgg ctcattgatg     960
acatggtggc tcaggtcctc aagtcttcgg gtggctttgt gtgggcctgc aagaactatg    1020
acggagatgt gcagtcagac atcctggccc agggctttgg ctcccttggc ctgatgacgt    1080
ccgtcctggt ctgccctgat gggaagacga ttgaggctga ggccgctcat gggaccgtca    1140
cccgccacta tcgggagcac cagaagggcc ggcccaccag caccaacccc atcgccagca    1200
```

```
tctttgcctg gacacgtggc ctggagcacc gggggaagct ggatgggaac caagacctca    1260
tcaggtttgc ccagatgctg gagaaggtgt gcgtggagac ggtggagagt ggagccatga    1320
ccaaggacct ggcgggctgc attcacggcc tcagcaatgt gaagctgaac gagcacttcc    1380
tgaacaccac ggacttcctc gacaccatca gagcaacct ggacagagcc ctgggcaggc     1440
agtaggggga ggcgccaccc atggctgcag tggaggggcc agggctgagc cggcgggtcc    1500
tcctgagcgc ggcagagggt gagcctcaca gcccctctct ggaggccttt ctaggggatg    1560
tttttttata agccagatgt ttttaaaagc atatgtgtgt ttcccctcat ggtgacgtga    1620
ggcaggagca gtgcgtttta cctcagccag tcagtatgtt ttgcatactg taatttatat    1680
tgcccttgga acacatggtg ccatatttag ctactaaaaa gctcttcaca aaaaaaaaaa    1740
```

<210> SEQ ID NO 10
<211> LENGTH: 4454
<212> TYPE: DNA
<213> ORGANISM: Homo sapiens

<400> SEQUENCE: 10

```
gaaacgtccc gtgtgggagg ggcgggtctg ggtgcggcct gccgcatgac tcgtggttcg      60
gaggcccacg tggccggggc ggggactcag gcgcctgggg cgccgactga ttacgtagcg     120
ggcggggccg gaagtgccgc tccttggtgg gggctgttca tggcggttcc ggggtctcca    180
acatttttcc cggctgtggt cctaaatctg tccaaagcag aggcagtgga gcttgaggtt    240
cttgctggtg tgaaatgact gagtacaaac tggtggtggt tggagcaggt ggtgttggga    300
aaagcgcact gacaatccag ctaatccaga accactttgt agatgaatat gatcccacca    360
tagaggattc ttacagaaaa caagtggtta tagatggtga aacctgtttg ttggacatac    420
tggatacagc tggacaagaa gagtacagtg ccatgagaga ccaatacatg aggacaggcg    480
aaggcttcct ctgtgtattt gccatcaata atagcaagtc atttgcggat attaacctct    540
acagggagca gattaagcga gtaaaagact cggatgatgt acctatggtg ctagtgggaa    600
acaagtgtga tttgccaaca aggacagttg atacaaaaca agcccacgaa ctggccaaga    660
gttacgggat tccattcatt gaaacctcag ccaagaccag acagggtgtt gaagatgctt    720
tttacacact ggtaagagaa atacgccagt accgaatgaa aaaactcaac agcagtgatg    780
atgggactca gggttgtatg ggattgccat gtgtggtgat gtaacaagat acttttaaag    840
ttttgtcaga aaagagccac tttcaagctg cactgacacc ctggtcctga cttccctgga    900
ggagaagtat tcctgttgct gtcttcagtc tcacagagaa gctcctgcta cttccccagc    960
tctcagtagt ttagtacaat aatctctatt tgagaagttc tcagaataac tacctcctca   1020
cttggctgtc tgaccagaga atgcacctct tgttactccc tgttattttt ctgccctggg   1080
ttcttccaca gcacaaacac acctctgcca ccccaggttt tcatctgaa aagcagttca    1140 tgtctgaaac agagaaccaa accgcaaacg tgaaattcta ttgaaaacag tgtcttgagc   1200
tctaaagtag caactgctgg tgatttttttt tttctttta ctgttgaact agaactatg    1260 ctaattttg gagaaatgtc ataaattact gttttgccaa gaatatagtt attattgctg    1320
tttggtttgt ttataatgtt atcggctcta ttctctaaac tggcatctgc tctagattca   1380
taaatacaaa aatgaatact gaattttgag tctatcctag tcttcacaac tttgacgtaa   1440
ttaaatccaa ctttcacagt gaagtgcctt tttcctagaa gtggtttgta gacttccttt    1500
ataatatttc agtggaatag atgtctcaaa aatccttatg catgaaatga atgtctgaga   1560
tacgtctgtg acttatctac cattgaagga aagctatatc tatttgagag cagatgccat   1620
```

```
tttgtacatg tatgaaattg gttttccaga ggcctgtttt ggggctttcc caggagaaag    1680
atgaaactga aagcacatga ataatttcac ttaataattt ttacctaatc tccactttt    1740
tcataggtta ctacctatac aatgtatgta atttgtttcc cctagcttac tgataaacct    1800
aatattcaat gaacttccat ttgtattcaa atttgtgtca taccagaaag ctctacattt    1860
gcagatgttc aaatattgta aaactttggt gcattgttat ttaatagctg tgatcagtga    1920
ttttcaaacc tcaaatatag tatattaaca aattacatttt tcactgtata tcatggtatc    1980
ttaatgatgt atataattgc cttcaatccc cttctcaccc caccctctac agcttccccc    2040
acagcaatag gggcttgatt atttcagttg agtaaagcat ggtgctaatg gaccagggtc    2100
acagtttcaa aacttgaaca atccagttag catcacagag aaagaaattc ttctgcattt    2160
gctcattgca ccagtaactc cagctagtaa ttttgctagg tagctgcagt tagccctgca    2220
aggaaagaag aggtcagtta gcacaaaccc tttaccatga ctggaaaact cagtatcacg    2280
tatttaaaca tttttttttc ttttagccat gtagaaactc taaattaagc caatattctc    2340
atttgagaat gaggatgtct cagctgagaa acgttttaaa ttctctttat tcataatgtt    2400
ctttgaaggg tttaaaacaa gatgttgata aatctaagct gatgagtttg ctcaaaacag    2460
gaagttgaaa ttgttgagac aggaatggaa aatataatta attgatacct atgaggattt    2520
ggaggcttgg cattttaatt tgcagataat accctggtaa ttctcatgaa aaatagactt    2580
ggataacttt tgataaaaga ctaattccaa aatggccact ttgttcctgt ctttaatatc    2640
taaatactta ctgaggtcct ccatcttcta tattatgaat tttcatttat taagcaaatg    2700
tcatattacc ttgaaattca gaagagaaga acatatact gtgtccagag tataatgaac    2760
ctgcagagtt gtgcttctta ctgctaattc tgggagcttt cacagtactg tcatcatttg    2820
taaatggaaa ttctgctttt ctgtttctgc tccttctgga gcagtgctac tctgtaattt    2880
tcctgaggct tatcacctca gtcatttctt ttttaaatgt ctgtgactgg cagtgattct    2940
ttttcttaaa aatctattaa atttgatgtc aaattaggga gaaagatagt tactcatctt    3000
gggctcttgt gccaatagcc cttgtatgta tgtacttaga gttttccaag tatgttctaa    3060
gcacagaagt ttctaaatgg ggccaaaatt cagacttgag tatgttcttt gaatacctta    3120
agaagttaca attagccggg catggtggcc cgtgcctgta gtcccagcta cttgagaggc    3180
tgaggcagga gaatcacttc aacccaggag gtggaggtta cagtgagcag agatcgtgcc    3240
actgcactcc agcctgggtg acaagagaga cttgtctcca aaaaaaagt tacacctagg    3300
tgtgaatttt ggcacaaagg agtgacaaac ttatagttaa aagctgaata acttcagtgt    3360
ggtataaaac gtggttttta ggctatgttt gtgattgctg aaaagaattc tagtttacct    3420
caaaatcctt ctctttcccc aaattaagtg cctggccagc tgtcataaat tacatattcc    3480
ttttggtttt tttaaaggtt acatgttcaa gagtgaaaat aagatgttct gtctgaaggc    3540
taccatgccg gatctgtaaa tgaacctgtt aaatgctgta tttgctccaa cggcttacta    3600
tagaatgtta cttaatacaa tatcatactt attacaattt ttactatagg agtgtaatag    3660
gtaaaattaa tctctatttt agtgggccca tgtttagtct ttcaccatcc tttaaactgc    3720
tgtgaatttt tttgtcatga cttgaaagca aggatagaa aacactttag agatatgtgg    3780
ggttttttta ccattccaga gcttgtgagc ataatcatat ttgctttata tttatagtca    3840
tgaactccta agttggcagc tacaaccaag aaccaaaaaa tggtgcgttc tgcttcttgt    3900
aattcatctc tgctaataaa ttataagaag caaggaaaat tagggaaaat attttatttg    3960
gatggtttct ataaacaagg gactataatt cttgtacatt attttcatc tttgctgttt    4020
```

```
ctttgagcag tctaatgtgc cacacaatta tctaaggtat ttgttttcta taagaattgt    4080
tttaaaagta ttcttgttac cagagtagtt gtattatatt tcaaaacgta agatgatttt    4140
taaaagcctg agtactgacc taagatggaa ttgtatgaac tctgctctgg agggagggga    4200
ggatgtccgt ggaagttgta agacttttat tttttgtgc catcaaatat aggtaaaaat     4260
aattgtgcaa ttctgctgtt taaacaggaa ctattggcct ccttggccct aaatggaagg    4320
gccgatattt taagttgatt attttattgt aaattaatcc aacctagttc ttttaatttt    4380
ggttgaatgt ttttcttgt taaatgatgt ttaaaaaata aaaactggaa gttcttggct      4440
tagtcataat tctt                                                      4454
```

<210> SEQ ID NO 11
<211> LENGTH: 5572
<212> TYPE: DNA
<213> ORGANISM: Homo sapiens

<400> SEQUENCE: 11

```
cctcccctcg cccggcgcgg tcccgtccgc ctctcgctcg cctcccgcct ccctcggtc       60 ttccgaggcg cccgggctcc cggcgcggcg gcggaggggg cgggcaggcc ggcgggcgt     120 gatgtggcgg gactctttat gcgctgcggc aggatacgcg ctcggcgctg ggacgcgact     180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgc cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcgcggcgg cacctcccgc tcctggagcg gggggagaa gcggcggcg      540 cggcggccgc ggcggctgca gctccaggga gggggtctga gtcgcctgtc accatttcca    600
gggctgggaa cgccggagag ttggtctctc cccttctact gcctccaaca cggcggcggc    660
ggcggcggca catccaggga cccgggccgg ttttaaacct cccgtccgcc gccgccgcac    720
cccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
aagcggcggc agagcgaggg gcatcagcta ccgccaagtc cagagccatt tccatcctgc    960
agaagaagcc ccgccaccag cagcttctgc catctctctc ctccttttc ttcagccaca    1020 ggctcccaga catgacagcc atcatcaaag agatcgttag cagaaacaaa aggagatatc    1080
aagaggatgg attcgactta gacttgacct atatttatcc aaacattatt gctatgggat    1140
ttcctgcaga aagacttgaa ggcgtataca ggaacaatat tgatgatgta gtaaggtttt    1200
tggattcaaa gcataaaaac cattacaaga tatacaatct ttgtgctgaa agacattatg    1260
acaccgccaa atttaattgc agagttgcac aatatccttt tgaagaccat aacccaccac    1320
agctagaact tatcaaaccc ttttgtgaag atcttgacca atggctaagt gaagatgaca    1380
atcatgttgc agcaattcac tgtaaagctg gaaagggacg aactggtgta atgatatgtg    1440
catatttatt acatcggggc aaattttta aggcacaaga ggccctagat ttctatgggg    1500
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
agatgatgtt tgaaactatt ccaatgttca gtggcggaac ttgcaatcct cagtttgtgg    1680
```

```
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaaagt agaaaatgga agtctatgtg    1920
atcaagaaat cgatagcatt tgcagtatag agcgtgcaga taatgacaag gaatatctag    1980
tacttacttt aacaaaaaat gatcttgaca aagcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga acctttgat gaagatcagc    2220 atacacaaat tacaaaagtc tgaattttt tttatcaaga gggataaaac accatgaaaa    2280
taaacttgaa taaactgaaa atggaccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaggt tgtgtagctg tgtcatgtat    2460
ataccttttt gtgtcaaaag gacatttaaa attcaattag gattaataaa gatggcactt    2520
tcccgtttta ttcagttttt ataaaaagtg gagacagact gatgtgtata cgtaggaatt    2580 ttttccttt gtgttctgtc accaactgaa gtggctaaag gctttgtga tatactggtt    2640 cacatcctac ccctttgcac ttgtggcaac agataagttt gcagttggct aagagaggtt    2700
tccgaagggt tttgctacat tctaatgcat gtattcgggt taggggaatg gagggaatgc    2760
tcagaaagga aataattta tgctggactc tggaccatat accatctcca gctatttaca    2820
cacacctttc tttagcatgc tacagttatt aatctggaca ttcgaggaat tggccgctgt    2880
cactgcttgt tgttttgcgca ttttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tatttacta    3240 gttttcaatc ataatacctg ctgtggatgc ttcatgtgct gcctgcaagc ttctttttc    3300 tcattaaata taaaatattt tgtaatgctg cacagaaatt ttcaatttga gattctacag    3360
taagcgtttt tttctttga agatttatga tgcacttatt caatagctgt cagccgttcc    3420 accccttttga ccttacacat tctattacaa tgaattttgc agttttgcac atttttaaa    3480 tgtcattaac tgttagggaa ttttacttga atactgaata catataatgt ttatattaaa    3540
aaggacattt gtgttaaaaa ggaaattaga gttgcagtaa actttcaatg ctgcacacaa    3600 aaaaagaca tttgattttt cagtagaaat tgtcctacat gtgctttatt gatttgctat    3660
tgaaagaata gggttttttt ttttttttt tttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggttttt tttccagaaa tttggtgtct    3900
tcaaattata ccttcacctt gacatttgaa tatccagcca ttttgttct taatggtata    3960 aaattccatt ttcaataact tattggtgct gaaattgttc actagctgtg gtctgaccta    4020
gttaatttac aaatacagat tgaataggac ctactagagc agcatttata gagtttgatg    4080
```

```
gcaaatagat taggcagaac ttcatctaaa atattcttag taaataatgt tgacacgttt      4140
tccatacctt gtcagtttca ttcaacaatt tttaaatttt taacaaagct cttaggattt      4200
acacatttat atttaaacat tgatatatag agtattgatt gattgctcat aagttaaatt      4260
ggtaaagtta gagacaacta ttctaacacc tcaccattga aatttatatg ccaccttgtc      4320
tttcataaaa gctgaaaatt gttacctaaa atgaaaatca acttcatgtt ttgaagatag      4380 ttataaaatat tgttctttgt tacaatttcg ggcaccgcat attaaaacgt aactttattg      4440
ttccaatatg taacatggag ggccaggtca taaataatga cattataatg ggcttttgca      4500
ctgttattat ttttcctttg gaatgtgaag gtctgaatga gggttttgat ttgaatgtt       4560 tcaatgtttt tgagaagcct tgcttacatt ttatggtgta gtcattggaa atggaaaaat      4620
ggcattatat atattatata tataaatata tattatacat actctcctta ctttatttca     4680
gttaccatcc ccatagaatt tgacaagaat tgctatgact gaaaggtttt cgagtcctaa      4740
ttaaaacttt atttatggca gtattcataa ttagcctgaa atgcattctg taggtaatct      4800
ctgagttcct ggaatatttt cttagacttt ttggatgtgc agcagcttac atgtctgaag     4860
ttacttgaag gcatcacttt taagaaagct tacagttggg ccctgtacca tcccaagtcc     4920
tttgtagctc ctcttgaaca tgtttgccat acttttaaaa gggtagttga ataaatagca     4980
tcaccattct tgctgtggc acaggttata aacttaagtg gagtttaccg gcagcatcaa      5040
atgtttcagc tttaaaaaat aaaagtaggg tacaagttta atgtttagtt ctagaaattt     5100
tgtgcaatat gttcataacg atggctgtgg ttgccacaaa gtgcctcgtt tacctttaaa     5160
tactgttaat gtgtcatgca tgcagatgga aggggtggaa ctgtgcacta agtgggggc      5220 tttaactgta gtatttggca gagttgcctt ctacctgcca gttcaaaagt tcaacctgtt     5280
ttcatataga atatatatac taaaaaattt cagtctgtta aacagcctta ctctgattca     5340
gcctcttcag atactcttgt gctgtgcagc agtggctctg tgtgtaaatg ctatgcactg     5400
aggatacaca aaaataccaa tatgatgtgt acaggataat gcctcatccc aatcagatgt     5460
ccatttgtta ttgtgtttgt taacaaccct ttatctctta gtgttataaa ctccacttaa     5520
aactgattaa agtctcattc ttgtcaaaaa aaaaaaaaa aaaaaaaaa aa                5572
```

<210> SEQ ID NO 12
<211> LENGTH: 2591
<212> TYPE: DNA
<213> ORGANISM: Homo sapiens

<400> SEQUENCE: 12

```
gatgggattg gggttttccc ctcccatgtg ctcaagactg gcgctaaaag ttttgagctt       60
ctcaaaagtc tagagccacc gtccagggag caggtagctg ctgggctccg ggacacttt       120 gcgttcgggc tgggagcgtg cttttccacga cggtgacacg cttccctgga ttggcagcca     180
gactgccttc cgggtcactg ccatggagga gccgcagtca gatcctagcg tcgagccccc     240
tctgagtcag gaaacatttt cagacctatg gaaactactt cctgaaaaca acgttctgtc     300
ccccttgccg tcccaagcaa tggatgattt gatgctgtcc ccggacgata ttgaacaatg     360
gttcactgaa gacccaggtc cagatgaagc tcccagaatg ccagaggctg ctcccccgt     420 ggcccctgca ccagcagctc ctacaccggc ggcccctgca ccagccccct cctggcccct     480
gtcatcttct gtcccttccc agaaaaccta ccagggcagc tacggtttcc gtctgggctt     540
cttgcattct gggacagcca agtctgtgac ttgcacgtac tcccctgccc tcaacaagat     600
gttttgccaa ctggccaaga cctgccctgt gcagctgtgg gttgattcca caccccgcc     660
```

| | |
|---|---|
| cggcacccgc gtccgcgcca tgccatctca caagcagtca cagcacatga cggaggttgt | 720 |
| gaggcgctgc ccccaccatg agcgctgctc agatagcgat ggtctggccc ctcctcagca | 780 |
| tcttatccga gtggaaggaa atttgcgtgt ggagtatttg gatgacagaa acacttttcg | 840 |
| acatagtgtg gtggtgccct atgagccgcc tgaggttggc tctgactgta ccaccatcca | 900 |
| ctacaactac atgtgtaaca gttcctgcat gggcggcatg aaccggaggc ccatcctcac | 960 |
| catcatcaca ctggaagact ccagtggtaa tctactggga cggaacagct ttgaggtgcg | 1020 |
| tgtttgtgcc tgtcctggga gagaccggcg cacagaggaa gagaatctcc gcaagaaagg | 1080 |
| ggagcctcac cacgagctgc cccaggggag cactaagcga gcactgccca acaacaccag | 1140 |
| ctcctctccc cagccaaaga gaaaccact ggatggagaa tatttcaccc ttcagatccg | 1200 |
| tgggcgtgag cgcttcgaga tgttccgaga gctgaatgag gccttggaac tcaaggatgc | 1260 |
| ccaggctggg aaggagccag gggggagcag ggctcactcc agccacctga agtccaaaaa | 1320 |
| gggtcagtct acctcccgcc ataaaaaact catgttcaag acagaagggc ctgactcaga | 1380 |
| ctgacattct ccacttcttg ttccccactg acagcctccc accccatct ctccctcccc | 1440 |
| tgccattttg ggtttgggt ctttgaaccc ttgcttgcaa taggtgtgcg tcagaagcac | 1500 |
| ccaggacttc catttgcttt gtcccggggc tccactgaac aagttggcct gcactggtgt | 1560 |
| tttgttgtgg ggaggaggat ggggagtagg ataccagc ttagatttta aggttttac | 1620 |
| tgtgagggat gtttgggaga tgtaagaaat gttcttgcag ttaagggtta gtttacaatc | 1680 |
| agccacattc taggtagggg cccacttcac cgtactaacc agggaagctg tccctcactg | 1740 |
| ttgaattttc tctaacttca aggcccatat ctgtgaaatg ctggcatttg cacctacctc | 1800 |
| acagagtgca ttgtgagggt taatgaaata atgtacatct ggccttgaaa ccaccttta | 1860 |
| ttacatgggg tctagaactt gacccccttg agggtgcttg ttccctctcc ctgttggtcg | 1920 |
| gtgggttggt agtttctaca gttgggcagc tggttaggta gagggagttg tcaagtctct | 1980 |
| gctggcccag ccaaaccctg tctgacaacc tcttggtgaa ccttagtacc taaaaggaaa | 2040 |
| tctcacccca tcccacaccc tggaggattt catctcttgt atatgatgat ctggatccac | 2100 |
| caagacttgt tttatgctca gggtcaattt ctttttttctt ttttttttttt ttttttcttt | 2160 |
| ttctttgaga ctgggtctcg ctttgttgcc caggctggag tggagtggcg tgatcttggc | 2220 |
| ttactgcagc ctttgcctcc ccggctcgag cagtcctgcc tcagcctccg gagtagctgg | 2280 |
| gaccacaggt tcatgccacc atggccagcc aacttttgca tgttttgtag agatggggtc | 2340 |
| tcacagtgtt gcccaggctg gtctcaaact cctgggctca ggcgatccac ctgtctcagc | 2400 |
| ctcccagagt gctgggatta caattgtgag ccaccacgtc cagctggaag ggtcaacatc | 2460 |
| ttttacattc tgcaagcaca tctgcatttt caccccaccc ttcccctcct tctcccttt | 2520 |
| tatatcccat ttttatatcg atctcttatt ttacaataaa actttgctgc cacctgtgtg | 2580 |
| tctgaggggt g | 2591 |

<210> SEQ ID NO 13
<211> LENGTH: 6574
<212> TYPE: DNA
<213> ORGANISM: Homo sapiens

<400> SEQUENCE: 13

| | |
|---|---|
| aagagcaaaa agcgaaggcg caatctggac actgggagat tcggagcgca gggagtttga | 60 |
| gagaaacttt tattttgaag agaccaaggt tgagggggggg cttatttcct gacagctatt | 120 |
| tacttagagc aaatgattag ttttagaagg atggactata acattgaatc aattacaaaa | 180 |

```
cgcggttttt gagcccatta ctgttggagc tacagggaga gaaacagagg aggagactgc    240
aagagatcat tggaggccgt gggcacgctc tttactccat gtgtgggaca ttcattgcgg    300
aataacatcg gaggagaagt tcccagagc tatggggact tcccatccgg cgttcctggt     360
cttaggctgt cttctcacag ggctgagcct aatcctctgc cagctttcat taccctctat    420
ccttccaaat gaaaatgaaa aggttgtgca gctgaattca tccttttctc tgagatgctt    480
tggggagagt gaagtgagct ggcagtaccc catgtctgaa gagagagct ccgatgtgga     540 aatcagaaat gaagaaaaca acagcggcct ttttgtgacg gtcttggaag tgagcagtgc    600
ctcggcggcc cacacagggt tgtacacttg ctattacaac cacactcaga cagaagagaa    660
tgagcttgaa ggcaggcaca tttacatcta tgtgccagac ccagatgtag cctttgtacc    720
tctaggaatg acggattatt tagtcatcgt ggaggatgat gattctgcca ttataccttg    780
tcgcacaact gatcccgaga ctcctgtaac cttacacaac agtgagggg tggtacctgc     840 ctcctacgac agcagacagg gctttaatgg gaccttcact gtagggccct atatctgtga    900
ggccaccgtc aaaggaaaga agttccgac catcccattt aatgtttatg ctttaaaagc     960
aacatcagag ctggatctag aaatggaagc tcttaaaacc gtgtataagt caggggaaac   1020
gattgtggtc acctgtgctg ttttttaacaa tgaggtggtt gaccttcaat ggacttaccc   1080
tggagaagtg aaaggcaaag gcatcacaat gctggaagaa atcaaagtcc catccatcaa   1140
attggtgtac actttgacgg tccccgaggc cacggtgaaa acagtggag attacgaatg    1200 tgctgcccgc caggctacca gggaggtcaa agaaatgaag aaagtcacta tttctgtcca   1260
tgagaaaggt ttcattgaaa tcaaacccac cttcagccag ttggaagctg tcaacctgca   1320
tgaagtcaaa catttttgttg tagaggtgcg ggcctaccca cctcccagga tatcctggct   1380
gaaaaacaat ctgactctga ttgaaaaatct cactgagatc accactgatg tggaaaagat   1440
tcaggaaata aggtatcgaa gcaaattaaa gctgatccgt gctaaggaag aagacagtgg   1500
ccattatact attgtagctc aaaatgaaga tgctgtgaag agctatactt ttgaactgtt   1560
aactcaagtt ccttcatcca ttctggactt ggtcgatgat caccatggct caactggggg   1620
acagacggtg aggtgcacag ctgaaggcac gccgcttcct gatattgagt ggatgatatg   1680
caaagatatt aagaaatgta ataatgaaac ttcctggact attttggcca acaatgtctc   1740
aaacatcatc acggagatcc actcccgaga caggagtacc gtggagggcc gtgtgacttt   1800
cgccaaagtg gaggagacca tcgccgtgcg atgcctggct aagaatctcc ttggagctga   1860
gaaccgagag ctgaagctgg tggctcccac cctgcgttct gaactcacgg tggctgctgc   1920
agtcctggtg ctgttggtga ttgtgatcat ctcacttatt gtcctggttg tcatttggaa   1980
acagaaaccg aggtatgaaa ttcgctggag ggtcattgaa tcaatcagcc cagatggaca   2040
tgaatatatt tatgtggacc cgatgcagct gccttatgac tcaagatggg agtttccaag   2100
agatggacta gtgcttggtc gggtcttggg gtctggagcg tttgggaagg tggttgaagg   2160
aacagcctat ggattaagcc ggtcccaacc tgtcatgaaa gttgcagtga agatgctaaa   2220
acccacggcc agatccagtg aaaaacaagc tctcatgtct gaactgaaga taatgactca   2280
cctggggcca catttgaaca ttgtaaactt gctgggagcc tgcaccaagt caggcccat    2340 ttacatcatc acagagtatt gcttctatgg agatttggtc aactatttgc ataagaatag   2400
ggatagcttc ctgagccacc acccagagaa gccaaagaaa gagctggata tctttggatt   2460
gaaccctgct gatgaaagca cacggagcta tgttatttta tcttttgaaa caatggtgaa   2520
ctacatggac atgaagcagg ctgatactac acagtatgtc cccatgctag aaaggaaaga   2580
```

```
ggtttctaaa tattccgaca tccagagatc actctatgat cgtccagcct catataagaa    2640
gaaatctatg ttagactcag aagtcaaaaa cctcctttca gatgataact cagaaggcct    2700
tactttattg gatttgttga gcttcaccta tcaagttgcc cgaggaatgg agtttttggc    2760
ttcaaaaaat tgtgtccacc gtgatctggc tgctcgcaac gtcctcctgg cacaaggaaa    2820
aattgtgaag atctgtgact ttggcctggc cagagacatc atgcatgatt cgaactatgt    2880
gtcgaaaggc agtacctttc tgcccgtgaa gtggatggct cctgagagca tctttgacaa    2940
cctctacacc acactgagtg atgtctggtc ttatggcatt ctgctctggg agatcttttc    3000
ccttggtggc accccttacc ccggcatgat ggtggattct actttctaca ataagatcaa    3060
gagtgggtac cggatggcca agcctgacca cgctaccagt gaagtctacg agatcatggt    3120
gaaatgctgg aacagtgagc cggagaagag accctccttt taccacctga gtgagattgt    3180
ggagaatctg ctgcctggac aatataaaaa gagttatgaa aaaattcacc tggacttcct    3240
gaagagtgac catcctgctg tggcacgcat gcgtgtggac tcagacaatg catacattgg    3300
tgtcacctac aaaaacgagg aagacaagct gaaggactgg gagggtggtc tggatgagca    3360
gagactgagc gctgacagtg gctacatcat tcctctgcct gacattgacc ctgtccctga    3420
ggaggaggac ctgggcaaga ggaacagaca cagctcgcag acctctgaag agagtgccat    3480
tgagacgggt tccagcagtt ccaccttcat caagagagag gacgagacca ttgaagacat    3540
cgacatgatg gatgacatcg gcatagactc ttcagacctg gtggaagaca gcttcctgta    3600
actggcggat tcgaggggtt ccttccactt ctggggccac ctctggatcc cgttcagaaa    3660
accactttat tgcaatgcag aggttgagag gaggacttgg ttgatgttta aagagaagtt    3720
cccagccaag ggcctcgggg agcgttctaa atatgaatga atgggatatt ttgaaatgaa    3780
ctttgtcagt gttgcctctt gcaatgcctc agtagcatct cagtggtgtg tgaagtttgg    3840
agatagatgg ataagggaat aataggccac agaaggtgaa cttttgtgctt caaggacatt    3900 ggtgagagtc caacagacac aatttatact gcgacagaac ttcagcattg taattatgta    3960
aataactcta accaaggctg tgtttagatt gtattaacta tcttctttgg acttctgaag    4020
agaccactca atccatccat gtacttccct cttgaaacct gatgtcagct gctgttgaac    4080 ttttttaaaga agtgcatgaa aaaccatttt tgaaccttaa aaggtactgg tactatagca    4140
ttttgctatc ttttttagtg ttaaagagat aaagaataat aattaaccaa ccttgtttaa    4200
tagatttggg tcatttagaa gcctgacaac tcattttcat attgtaatct atgtttataa    4260
tactactact gttatcagta atgctaaatg tgtaataatg taacatgatt tccctccaga    4320
gaaagcacaa tttaaaacaa tccttactaa gtaggtgatg agtttgacag ttttttgacat    4380 ttatattaaa taacatgttt ctctataaag tatggtaata gctttagtga attaaattta    4440
gttgagcata gagaacaaag taaaagtagt gttgtccagg aagtcagaat ttttaactgt    4500
actgaatagg ttccccaatc catcgtatta aaaacaatt aactgccctc tgaaataatg    4560
ggattagaaa caaacaaaac tcttaagtcc taaaagttct caatgtagag cataaacct    4620 gtgctgaaca taacttctca tgtatattac ccaatggaaa atataatgat cagcaaaaag    4680
actggatttg cagaagtttt tttttttttt ttcttcatgc ctgatgaaag ctttggcgac    4740
cccaatatat gtattttttg aatctatgaa cctgaaaagg gtcagaagga tgcccagaca    4800
tcagcctcct tcttcaccc cttaccccaa agagaaagag tttgaaactc gagaccataa    4860
agatattctt tagtggaggc tggatgtgca ttagcctgga tcctcagttc tcaaatgtgt    4920
gtggcagcca ggatgactag atcctggggtt tccatccttg agattctgaa gtatgaagtc    4980
```

```
tgagggaaac cagagtctgt attttttctaa actccctggc tgttctgatc ggccagtttt      5040
cggaaacact gacttaggtt tcaggaagtt gccatgggaa acaaataatt tgaactttgg      5100
aacagggttg gcattcaacc acgcaggaag cctactattt aaatccttgg cttcaggtta      5160
gtgacattta atgccatcta gctagcaatt gcgaccttaa tttaactttc cagtcttagc      5220
tgaggctgag aaagctaaag tttggttttg acaggttttc caaaagtaaa gatgctactt      5280
cccactgtat gggggagatt gaactttccc cgtctcccgt cttctgcctc ccactccata      5340
ccccgccaag gaaaggcatg tacaaaaatt atgcaattca gtgttccaag tctctgtgta      5400
accagctcag tgttttggtg gaaaaaacat tttaagtttt actgataatt tgaggttaga      5460
tgggaggatg aattgtcaca tctatccaca ctgtcaaaca ggttggtgtg ggttcattgg      5520
cattctttgc aatactgctt aattgctgat accatatgaa tgaaacatgg gctgtgatta      5580
ctgcaatcac tgtgctatcg gcagatgatg ctttggaaga tgcagaagca ataataaagt      5640
acttgactac ctactggtgt aatctcaatg caagccccaa ctttcttatc caactttttc      5700
atagtaagtg cgaagactga gccagattgg ccaattaaaa acgaaaacct gactaggttc      5760
tgtagagcca attagacttg aaatacgttt gtgtttctag aatcacagct caagcattct      5820
gtttatcgct cactctccct tgtacagcct tattttgttg gtgctttgca ttttgatatt      5880
gctgtgagcc ttgcatgaca tcatgaggcc ggatgaaact tctcagtcca gcagtttcca      5940
gtcctaacaa atgctcccac ctgaatttgt atatgactgc atttgtgtgt gtgtgtgtgt      6000
tttcagcaaa ttccagattt gtttccttttt ggcctcctgc aaagtctcca gaagaaaatt      6060
tgccaatctt tcctactttc tatttttatg atgacaatca aagccggcct gagaaacact      6120
atttgtgact ttttaaacga ttagtgatgt ccttaaaatg tggtctgcca atctgtacaa      6180
aatggtccta ttttttgtgaa gagggacata agataaaatg atgttataca tcaatatgta      6240
tatatgtatt tctatataga cttggagaat actgccaaaa catttatgac aagctgtatc      6300
actgccttcg tttatatttt tttaactgtg ataatcccca caggcacatt aactgttgca      6360
cttttgaatg tccaaaattt atatttaga aataataaaa agaaagatac ttacatgttc      6420
ccaaaacaat ggtgtggtga atgtgtgaga aaaactaact tgatagggtc taccaataca      6480
aaatgtatta cgaatgcccc tgttcatgtt tttgttttaa aacgtgtaaa tgaagatctt      6540
tatatttcaa taaatgatat ataatttaaa gtta      6574
```

<210> SEQ ID NO 14
<211> LENGTH: 1443
<212> TYPE: DNA
<213> ORGANISM: Homo sapiens

<400> SEQUENCE: 14

```
atgagcgacg tggctattgt gaaggagggt tggctgcaca acgagggga gtacatcaag       60 acctggcggc cacgctactt cctcctcaag aatgatggca ccttcattgg ctacaaggag      120
cggccgcagg atgtggacca acgtgaggct cccctcaaca acttctctgt ggcgcagtgc      180
cagctgatga agacggagcg gccccggccc aacaccttca tcatccgctg cctgcagtgg      240
accactgtca tcgaacgcac cttccatgtg gagactcctg aggagcggga ggagtggaca      300
accgccatcc agactgtggc tgacggcctc aagaagcagg aggaggagga gatggacttc      360
cggtcgggct cacccagtga caactcaggg gctgaagaga tggaggtgtc cctggccaag      420
cccaagcacc gcgtgaccat gaacgagttt gagtacctga agctgctggg caagggcact      480
ttcggcaagg tgatcctggt gaaggagaag gccacaggcc gctactacgc catgaagatc      540
```

| | | |
|---|---|---|
| ctcaagaagg aagtcatcgt ggccaaggac gaggtggccc acacactcac cgagaaccgc | 600 | |
| gtcctgcaga actccaggca ccccttcctc acagccctga agtactcttt ccagacccac | 660 | |
| gaccgcctct gctttgtcat ggagtacgcc aacgggggcg agctgttctt ccacctgtcc | 720 | |
| cgggagcgtg tgttctccga ggaccgggcc cgcttctatg gcgctgagat tgtgtcagcc | 780 | |
| ctggactacc tgcactcgga gaagaacgtg gtgtaccggg acctcaagct ggagaacctc | 840 | |
| atgctggaca aggacgggca cattaagatc acagacttcg ggctgtgcaa ggaggggatc | 900 | |
| aaggacggtg ccaccatgaa gaccttttgc ggcacacctg agtacctggc ccccgaggtg | 960 | |
| ctggaggaca atgactacgg ccgtgcagtg gactggtggg gctgggcgt ggtcatgtac | 1020 | |
| gagatgatgt gcggtcgcct gccccttctac aaccaggacc atgagaagct ttttgagctc | 1080 | |
| atcctcatgg aggagatccg cttcccgcgc acgcttggtc cgaggccaa gtccttgctt | 1140 | |
| tcagggctgc tcaagaagga ccccaagcag aggcttggcg ggggctccga ggacgccaag | 1200 | |
| gagatcatgc agcatcgctt ctttgccggt atcgtgtggc agcacgtgta cgagaagaag | 1260 | |
| ctcagcccac ccttcaagcc ccaggtcacg tcggagactg acaccaggta ttttgatgag | 1320 | |
| gagttcacgg cccagatgat caccatcaca ccacctgacc aagatgacag catggagtgt | 1380 | |
| gtggacagcg agcgcaggcc ccacttcccc cagttctcct actcggccag cggcacggcc | 1440 | |
| tga | 1443 | |

<210> SEQ ID NO 15
<211> LENGTH: 1061
<212> TYPE: DNA
<213> ORGANISM: Homo sapiens

<400> SEQUENCE: 15

| | | |
|---|---|---|
| tgccctgcgc ccgcaacccg agccgcaccc gccgcggacg gagcccatgc gcggggcgaa | 60 | |
| ccgcgcgccc ccgccccgc cccgcccgg cctcggcccc ggccctggcc ccgggggcag | 120 | |
| tcgcgcctgt gaacggtggg gcaggagacc ctgtaggagg accccgggcc gcaggcccct | 180 | |
| gaggagcgat gacggaatat aagctggtgg tggtgggcgc cggcggtgtg ggcaagagtg | 240 | |
| cgctgaccat ccagctgatc cagaaccatt ttgtggacga atacgacccc actatagagg | 300 | |
| attcctaccg gaagcaggtg gtcattgatg gggagacgtg cctgttggac atcctggata | 360 | |
| ccgccggcca ggaggagtac agcgccatgc gggaccagta catgcgcacc ggggagggct | 420 | |
| tcctgtgtgt gtttgccatc aacaacacca agtcttttga ggacatccac cagtacaggg | 480 | |
| agcagatcaa acgggtgaag gactcggatg acgtgcccat ggtgctggtg gggaacaagt | 540 | |
| gtgacctggc tgcacgcact gtggaatctc ggcaggctca ggacctcgcc cgaagctacg | 600 | |
| gcatccccta catcgagacc tcggccaaga cccggcaggg agtggaggat gccttctaca | 660 | |
| cgttggtgcg tgagatccgg cagcacaagc tgcggaagct gaaccctcct gatgagagtg | 720 | |
| gccccggctg catgagctgc aagtgtgtgc tctcctgacg cagcacaagc tcaggacatg | 780 | |
| gaggtgccga atgcaggaag gaggtgcaga cggaaggagg aggaaggaag gacgaagca | 840 | |
| aggaaggaag gaagggctgc tggagcccag tcaccccggg accgtgggcc gaggtgactg | 900 | |
| cagaccctcc cagggaggct gtgcacagac tgtcttgaac atcccaaatg ccaccggaac | 960 | |
| cccagcccctt agctcccctc ccaggcctct gtgggcccctt gtcggcaca gatgggatca | 1020 | |
| cagtaaatta ttggatggtc ttgaaaaaaa aaaaaaaaaa a | 1061 | |

```
<210> SEQ ID NO 16
<211> LENGTH: 2188
<212> TYPE: DNA
<213> ORGANISM: Homo sapiens

<400> SEQUENCE: 16 aggggggtgcc ggcggggctg cagcggaggc actttggaag aatgactctg gagtccatca      60
tggcgtgctg cctgagcgag gaggccaagg aagcccggcg gatcaacgac gagatcgagc     120
ggcagctccg cagggacaag cgggacgccc gccgggagct caagctgctg ctgctcggga     180
caggagagag tggcaagagt acgtttatca agcagatgag aatcatccat gggtcaggat     240
actctgatga agataaaagg ggcttcacca agctggtgta tcagaacatc ttcacggcca     300
tgcaggccat gatcagagcc atggacacac tcaagatccc atacaagtat gagcacaata     360
aggctcatgc acaattagtt cgagaagttg atgtggagaa ggtgtctgct tttgagaatc     420
catatgtaga tgcaataaag agtttatgga atgatcctgg aatccaggaa tgctatgata     480
gacgacgaga atatcaatta tctgactcta ccaaatacta tcttaatgac ttggaccgcg     540
tagctgaccc tgcctacctg cctacgcaac aagatgtgct tagagttcga gtccccacca     600
cagggatcat cgaataccccc tttgacttac aaagtgtcat tttcagaatg gtcgatgtag     660
ggggccaaag gtcagagaga agaaaatgga tacactgctt tgaaaatgtc acctctatca     720
tgtttctagt agcgcttagt gaatatgatc aagttctcgt ggagtcagac aatgagaacc     780
gaatggagga aagcaaggct ctctttagaa caattatcac ataccctgg ttccagaact     840 cctcggttat tctgttctta aacaagaaag atcttctaga ggagaaaatc atgtattccc     900
atctagtcga ctacttccca gaatatgatg accccagag atgcccag gcagcccgag     960 aattcattct gaagatgttc gtggacctga acccagacag tgacaaaatt atctactccc    1020
acttcacgtg cgccacagac accgagaata tccgctttgt ctttgctgcc gtcaaggaca    1080
ccatcctcca gttgaacctg aaggagtaca atctggtcta attgtgcctc ctagacaccc    1140
gccctgccct tccctggtgg gctattgaag atacacaaga gggactgtat ttctgtggaa    1200
aacaatttgc ataatactaa tttattgccg tcctggactc tgtgtgagcg tgtccacaga    1260
gtttgtagta atattatga ttttatttaa actattcaga ggaaaaacag aggatgctga    1320
agtacagtcc cagcacattt cctctctatc tttttttttag gcaaaacctt gtgactcagt    1380
gtattttaaa ttctcagtca tgcactcaca agataagac ttgtttctt ctgtctctct    1440 ctcttttttct tttctatgga gcaaaacaaa gctgatttcc cttttttctt ccccgctaa    1500 ttcatacctc cctcctgatg ttttcccag gttacaatgg cctttatcct agttccattc    1560
ttggtcaagt ttttctctca aatgatacag tcaggacaca tcgttcgatt taagccatca    1620
tcagcttaat ttaagtttgt agtttttgct gaaggattat atgtattaat acttacggtt    1680
ttaaatgtgt tgctttggat acacacatag tttcttttttt aatagaatat actgtcttgt    1740
ctcactttgg actgggacag tggatgccca tctaaaagtt aagtgtcatt tcttttagat    1800
gtttaccttc agccatagct tgattgctca gagaaatatg cagaaggcag gatcaaagac    1860
acacaggagt cctttcttttt gaaatgccac gtgccattgt ctttcctccc ttctttgctt    1920
ctttttctta ccctctcttt caattgcaga tgccaaaaaa gatgccaaca gacactacat    1980
taccctaatg gctgctaccc agaaaccttt tataggttgt tcttaatttt tttgttgttg    2040
ttgttcaagc ttttccttttc ttttttttttct tagtgtttgg gccacgattt taaaatgact    2100
```

| | |
|---|---|
| tttattatgg gtatgtgttg ccaaagctgg ctttttgtca aataaaatga atacgaactt | 2160 |
| aaaaaataaa aaaaaaaaaa aaaaaaaa | 2188 |

<210> SEQ ID NO 17
<211> LENGTH: 1540
<212> TYPE: DNA
<213> ORGANISM: Homo sapiens

<400> SEQUENCE: 17

| | |
|---|---|
| gccctcggcc ccgggccggc ccgccccgcc tcggccgccg cctggcgagc cgccgggtcc | 60 |
| ccgctcggcc ggtggccgag gccggagggc cgcggcgggc ggcggccgag cggctccgg | 120 |
| ccagggccgg gccggggggcc gggggggcggc ggcgggcagg cggccgcgtc ggccggggcc | 180 |
| gggacgatga ctctggagtc catgatggcg tgttgcctga gcgatgaggt gaaggagtcc | 240 |
| aagcggatca acgccgagat cgagaagcag ctgcggcggg acaagcgcga cgcccggcgc | 300 |
| gagctcaagc tgctgctgct cggcacgggc gagagcggga agagcacgtt catcaagcag | 360 |
| atgcgcatca tccacggcgc cggctactcg gaggaggaca agcgcggctt caccaagctc | 420 |
| gtctaccaga acatcttcac cgccatgcag gccatgatcc gggccatgga gacgctcaag | 480 |
| atcctctaca gtacgagca gaacaaggcc aatgcgctcc tgatccggga ggtggacgtg | 540 |
| gagaaggtga ccaccttcga gcatcagtac gtcagtgcca tcaagaccct gtgggaggac | 600 |
| ccgggcatcc aggaatgcta cgaccgcagg cgcgagtacc agctctccga ctctgccaag | 660 |
| tactacctga ccgacgttga ccgcatcgcc accttgggct acctgccca ccagcaggac | 720 |
| gtgctgcggg tccgcgtgcc caccaccggc atcatcgagt ccctttcga cctggagaac | 780 |
| atcatcttcc ggatggtgga tgtgggggggc cagcggtcgg agcggaggaa gtggatccac | 840 |
| tgctttgaga acgtgacatc catcatgttt ctcgtcgccc tcagcgaata cgaccaagtc | 900 |
| ctggtggagt cggacaacga gaaccggatg gaggagagca agccctgtt ccggaccatc | 960 |
| atcacctacc cctggttcca gaactcctcc gtcatcctct tcctcaacaa gaaggacctg | 1020 |
| ctggaggaca agatcctgta ctcgcacctg gtggactact tccccgagtt cgatggtccc | 1080 |
| cagcggggagc cccaggcggc gcgggagttc atcctgaaga tgttcgtgga cctgaacccc | 1140 |
| gacagcgaca agatcatcta ctcacacttc acgtgtgcca ccgacacgga gaacatccgc | 1200 |
| ttcgtgttcg cggccgtgaa ggacaccatc ctgcagctca acctcaagga gtacaacctg | 1260 |
| gtctgagcgc cccaggccca gggagacggg atggagacac ggggcaggac cttccttcca | 1320 |
| cggagcctgc gctgccgggc gggtggcgct gccgagtccg ggccgggct ctgccgcggg | 1380 |
| aggagatttt ttttttttca tatttttaac aaatggtttt tatttcacag ttatcagggg | 1440 |
| atgtacatct ctccctccgt acacttcgcg caccttctca cctttgtca acggcaaagg | 1500 |
| cagcctttt ctggccttga cttatggctc gctttttct | 1540 |

<210> SEQ ID NO 18
<211> LENGTH: 5190
<212> TYPE: DNA
<213> ORGANISM: Homo sapiens

<400> SEQUENCE: 18

| | |
|---|---|
| tctgggggct cggctttgcc gcgctcgctg cacttgggcg agagctggaa cgtggaccag | 60 |
| agctcggatc ccatcgcagc taccgcgatg agaggcgctc gcggcgcctg ggattttctc | 120 |
| tgcgttctgc tcctactgct tcgcgtccag acaggtcttt ctcaaccatc tgtgagtcca | 180 |
| ggggaaccgt ctccaccatc catccatcca ggaaaatcag acttaatagt ccgcgtgggc | 240 |

```
gacgagatta ggctgttatg cactgatccg ggctttgtca aatggacttt tgagatcctg      300
gatgaaacga atgagaataa gcagaatgaa tggatcacgg aaaaggcaga agccaccaac      360
accggcaaat acacgtgcac caacaaacac ggcttaagca attccattta tgtgtttgtt      420
agagatcctg ccaagctttt ccttgttgac cgctccttgt atgggaaaga agacaacgac      480
acgctggtcc gctgtcctct cacagaccca gaagtgacca attattccct caggggtgc       540 caggggaagc ctcttcccaa ggacttgagg tttattcctg accccaaggc gggcatcatg      600
atcaaaagtg tgaaacgcgc ctaccatcgg ctctgtctgc attgttctgt ggaccaggag      660
ggcaagtcag tgctgtcgga aaaattcatc ctgaaagtga ggccagcctt caaagctgtg      720
cctgttgtgt ctgtgtccaa agcaagctat cttcttaggg aaggggaaga attcacagtg      780
acgtgcacaa taaagatgt gtctagttct gtgtactcaa cgtggaaaag agaaaacagt       840
cagactaaac tacaggagaa atataatagc tggcatcacg gtgacttcaa ttatgaacgt      900
caggcaacgt tgactatcag ttcagcgaga gttaatgatt ctggagtgtt catgtgttat      960
gccaataata cttttggatc agcaaatgtc acaacaacct tggaagtagt agataaagga     1020
ttcattaata tcttccccat gataaacact acagtatttg taaacgatgg agaaaatgta     1080
gatttgattg ttgaatatga agcattcccc aaacctgaac accagcagtg gatctatatg     1140
aacagaacct tcactgataa atgggaagat tatcccaagt ctgagaatga agtaatatc      1200 agatacgtaa gtgaacttca tctaacgaga ttaaaaggca ccgaaggagg cacttacaca     1260
ttcctagtgt ccaattctga cgtcaatgct gccatagcat ttaatgttta tgtgaataca     1320
aaaccagaaa tcctgactta cgacaggctc gtgaatggca tgctccaatg tgtggcagca     1380
ggattcccag agcccacaat agattggtat ttttgtccag gaactgagca gagatgctct     1440
gcttctgtac tgccagtgga tgtgcagaca ctaaactcat ctgggccacc gtttggaaag     1500
ctagtggttc agagttctat agattctagt gcattcaagc acaatggcac ggttgaatgt     1560
aaggcttaca cgatgtggg caagacttct gcctatttta actttgcatt taaaggtaac      1620
aacaaagagc aaatccatcc ccacaccctg ttcactcctt tgctgattgg tttcgtaatc     1680
gtagctggca tgatgtgcat tattgtgatg attctgacct acaaatattt acagaaaccc     1740
atgtatgaag tacagtggaa ggttgttgag gagataaatg gaaacaatta tgtttacata     1800
gacccaacac aacttcctta tgatcacaaa tgggagtttc cagaaaacag gctgagtttt     1860
gggaaaaccc tgggtgctgg agctttcggg aaggttgttg aggcaactgc ttatggctta     1920
attaagtcag atgcggccat gactgtcgct gtaaagatgc tcaagccgag tgcccatttg     1980
acagaacggg aagccctcat gtctgaactc aaagtcctga gttaccttgg taatcacatg     2040
aatattgtga atctacttgg agcctgcacc attggagggc ccaccctggt cattacagaa     2100
tattgttgct atggtgatct tttgaattt tgagaagaa aacgtgattc atttatttgt       2160
tcaaagcagg aagatcatgc agaagctgca ctttataaga atcttctgca ttcaaggag      2220 tcttcctgca gcgatagtac taatgagtac atggacatga aacctggagt ttcttatgtt     2280
gtcccaacca aggccgacaa aaggagatct gtgagaatag gctcatacat agaaagagat     2340
gtgactcccg ccatcatgga ggatgacgag ttggccctag acttagaaga cttgctgagc     2400
ttttcttacc aggtggcaaa gggcatggct ttcctcgcct ccaagaattg tattcacaga     2460
gacttggcag ccagaaatat cctccttact catggtcgga tcacaaagat ttgtgatttt     2520
ggtctagcca gagacatcaa gaatgattct aattatgtgg ttaaaggaaa cgctcgacta     2580
cctgtgaagt ggatggcacc tgaaagcatt ttcaactgtg tatacacgtt tgaaagtgac     2640
```

```
gtctggtcct atgggatttt tctttgggag ctgttctctt taggaagcag cccctatcct  2700
ggaatgccgg tcgattctaa gttctacaag atgatcaagg aaggcttccg gatgctcagc  2760
cctgaacacg cacctgctga atgtatgac  ataatgaaga cttgctggga tgcagatccc  2820
ctaaaaagac caacattcaa gcaaattgtt cagctaattg agaagcagat ttcagagagc  2880
accaatcata tttactccaa cttagcaaac tgcagcccca accgacagaa gcccgtggta  2940
gaccattctg tgcggatcaa ttctgtcggc agcaccgctt cctcctccca gcctctgctt  3000
gtgcacgacg atgtctgagc agaatcagtg tttgggtcac ccctccagga atgatctctt  3060
cttttggctt ccatgatggt tattttcttt tctttcaact tgcatccaac tccaggatag  3120
tgggcacccc actgcaatcc tgtctttctg agcacacttt agtggccgat gattttgtc   3180
atcagccacc atcctattgc aaaggttcca actgtatata ttcccaatag caacgtagct  3240
tctaccatga acagaaaaca ttctgatttg gaaaaagaga gggaggtatg gactgggggc  3300
cagagtcctt tccaaggctt ctccaattct gcccaaaaat atggttgata gtttacctga  3360
ataaatggta gtaatcacag ttggccttca gaaccatcca tagtagtatg atgatacaag  3420
attagaagct gaaaacctaa gtcctttatg tggaaaacag aacatcatta gaacaaagga  3480
cagagtatga acacctgggc ttaagaaatc tagtatttca tgctgggaat gagacatagg  3540
ccatgaaaaa aatgatcccc aagtgtgaac aaaagatgct cttctgtgga ccactgcatg  3600
agctttata  ctaccgacct ggttttaaa  tagagtttgc tattagagca ttgaattgga  3660
gagaaggcct ccctagccag cacttgtata tacgcatcta taaattgtcc gtgttcatac  3720
atttgagggg aaaacaccat aaggtttcgt ttctgtatac aaccctggca ttatgtccac  3780
tgtgtataga agtagattaa gagccatata agtttgaagg aaacagttaa taccatttt   3840
taaggaaaca atataaccac aaagcacagt ttgaacaaaa tctcctcttt tagctgatga  3900
acttattctg tagattctgt ggaacaagcc tatcagcttc agaatggcat tgtactcaat  3960
ggatttgatg ctgtttgaca aagttactga ttcactgcat ggctcccaca ggagtgggaa  4020
aacactgcca tcttagtttg gattcttatg tagcaggaaa taaagtatag gtttagcctc  4080
cttcgcaggc atgtcctgga caccgggcca gtatctatat atgtgtatgt acgtttgtat  4140
gtgtgtagac aaatatttgg agggtatt   ttgccctgag tccaagaggg tcctttagta  4200
cctgaaaagt aacttggctt tcattattag tactgctctt gtttcttttc acatagctgt  4260
ctagagtagc ttaccagaag cttccatagt ggtgcagagg aagtggaagg catcagtccc  4320
tatgtatttg cagttcacct gcacttaagg cactctgtta tttagactca tcttactgta  4380
cctgttcctt agaccttcca taatgctact gtctcactga acatttaaa  ttttaccctt  4440
tagactgtag cctggatatt attcttgtag tttacctctt taaaaacaaa acaaaacaaa  4500
acaaaaaact ccccttcctc actgcccaat ataaaggca  aatgtgtaca tggcagagtt  4560
tgtgtgttgt cttgaaagat tcaggtatgt tgcctttatg gtttccccct tctacatttc  4620
ttagactaca tttagagaac tgtggccgtt atctggaagt aaccatttgc actggagttc  4680
tatgctctcg cacctttcca aagttaacag attttggggt tgtgttgtca cccaagagat  4740
tgttgtttgc catactttgt ctgaaaaatt cctttgtgtt tctattgact tcaatgatag  4800
taagaaaagt ggttgttagt tatagatgtc taggtacttc aggggcactt cattgagagt  4860
tttgtcttgg atattcttga agtttatat  ttttataatt ttttcttaca tcagatgttt  4920
ctttgcagtg gcttaatgtt tgaattatt  ttgtggcttt ttttgtaaat attgaaatgt  4980
agcaataatg tcttttgaat attcccaagc ccatgagtcc ttgaaaatat tttttatata  5040
```

```
tacagtaact ttatgtgtaa atacataagc ggcgtaagtt taaaggatgt tggtgttcca      5100
cgtgttttat tcctgtatgt tgtccaattg ttgacagttc tgaagaattc taataaaatg      5160
tacatatata aatcaaaaaa aaaaaaaaaa                                       5190

<210> SEQ ID NO 19
<211> LENGTH: 5527
<212> TYPE: DNA
<213> ORGANISM: Homo sapiens

<400> SEQUENCE: 19
cgcggccgcc ctgggcgggc gcgggcggcg ggcggcggtg agggcggcct gcggggcggc        60 gcccggggc cggggccgagc cgggcctgag ccggccccgg accgagctgg gagaggggct       120
ccggcccgat cgttcgcttg cgcaaaatg ttggagatct gcctgaagct ggtgggctgc       180
aaatccaaga aggggctgtc ctcgtcctcc agctgttatc tggaagaagc ccttcagcgg       240
ccagtagcat ctgactttga gcctcagggt ctgagtgaag ccgctcgttg gaactccaag       300
gaaaaccttc tcgctggacc cagtgaaaat gaccccaacc ttttcgttgc actgtatgat       360
tttgtggcca gtggagataa cactctaagc ataactaaag gtgaaaagct ccgggtctta       420
ggctataatc acaatgggga atggtgtgaa gcccaaacca aaaatggcca aggctgggtc       480
ccaagcaact acatcacgcc agtcaacagt ctggagaaac actcctggta ccatgggcct       540
gtgtcccgca atgccgctga gtatctgctg agcagcggga tcaatggcag cttcttggtg       600
cgtgagagtg agagcagtcc tggccagagg tccatctcgc tgagatacga agggagggtg       660
taccattaca ggatcaacac tgcttctgat ggcaagctct acgtctcctc cgagagccgc       720
ttcaacaccc tggccgagtt ggttcatcat cattcaacgg tggccgacgg gctcatcacc       780
acgctccatt atccagcccc aaagcgcaac aagcccactg tctatggtgt gtccccccaac       840 tacgacaagt gggagatgga acgcacggac atcaccatga gcacaagct gggcgggggc       900 cagtacgggg aggtgtacga gggcgtgtgg aagaaataca gcctgacggt ggccgtgaag       960
accttgaagg aggacaccat ggaggtggaa gagttcttga agaagctgc agtcatgaaa      1020 gagatcaaac ccctaacct ggtgcagctc cttgggggtct gcacccggga gccccgttc      1080 tatatcatca ctgagttcat gacctacggg aacctcctgg actacctgag ggagtgcaac      1140
cggcaggagg tgaacgccgt ggtgctgctg tacatggcca ctcagatctc gtcagccatg      1200
gagtacctgg agaagaaaa cttcatccac agagatcttg ctgcccgaaa ctgcctggta      1260
ggggagaacc acttggtgaa ggtagctgat tttggcctga gcaggttgat gacaggggac      1320
acctacacag cccatgctgg agccaagttc cccatcaaat ggactgcacc cgagagcctg      1380
gcctacaaca gttctccat caagtccgac gtctgggcat ttggagtatt gctttgggaa      1440
attgctacct atggcatgtc cccttaccg ggaattgacc tgtcccaggt gtatgagctg      1500
ctagagaagg actaccgcat ggagcgccca aaggctgcc agagaaggt ctatgaactc      1560 atgcgagcat gttggcagtg gaatccctct gaccggccct cctttgctga atccaccaa      1620 gcctttgaaa caatgttcca ggaatccagt atctcagacg aagtggaaaa ggagctgggg      1680
aaacaaggcg tccgtgggc tgtgagtacc ttgctgcagg ccccagagct gcccaccaag      1740
acgaggacct ccaggagagc tgcagagcac agagacacca ctgacgtgcc tgagatgcct      1800
cactccaagg gccagggaga gagcgatcct ctggaccatg agcctgccgt gtctccattg      1860
ctccctcgaa aagagcgagg tccccgggag ggcggcctga atgaagatga gcgccttctc      1920
cccaaagaca aaaagaccaa cttgttcagc gccttgatca agaagaagaa gaagacagcc      1980
```

```
ccaacccctc ccaaacgcag cagctccttc cgggagatgg acggccagcc ggagcgcaga    2040
ggggccggcg aggaagaggg ccgagacatc agcaacgggg cactggcttt cacccccttg    2100
gacacagctg acccagccaa gtccccaaag cccagcaatg gggctggggt ccccaatgga    2160
gccctccggg agtccggggg ctcaggcttc cggtctcccc acctgtggaa gaagtccagc    2220
acgctgacca gcagccgcct agccaccggc gaggaggagg gcggtggcag ctccagcaag    2280
cgcttcctgc gctcttgctc cgcctcctgc gttccccatg gggccaagga cacggagtgg    2340
aggtcagtca cgctgcctcg ggacttgcag tccacgggaa gacagtttga ctcgtccaca    2400
tttggagggc acaaaagtga gaagccggct ctgcctcgga gagggcaggg gagaacagg    2460
tctgaccagg tgacccgagg cacagtaacg cctcccccca ggctggtgaa aaagaatgag    2520
gaagctgctg atgaggtctt caaagacatc atggagtcca gcccgggctc cagcccgccc    2580
aacctgactc caaaccccct ccggcggcag gtcaccgtgg cccctgcctc gggcctcccc    2640
cacaaggaag aagctgaaaa gggcagtgcc ttagggaccc ctgctgcagc tgagccagtg    2700
accccccacca gcaaagcagg ctcaggtgca ccaggggca ccagcaaggg cccgccgag    2760
gagtccagag tgaggaggca caagcactcc tctgagtcgc cagggaggga caaggggaaa    2820
ttgtccaggc tcaaacctgc cccgccgccc ccaccagcag cctctgcagg gaaggctgga    2880
ggaaagccct cgcagagccc gagccaggag gcggccgggg aggcagtcct gggcgcaaag    2940
acaaaagcca cgagtctggt tgatgctgtg aacagtgacg ctgccaagcc cagccagccg    3000
ggagagggcc tcaaaaagcc cgtgctcccg gccactccaa agccacagtc cgccaagccg    3060
tcggggaccc ccatcagccc agcccccgtt ccctccacgt tgccatcagc atcctcggcc    3120
ctggcagggg accagccgtc ttccactgcc ttcatccctc tcatatcaac ccgagtgtct    3180
cttcggaaaa cccgccagcc tccagagcgg atcgccagcg cgccatcac caagggcgtg    3240
gtcctggaca gcaccgaggc gctgtgcctc gccatctcta ggaactccga gcagatggcc    3300
agccacagcg cagtgctgga ggccggcaaa aacctctaca cgttctgcgt gagctatgtg    3360
gattccatcc agcaaatgag gaacaagttt gccttccgag aggccatcaa caaactggag    3420
aataatctcc gggagcttca gatctgcccg gcgacagcag gcagtggtcc ggcggccact    3480
caggacttca gcaagctcct cagttcggtg aaggaaatca gtgacatagt gcagaggtag    3540
cagcagtcag gggtcaggtg tcaggcccgt cggagctgcc tgcagcacat gcgggctcgc    3600
ccatacccat gacagtggct gacaagggac tagtgagtca gcaccttggc ccaggagctc    3660
tgcgccaggc agagctgagg gccctgtgga gtccagctct actacctacg tttgcaccgc    3720
ctgccctccc gcaccttcct cctccccgct ccgtctctgt cctcgaattt tatctgtgga    3780
gttcctgctc cgtggactgc agtcggcatg ccaggacccg ccagcccgc tcccacctag    3840
tgccccagac tgagctctcc aggccaggtg ggaacggctg atgtggactg tctttttcat    3900
ttttttctct ctggagcccc tcctccccg gctgggcctc cttcttccac ttctccaaga    3960
atggaagcct gaactgaggc cttgtgtgtc aggccctctg cctgcactcc ctggccttgc    4020
ccgtcgtgtg ctgaagacat gtttcaagaa ccgccatttc gggaagggca tgcacgggcc    4080
atgcacacgt ctggtcactc tgccctctgc tgctgcccgg ggtggggtgc actcgccatt    4140
tcctcacgtg caggacagct cttgatttgg gtggaaaaca gggtgctaaa gccaaccagc    4200
ctttgggtcc tgggcaggtg ggagctgaaa aggatcgagg catgggcat gtcctttcca    4260
tctgtccaca tccccagagc ccagctcttg ctctcttgtg acgtgcactg tgaatcctgg    4320
caagaaagct tgagtctcaa gggtggcagg tcactgtcac tgccgacatc cctccccag    4380
```

| | | |
|---|---|---|
| cagaatggag gcaggggaca agggaggcag tggctagtgg ggtgaacagc tggtgccaaa | 4440 | |
| tagccccaga ctgggcccag gcaggtctgc aagggcccag agtgaaccgt cctttcacac | 4500 | |
| atctgggtgc cctgaagggc ccttcccctc ccccactcct ctaagacaaa gtagattctt | 4560 | |
| acaaggccct ttcctttgga acaagacagc cttcactttt ctgagttctt gaagcatttc | 4620 | |
| aaagccctgc ctctgtgtag ccgccctgag agagaataga gctgccactg ggcacctcgc | 4680 | |
| gacaggtggg aggaaaggc ctgcgcagtc ctggtcctgg ctgcactctt gaactgggcg | 4740 | |
| aatgtcttat ttaattaccg tgagtgacat agcctcatgt tctgtggggg tcatcaggga | 4800 | |
| gggttaggaa aaccacaaac ggagccctg aaagcctcac gtatttcaca gagcacgcct | 4860 | |
| gccatcttct ccccgaggct gccccaggcc ggagcccaga taccggcggg ctgtgactct | 4920 | |
| gggcagggac ccggggtctc ctggaccttg acagagcagc taactccgag agcagtgggc | 4980 | |
| aggtggccgc ccctgaggct tcacgccgga gaagccacct tcccgcccct tcataccgcc | 5040 | |
| tcgtgccagc agcctcgcac aggccctagc tttacgctca tcacctaaac ttgtacttta | 5100 | |
| tttttctgat agaaatggtt tcctctggat cgttttatgc ggttcttaca gcacatcacc | 5160 | |
| tctttccccc cgacggctgt gacgcagcgg agaggcacta gtcaccgaca gcggccttga | 5220 | |
| agacagagca aagcccccac ccaggtcccc cgactgcctg tctccatgag gtactggtcc | 5280 | |
| cttcctttg ttaacgtgat gtgccactat attttacacg tatctcttgg tatgcatctt | 5340 | |
| ttatagacgc tcttttctaa gtggcgtgtg catagcgtcc tgccctgccc tcggggggcct | 5400 | |
| gtggtggctc ccctctgct tctcggggtc cagtgcattt tgtttctgta tatgattctc | 5460 | |
| tgtggttttt tttgaatcca aatctgtcct ctgtagtatt ttttaaataa atcagtgttt | 5520 | |
| acattag | 5527 | |

<210> SEQ ID NO 20
<211> LENGTH: 2603
<212> TYPE: DNA
<213> ORGANISM: Homo sapiens

<400> SEQUENCE: 20

| | | |
|---|---|---|
| aggcgaggct tccccttccc cgcccctccc ccggcctcca gtccctccca gggccgcttc | 60 | |
| gcagagcggc taggagcacg gcggcggcgg cactttcccc ggcaggagct ggagctgggc | 120 | |
| tctggtgcgc gcgcggctgt gccgcccgag ccggagggac tggttggttg agagagagag | 180 | |
| aggaagggaa tcccgggctg ccgaaccgca cgttcagccc gctccgctcc tgcagggcag | 240 | |
| cctttcggct ctctgcgcgc gaagccgagt cccgggcggg tggggcgggg gtccactgag | 300 | |
| accgctaccg gcccctcggc gctgacggga ccgcgcgggg cgcacccgct gaaggcagcc | 360 | |
| ccggggcccg cggcccggac ttggtcctgc gcagcgggcg cggggcagcg cagcgggagg | 420 | |
| aagcgagagg tgctgccctc cccccggagt tggaagcgcg ttacccgggt ccaaaatgcc | 480 | |
| caagaagaag ccgacgccca tccagctgaa cccggccccc gacggctctg cagttaacgg | 540 | |
| gaccagctct gcggagacca acttggaggc cttgcagaag aagctggagg agctagagct | 600 | |
| tgatgagcag cagcgaaagc gccttgaggc cttttcttacc cagaagcaga aggtgggaga | 660 | |
| actgaaggat gacgactttg agaagatcag tgagctgggg gctggcaatg gcggtgtggt | 720 | |
| gttcaaggtc tcccacaagc cttctggcct ggtcatggcc agaaagctaa ttcatctgga | 780 | |
| gatcaaaccc gcaatccgga accagatcat aagggagctg caggttctgc atgagtgcaa | 840 | |
| ctctccgtac atcgtgggct tctatggtgc gttctacagc gatggcgaga tcagtatctg | 900 | |
| catggagcac atggatggag ttctctgga tcaagtcctg aagaaagctg gaagaattcc | 960 | |

```
tgaacaaatt ttaggaaaag ttagcattgc tgtaataaaa ggcctgacat atctgaggga      1020
gaagcacaag atcatgcaca gagatgtcaa gccctccaac atcctagtca actcccgtgg      1080
ggagatcaag ctctgtgact tggggtcag  cgggcagctc atcgactcca tggccaactc      1140
cttcgtgggc acaaggtcct acatgtcgcc agaaagactc cagggactc  attactctgt      1200 gcagtcagac atctggagca tgggactgtc tctggtagag atggcggttg ggaggtatcc      1260
catccctcct ccagatgcca aggagctgga gctgatgttt gggtgccagg tggaaggaga      1320
tgcggctgag accccaccca ggccaaggac ccccgggagg ccccttagct catacggaat      1380
ggacagccga cctcccatgg caattttga  gttgttggat tacatagtca acgagcctcc      1440
tccaaaactg cccagtggag tgttcagtct ggaatttcaa gattttgtga ataaatgctt      1500
aataaaaaac cccgcagaga gagcagattt gaagcaactc atggttcatg cttttatcaa      1560
gagatctgat gctgaggaag tggattttgc aggttggctc tgctccacca tcggccttaa      1620
ccagcccagc acaccaaccc atgctgctgg cgtctaagtg tttgggaagc aacaaagagc      1680
gagtcccctg cccggtggtt tgccatgtcg cttttgggcc tccttcccat gcctgtctct      1740
gttcagatgt gcatttcacc tgtgacaaag gatgaagaac acagcatgtg ccaagattct      1800
actcttgtca ttttaatat tactgtcttt attcttatta ctattattgt tcccctaagt      1860
ggattggctt tgtgcttggg gctatttgtg tgtatgctga tgatcaaaac ctgtgccagg      1920
ctgaattaca gtgaaatttt ggtgaatgtg ggtagtcatt cttacaattg cactgctgtt      1980
cctgctccat gactggctgt ctgcctgtat tttcgggatt cttttgacatt tggtggtact      2040 ttattcttgc tgggcatact ttctctctag gagggagcct tgtgagatcc ttcacaggca      2100
gtgcatgtga agcatgcttt gctgctatga aaatgagcat cagagagtgt acatcatgtt      2160
attttattat tattatttgc ttttcatgta gaactcagca gttgacatcc aaatctagcc      2220
agagcccttc actgccatga tagctggggc ttcaccagtc tgtctactgt ggtgatctgt      2280
agacttctgg ttgtatttct atatttattt tcagtatact gtgtgggata cttagtggta      2340
tgtctcttta agttttgatt aatgtttctt aaatggaatt attttgaatg tcacaaattg      2400
atcaagatat taaaatgtcg gatttatctt tccccatatc caagtaccaa tgctgttgta      2460
aacaacgtgt atagtgccta aaattgtatg aaaatccttt taaccatttt aacctagatg      2520
tttaacaaat ctaatctctt attctaataa atatactatg aataaaaaa  aaaaggatga      2580 aagctaaaaa aaaaaaaaaa aaa                                              2603
```

<210> SEQ ID NO 21
<211> LENGTH: 84
<212> TYPE: DNA
<213> ORGANISM: Artificial Sequence
<220> FEATURE:
<223> OTHER INFORMATION: BRAF V600E with primer sequences

<400> SEQUENCE: 21

```
actgcggtcc tgagcgagtg attttggtct agctacagag aaatctcgat ggagtgggtc      60
ccatcaggcc aacctccacc gtcg                                             84
```

<210> SEQ ID NO 22
<211> LENGTH: 84
<212> TYPE: DNA
<213> ORGANISM: Artificial sequence
<220> FEATURE:
<223> OTHER INFORMATION: BRAF wild type sequence with primer sequences

```
<400> SEQUENCE: 22
gccaacctcc accgtcggtg attttggtct agctacagtg aaatctcgat ggagtgggtc    60
ccatcagact gcggtcctga gcga                                          84

<210> SEQ ID NO 23
<211> LENGTH: 20
<212> TYPE: DNA
<213> ORGANISM: Artificial Sequence
<220> FEATURE:
<223> OTHER INFORMATION: Probe for separation medium

<400> SEQUENCE: 23
catcgagatt tctctgtagc                                               20

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
ctactgtttt cctttactta ctacacc                                       27

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
ctcaattctt accatccaca aaatg                                         25

<210> SEQ ID NO 26
<211> LENGTH: 45
<212> TYPE: DNA
<213> ORGANISM: Artificial Sequence
<220> FEATURE:
<223> OTHER INFORMATION: Primer

<400> SEQUENCE: 26
gactgactga ctgactgact gactgtgatt ttggtctagc tacag                   45

<210> SEQ ID NO 27
<211> LENGTH: 20
<212> TYPE: DNA
<213> ORGANISM: Artificial Sequence
<220> FEATURE:
<223> OTHER INFORMATION: Probe for separation medium

<400> SEQUENCE: 27
catcgagatt tctctgtagc                                               20

<210> SEQ ID NO 28
<211> LENGTH: 19
<212> TYPE: DNA
<213> ORGANISM: Artificial Sequence
<220> FEATURE:
<223> OTHER INFORMATION: Probe for separation medium

<400> SEQUENCE: 28
ggcaugagcu gcaugauga                                                19
```

```
<210> SEQ ID NO 29
<211> LENGTH: 26
<212> TYPE: DNA
<213> ORGANISM: Artificial sequence
<220> FEATURE:
<223> OTHER INFORMATION: Probe for separation medium

<400> SEQUENCE: 29
ctttcggaga tgttttgata gcgacg                                            26

<210> SEQ ID NO 30
<211> LENGTH: 22
<212> TYPE: DNA
<213> ORGANISM: Artificial sequence
<220> FEATURE:
<223> OTHER INFORMATION: Probe for separation medium

<400> SEQUENCE: 30
tttcggagac ttgatagcga cg                                                22

<210> SEQ ID NO 31
<211> LENGTH: 15
<212> TYPE: DNA
<213> ORGANISM: Artificial sequence
<220> FEATURE:
<223> OTHER INFORMATION: Probe for separation medium

<400> SEQUENCE: 31
gcccgcccaa aatct                                                        15
```

BIOMARKER ANAYLSIS USING SCODAPHORESIS

RELATED APPLICATIONS

This application claims priority to U.S. Patent Application No. 61/643,144 filed May 4, 2012, which is incorporated by reference herein in its entirety.

FIELD OF THE INVENTION

This invention relates to methods and apparatus for characterizing nucleic acid sequences that are biomarkers, e.g., for cancer. Embodiments of the invention combine Scodaphoresis with other techniques to first enrich a sample for nucleic acids and then characterize the nucleic acids, e.g. by determining the order of the bases in the sequence. Because the nucleic acids are enriched prior to characterization, the technique can characterize nucleic acids that are present in only trace amounts, e.g., as cell-free DNA in blood plasma.

BACKGROUND

A large number of diseases, such as cancer, birth defects, and infections can be identified and evaluated using nucleic acid screening. In some cases, the presence of a single mutation, e.g., BRCA1, is a strong indicator of a likelihood of developing disease. In other cases, a disease manifests with a combination of trace mutations, and the level of the mutant nucleic acids relative to the wild-type is indicative of the progression of the disease. In either case, techniques that allow detection of rare nucleic acid mutations with non-invasive sampling make it possible for subjects to be monitored regularly for the presence of the disease. Such monitoring allows for early intervention while avoiding unnecessary treatment. Ideally, such methods should be low-cost, to allow for regular monitoring of a large population of patients.

Standard nucleic acid separation techniques limit clinicians' abilities to analyze samples for nucleic acids that are present in low abundance, however. In particular, it is difficult to resolve rare nucleic acids that are present at low concentrations in the presence of closely-related nucleic acids, e.g., wild-type DNA. Furthermore, many non-invasive sampling methods, e.g., blood draws or buccal swabs, only provide a limited number of mutant nucleic acids, as compared to a tumor biopsy.

To resolve rare mutations in a sample, state-of-the-art methods typically amplify all of the nucleic acids prior to isolation and analysis. For example, using Polymerase Chain Reaction (PCR) amplification, each nucleic acid in a sample can be amplified one million times (or more). Theoretically, there will be a million-fold increase of each nucleic acid originally present, and, thus, a greater opportunity to isolate and find the nucleic acids in low abundance. In practice, however, PCR amplification has significant drawbacks when used to amplify nucleic acids that are present in low abundance. The PCR reaction is stochastic, and to the extent that a low-abundance nucleic acid is not amplified in the first few rounds of PCR, it likely will not be detected. In addition, PCR amplification introduces sequence errors in the amplicons. If the error rate is high enough, there can be a significant effect on the resulting sequence data, especially in applications requiring the detection of rare sequence variants. In fact, mutations present at a concentration on the order of the level of detection (LOD) of state-of-the-art techniques (about 1%) cannot be reliably determined because of the amplification errors introduced by PCR.

In addition to lacking the needed sensitivity, state-of-the-art nucleic acid screening techniques are also expensive, costing several thousand dollars to identify only a handful of biomarkers at a time. The high costs reflect that the techniques are technically challenging, time-consuming, and require the use of apparatus with limited availability. New methods of labeling nucleic acids, such as barcoding, allow multiplexed high throughput sequencing of samples, which can reduce the cost of an individual sample. Nonetheless, these labelling methods often rely on PCR amplification to incorporate the labels, and suffer many of the same problems, such as introduction of errant bases and unequal amplification due to early biases in regard to which nucleic acids are amplified.

Accordingly, there is still a need for techniques that easily isolate rare nucleic acids from a sample prior to further processing, e.g., sequencing. It would also be beneficial if such techniques could simultaneously process multiple nucleic acids, either from the same subject or from pooled subject samples.

SUMMARY

The invention provides apparatus and methods for characterizing rare nucleic acids, such as low-abundance mutations that are indicative of a disease. By using a technique known as Scodaphoresis, it is possible to enrich a sample for the rare nucleic acids, making the subsequent characterization of those nucleic acids far more effective. In some instance, a small number of amplification cycles precede the enrichment and allow the incorporation of labels into the nucleic acids. After enrichment, it is then possible to multiplex a plurality of nucleic acids and determine, after characterization, the origin of each nucleic acid. Accordingly, the methods and apparatus provide a sensitive and lower-cost method for identifying and characterizing rare nucleic acids in samples. In some embodiments, the apparatus and methods allow for the characterization of specific mutations in a biological sample across several orders of magnitude, e.g. from 0.01% to 100% abundance. In some embodiments, the abundance of multiple mutations, e.g. more than 10, more than 20, more than 100, or between 10 and 150 can be assessed. In some embodiments, the nucleic acids in the sample that are assessed for the presence of mutations are short, e.g. between 20 and 50 bases in length. In some embodiments, the abundance of such mutations in a plurality of different patients can be assessed in a pooled sample. In some embodiments, the nucleic acids are short fragments of nucleic acids in the sample. In some embodiments, short portions of longer nucleic acids are amplified, e.g. to provide amplicons between 20 and 50 bases in length.

Because the disclosed methods and apparatus allow for sensitive and lower cost characterization of rare nucleic acids, the methods and apparatus can be used to provide regular non-invasive screening for patients that have developed a disease, or because of family history, are at risk for developing the disease. For example, a patient that has been treated for cancer can be monitored regularly to determine if the cancer is still in remission. In other instances, a patient that is undergoing treatment for a disease can be monitored to determine if the treatment is effective, or whether a different treatment should be used.

Further aspects and example embodiments are illustrated in the accompanying drawings and/or described in the following description.

BRIEF DESCRIPTION OF THE DRAWINGS

The accompanying drawings illustrate non-limiting example of embodiments of the invention.

FIGS. 10A-10E show multiplexed scodaphoretic separation of a plurality of different mutant and wild type DNA sequences for different genes;

As shown in FIG. 14A, a KRAS G12V mutant must be present in at least 1% as compared to the wild-type nucleic acid to exceed the LOD using state-of-the-art characterization methods;

DETAILED DESCRIPTION

Figure 1:
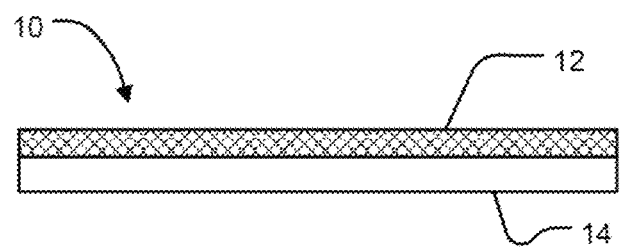
FIG. 1 is a schematic cross-sectional view of a medium according to one embodiment.

The invention provides methods and apparatus for characterizing nucleic acids, such as mutant nucleic acids that can be analyzed/quantified as biomarkers. In particular, the methods of the invention allow at least a 100-fold increase in sensitivity as compared to state-of-the-art methods, allowing less invasive samples to be analyzed, where the biomarkers are present in lesser numbers, as compared to, for example, a tumor biopsy. Accordingly, the invention can be used to diagnose, treat, or monitor the progression of a variety of diseases that have known nucleic acid biomarkers. The invention additionally lends itself to high-throughput screening and multiplexing, thus allowing many samples to be simultaneously processed and characterized. This feature allows many individual samples to be simultaneously processed, or it allows complicated panels of biomarkers to be quickly and efficiently evaluated. In both instances, the methods of the invention result in lower cost per analyzed mutant nucleic acid as compared to state-of-the-art methods.

The methods of the invention generally comprise the steps of providing a sample comprising a nucleic acid, loading the sample on a medium, enriching the sample for the nucleic acid by applying a time-varying driving field and a time-varying mobility-varying field to the separation medium, and characterizing the enriched nucleic acid in the sample. Characterizing can include determining a sequence of the nucleic acid, determining an amount of the enriched nucleic acid as compared to another nucleic acid, or determining an absolute number of nucleic acid molecules in the sample, among other methods of characterizing the nucleic acid.

Some embodiments of the present invention can be used to analyze mutations present in nucleic acid material obtained from a subject. In some embodiments, a sample is obtained from a subject, nucleic acids (e.g. DNA or RNA) are obtained from the sample, the content of specific mutations within the nucleic acids is measured and/or detected, selected nucleic acids in the sample are amplified, the specific mutations are enriched in the sample by scodaphoresis, and the content of specific mutations within the enriched sample is measured and/or detected. Some embodiments of the present invention can be used to provide a quantitative analysis of the abundance of one or more selected mutations even where the abundance of such mutations varies by several orders of magnitude.

For any of the above purposes, methods may be applied to biological samples. The biological samples may, for example, comprise samples of blood, whole blood, blood plasma, tears, nipple aspirate, serum, stool, urine, saliva, circulating cells, tissue, biopsy samples, or other samples containing biological material of the patient. One issue in conducting tests based on such samples is that, in most cases only a tiny amount of DNA or RNA containing a mutation of interest may be present in a sample. This is especially true in non-invasive samples, such as a buccal swab or a blood sample, where the mutant nucleic acids are present in very small amounts. Furthermore, the mutant nucleic acids make up only a tiny fraction of the total amount of DNA or RNA in the sample. Therefore, a test must be able to discriminate mutated DNA or RNA from normal (or 'wild type') DNA or RNA with high specificity to avoid false positive readings. It is also desirable that a test provide the ability to work with whole blood to collect both circulating nucleic acids and circulating cells at the same time. It is also desirable that a test provide the ability to detect short fragments of nucleic acids, e.g. less than 50 bases in length. (The target fragments may be short in vivo, or random shearing of relevant nucleic acids in the sample can generate short fragments.)

Nucleic acids may be obtained by methods known in the art. Generally, nucleic acids can be extracted from a biological sample by a variety of techniques such as those described by Maniatis, et al., Molecular Cloning: A Laboratory Manual, Cold Spring Harbor, N.Y., pp. 280-281, (1982), the contents of which is incorporated by reference herein in its entirety.

It may be necessary to first prepare an extract of the sample and then perform further steps—i.e., differential precipitation, column chromatography, extraction with organic solvents and the like—in order to obtain a sufficiently pure preparation of nucleic acid. Extracts may be prepared using standard techniques in the art, for example, by chemical or mechanical lysis of the cell. Extracts then may be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. In some embodiments, the sample may comprise RNA, e.g., mRNA, collected from a subject sample, e.g., a blood sample. General methods for RNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). The contents of each of these references is incorporated by reference herein in their entirety. In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE Complete DNA and RNA Purification Kit (EPICENTRE, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

The disclosed methods and apparatus benefit from enriching a sample for a targeted nucleic acid using time-varying driving fields in conjunction with time-varying mobility-varying fields. This technique is known generally as Scodaphoresis, and is described in theoretical details, in addition to specific embodiments, in the following published patent documents, all of which are incorporated by reference in their entireties: U.S. Pat. Nos. 8,133,371 and 8,182,666, and US Published Application Nos. 2011/0048950, 2011/0272282, 2012/0048732, 2012/0295265, 2012/0329064, and 2013/0048487.

FIG. 1 shows schematically an apparatus 10 according to an example embodiment of the invention. Apparatus 10 comprises a medium 12 through which DNA or RNA can move under the influence of electrical fields. Embedded in the medium are probes for one or more mutations of interest (i.e. one or more types of probes). The probes may comprise, for example, short pieces of DNA having sequences complementary to the mutation(s) of interest. The probes are bonded to or otherwise immobilized in medium 12. A large number of probes of each type are immobilized in medium 12 such that DNA or RNA having a sequence complementary to one of the immobilized probe types will have the opportunity to bind to many instances of the complementary probe as the DNA or RNA moves through the medium. The medium, may, for example, comprise a gel, such as an agarose gel or a polyacrylamide gel. The probes may be covalently bonded to the gel, for example by using acrydite-modified oligonucleotides as the probes. The medium may be supported on a substrate 14. The substrate 14 may be configured for insertion into a scodaphoresis apparatus. In some embodiments the medium 12 is in the form of a thin layer on the substrate 14. The layer may, for example, have a thickness in the range of 10 to 200 μm. In some embodiments, apparatus 10 is in the form of a cassette (see, e.g., FIG. 3). The cassette may be sterile and provided with a seal that can be removed or broken to introduce a sample. The cassette may be labeled in one or both of human-readable indicia and machine-readable indicia with information about the cassette including identification of the probe(s) in the medium.

In some embodiments, the probes are selected to releasably bind to DNA coding for specific mutations in genes known to be relevant to the diagnosis, prognosis, treatment and/or monitoring of cancer. "Releasably binding" means that the DNA having a target sequence complementary to the probe will tend to anneal to the probe during one phase of scodaphoresis, and that DNA having a target sequence complementary to the probe will have a high probability of being unbound from the probe during another phase of scodaphoresis. For example, where scodaphoresis comprises cycling the temperature within the medium between a higher temperature and a lower temperature, DNA having a target sequence complementary to the probe may releasably bind to the probe during a phase where the medium at the location of the probe is at the lower temperature. The DNA having the target sequence may subsequently unbind from the probe during a phase where the medium at the location of the probe is at the higher temperature. Additionally, sequences that are not complimentary to the probe sequence will not bind to the probes in either the high or low temperature regime.

In some embodiments, a probe is selected to yield a particular melting temperature of the probe-target duplex. In some embodiments, the probes include one or more locked nucleic acid (LNA) bases within selected probes to increase the melting temperature of the selected probe-target duplex. In some embodiments, the probes include one or more bridged nucleic acid (BNA) bases within selected probes to increase the melting temperature of the selected probe-target duplex. In some embodiments, the probes can include a base that is a mismatched to both the mutant and wild-type sequences to yield a desired melting temperature.

In some embodiments, the probes are designed so that a difference in melting temperature between the probe and the mutant target sequence and between the probe and the wild type sequence is maximized. For example, in some embodiments, the probes are designed so that the difference in melting temperature between the probe and nucleic acids having the mutant target sequence and between the probe and nucleic acids having the wild type sequence is at least about 0.5° C. to 5.0° C., or any value there between e.g. about 1.0° C., 1.5° C., 2.0° C., 2.5° C., 3.0° C., 3.5° C., 4.0° C. or 4.5° C. In some embodiments, one or more locked nucleic acid (LNA) bases are used at selected position(s) within the probe to maximize the difference in melting temperature between the probe and the mutant target sequence and between the probe and the wild type sequence.

The methods and apparatus are generally applicable to enriching, isolating, detecting, and/or characterizing nucleic acid biomarkers. In some embodiments, the probes are selected to releasably bind to DNA coding for mutations in the BRAF, KRAS, EGFR, PIK3CA, ALK, APC, CTNNB1, IDH1, IDH2, NRAS, PTEN, TP53, PDGFRA, AKT1, HRAS, GNAQ, GNA11, KIT, ABL1, and/or MEK1 genes. A separation medium may be prepared with several, tens, twenties, or hundreds of different probes, thereby allowing simultaneous enrichment of many different nucleic acids. In some instances, the probes are related, for example, including a variety of single nucleotide polymorphisms in a known gene. In other instances, the probes will contain a variety of genes that relate to a single disease. In other instances, the probes will contain a variety of genes that relate to related diseases. In other instances, the probes will contain a variety of genes that relate to unrelated but common diseases. For example, in an embodiment, the separation medium can comprise probes selected to be complementary to DNA coding for the mutations associated with cancer, including any combination of mutations set forth in Table 1 in Appendix A or Table 2 in Appendix B. In general, the availability of commercial nucleic acids makes it possible to prepare separation media for apparatus 10 having probes of just about any combination.

Thus the invention makes it possible to screen, type, or diagnose, various types of cancer such as breast cancer, stomach and esophagus cancer, colorectal cancer, lung cancer, central nervous system cancer, thyroid cancer, pancreatic cancer, prostate cancer, head and neck cancer, skin cancer, bladder cancer, liver cancer, kidney cancer, gastric cancer, melanoma, sarcoma, gynecological (cervix, ovary, uterus) cancer, endometrial cancer, and/or different types of leukemia and lymphoma. Other panels of probes suitable for the diagnosis, prognosis, treatment and/or monitoring of other types of cancer can be devised by those skilled in the art using suitable probes intended to detect the presence of specific mutations in a sample, depending on the specific type of cancer being screened for (e.g. brain cancer, breast cancer, ovarian cancer, prostate cancer, lung cancer, skin cancer, and the like) and the purpose of the screening (e.g. diagnostic, prognostic, treatment selection, patient monitoring). Such panels of probes may include probes for other mutations and other genes, other than those listed in Tables 1 and 2.

In selected embodiments the number of probes immobilized in the medium is more than 10 or more than 20. In an example embodiment probes of 40 to 150 distinct types are immobilized in the medium, including e.g. 50, 60, 70, 80, 90, 100, 110, 120, 130 or 140 distinct types. Thus, more than 10, more than 20, or more than 100 different mutations can be screened for in one sample, depending on the number of probes used.

In some instances, it will be beneficial to enrich for and characterize only specific mutations whose presences suggests a high likelihood of disease. In such embodiments, the separation medium and apparatus is designed to enrich only this mutation (the "perfect match" or "target" sequence, i.e. "target particle") to be retained on the medium while all other similar nucleic acids (the "mismatch" sequence, i.e. "mismatch particle") are removed. In such embodiments, each probe may be an immobilized oligonucleotide with a sequence complementary to the target particle, but with a one base mismatch to the mismatch particle. In some such embodiments, the target sequence is a specific mutant sequence of a specific gene and the mismatch sequence is the wild type sequence of that gene. In other such embodiments, the target sequence is the wild type sequence of a specific gene and the mismatch is any sequence of that gene having a point mutation at a given location.

Figure 2:
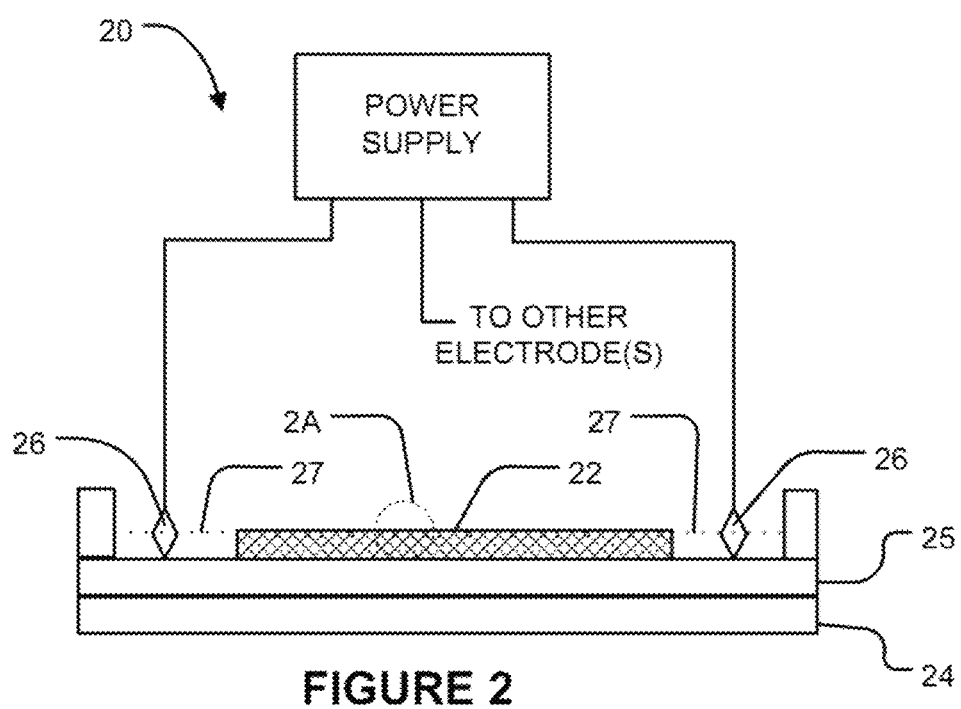
FIG. 2 is a schematic view of an exemplary Scodaphoresis apparatus.
Figure 2A:
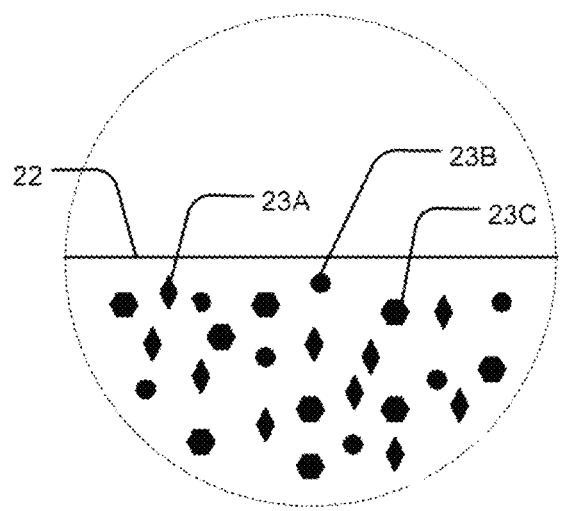
FIG. 2A is an enlarged view of a portion of the medium of the apparatus of FIG. 2.

FIG. 2 shows an example scodaphoresis apparatus 20. FIG. 2A schematically illustrates a highly magnified section of a medium 22 of apparatus 20 showing schematically probes 23A, 23B, 23C immobilized in medium 22. Probes 23A, 23B, 23C can be of any type discusses above, for example, relating to a specific mutation or a family of closely-related mutations. Apparatus 20 comprises a temperature-controlled plate 24 against which medium 22 can be placed. In the illustrated embodiment medium 22 is on a substrate 25 which sits against plate 24. Electrodes 26 are in electrical communication with medium 22. For example, each electrode 26 may contact an electrically-conductive buffer solution 27 that is in contact with medium 22. A power supply 28 is connected to the electrodes 26. Medium 22 and electrodes 26 are configured in such a manner that in three or more regions surrounding a focus location the direction and field strength of electrical fields in medium 22 may be controlled by applying different electrical potentials to the electrodes 26.

Figure 3:
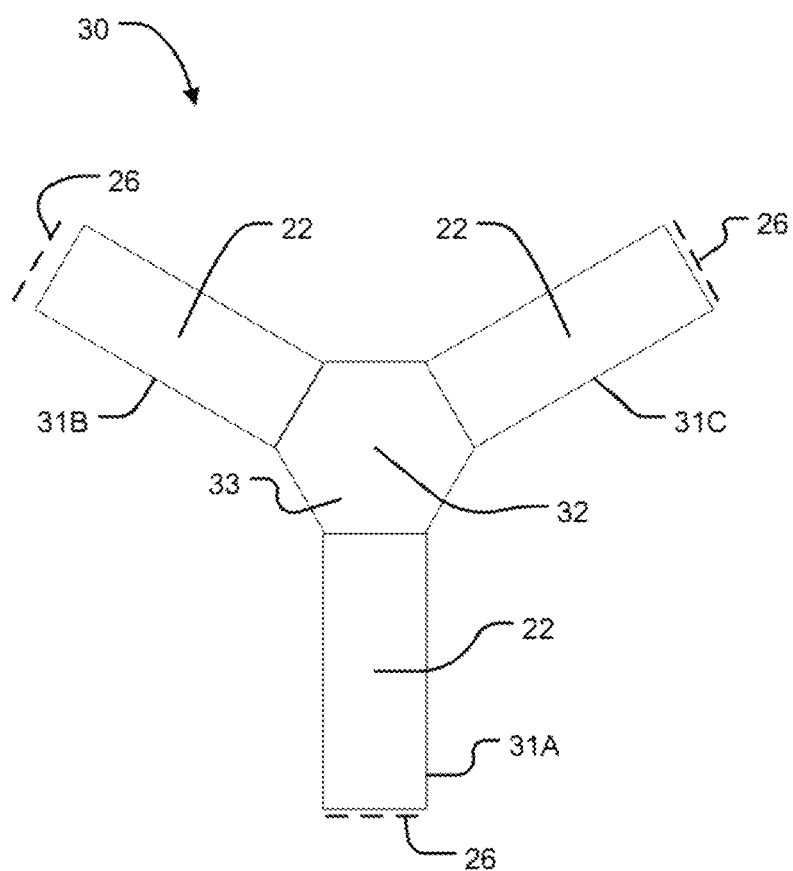
FIG. 3 depicts an embodiment of a Scodaphoresis apparatus having three arms and providing nucleic acid enrichment with time varying driving and mobility-varying fields.

In an embodiment, the enrichment is carried out with a scodaphoresis chip, similar to that shown in FIGS. 3B-F, and sold commercially by Boreal Genomics (Los Altos, Calif.). As shown in FIG. 3, an apparatus 30 having a medium 22 can be arranged with three arms 31A, 31B and 31C (collectively arms 31), each with an indexable electrode that is powered by a controller and supply (not shown). Apparatus like that illustrated in FIG. 3 is described in detail in U.S. patent application Ser. No. 13/739,337 filed 11 Jan. 2013, which is hereby incorporated herein by reference for all purposes.

Figure 3A:
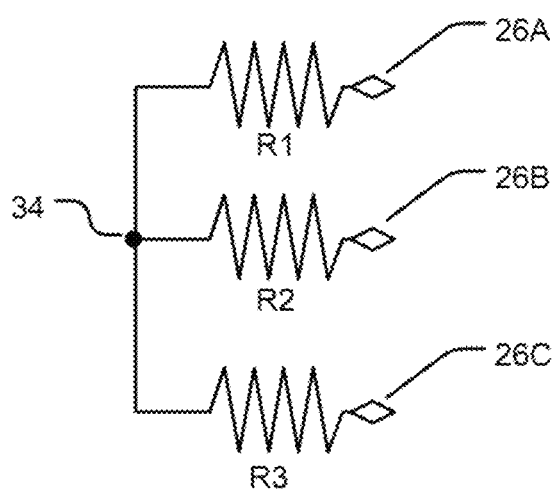
FIG. 3A shows an electrical circuit equivalent to the apparatus of FIG. 3.

One end of each arm 31 contacts a focus location 32. In the illustrated embodiment a well 33 containing a buffer solution is located at focus location 32. An opposing end of each arm 31 is in electrical communication with a corresponding electrode 26. An electrical circuit equivalent to apparatus 30 is illustrated in FIG. 3A in which resistors R1, R2 and R3 represent the three arms 31 and the node 34 represents the focus location 32. With this configuration, the electric field strength in one arm 31 can be made higher than the electric field strength in the other two arms 31. This can be done by applying equal or nearly equal electric potentials to the electrodes for the other two arms while applying an electric potential significantly different from the potentials of the other two electrodes to the electrode for the arm in which it is desired to have a higher electrical field strength. The directions of the electric fields can be reversed by altering the relative polarities of the electrodes. In an embodiment, a time-dependent voltage is applied to each electrode 26, resulting in a driving field that moves the targeted nucleic acids to a focus, where they can be recovered for further characterization. For example, with the embodiment of FIG. 3, by setting electrode 26A to have a potential of minus 100 volts and setting electrodes 26B and 26C to have potentials of 0 volts, one can create a situation in which arm 31A has an electric field strength twice as great as the electric field within arms 31B and 31C. Furthermore, in arm 31A, the electric field is directed toward the focus location (according to the convention that the direction of the electric field is from negative to positive) whereas in arms 31B and 31C the electric fields are directed away from the focus location.

During times of high electric field strength, the temperature of the medium 22 will be increased by resistive heating. Operating conditions can be selected to exploit the difference in melting temperature of oligonucleotides having a sequence that is the perfect match to the sequence of the immobilized probe and a mismatch sequence to the immobilized probe so that oligonucleotides having each sequence tend to experience net motion in opposite directions. In some embodiments, the thickness of the medium and its thermal contact with an underlying temperature-controlled substrate can be adjusted to control both the heating and cooling time of the gel with respect to the application of the electric field and the average temperature, and magnitude and phase, of the temperature fluctuations within the medium.

Figure 3B:
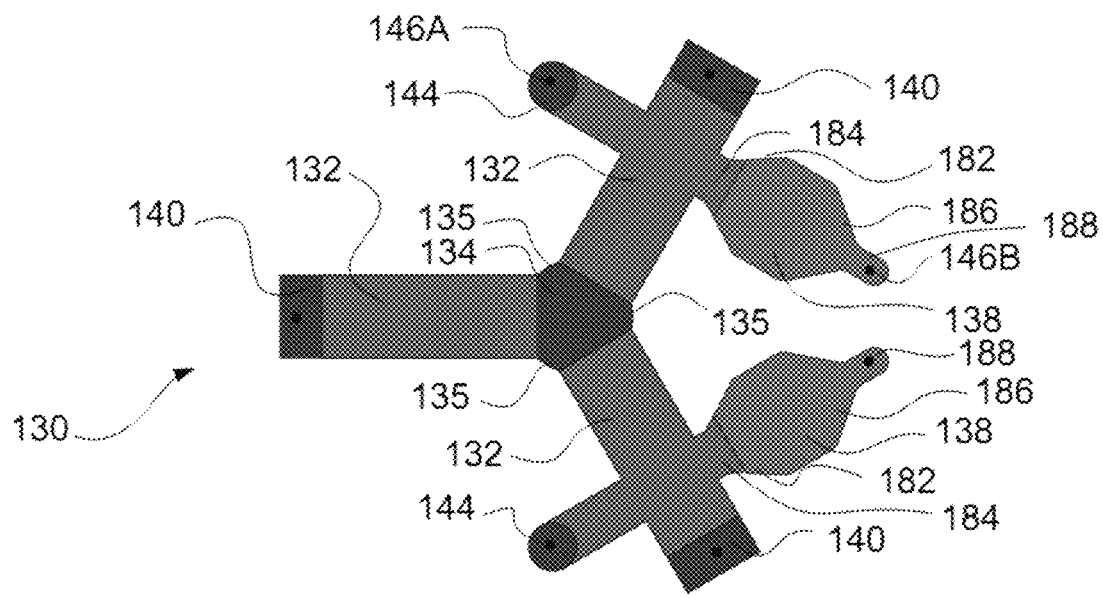
FIG. 3B shows an alternative embodiment of a Scodaphoresis apparatus having three arms and providing nucleic acid enrichment with time varying driving and mobility-varying fields.
Figure 3C:
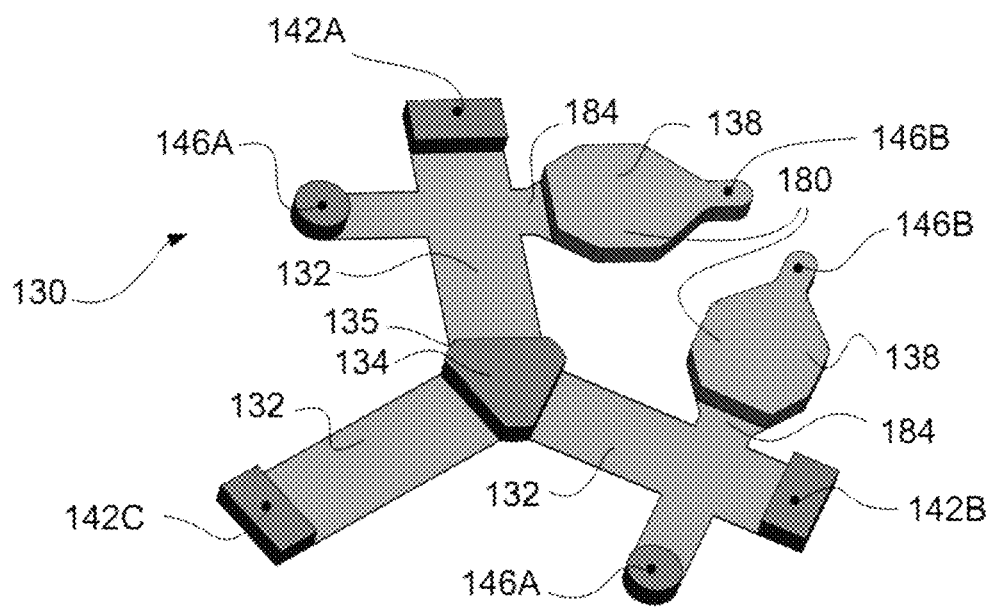
FIG. 3C shows an alternate view of the embodiment of FIG. 3C.
Figure 3D:
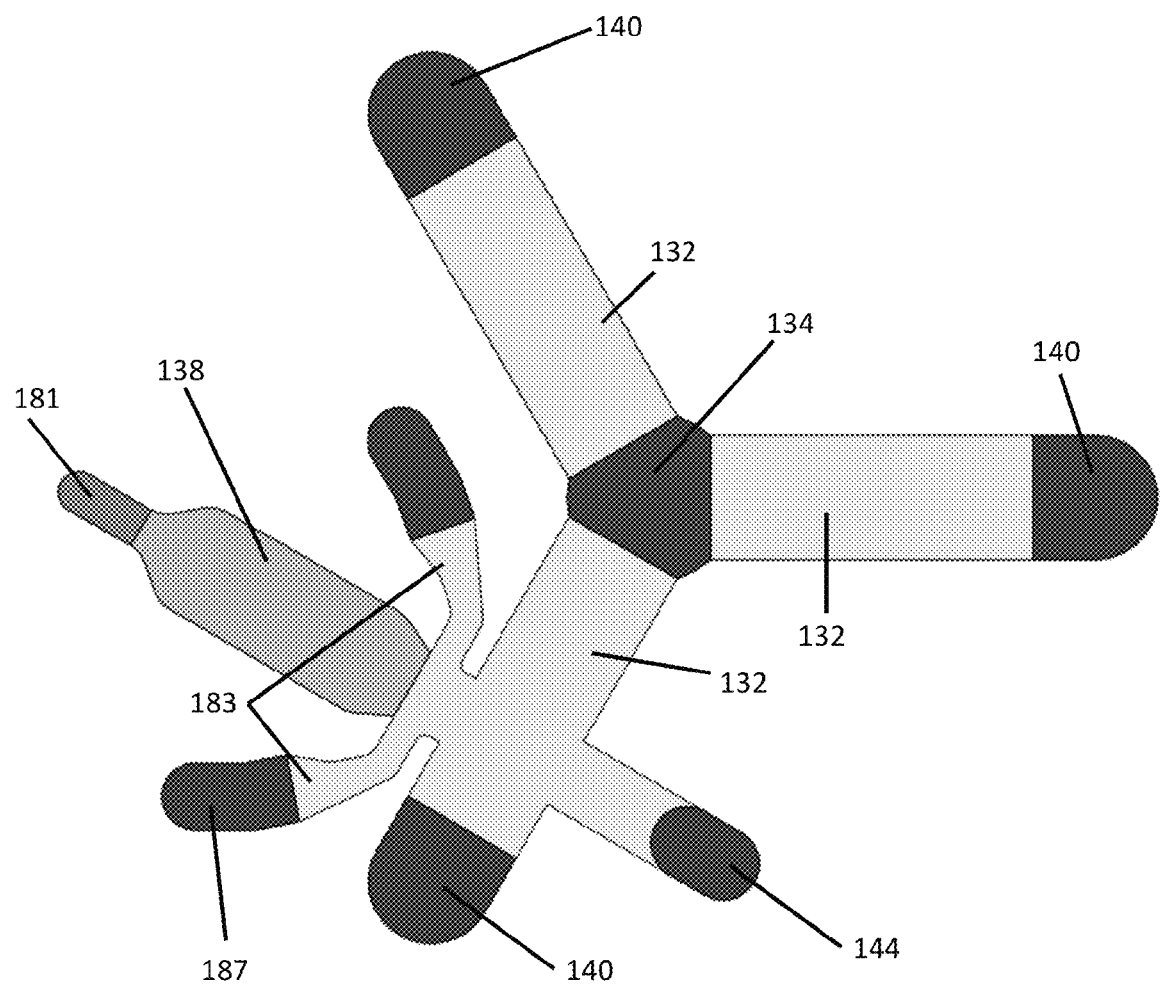
FIG. 3D shows an alternative embodiment of a Scodaphoresis apparatus having three arms and providing nucleic acid enrichment with time varying driving and mobility-varying fields.

FIGS. 3B-3D illustrate a second exemplary embodiment of an apparatus 130 that can be used with the disclosed methods. Portions of apparatus 130 that correspond in function to portions of apparatus 30 are indicated with like reference numerals incremented by 100. In the illustrated embodiment, separation arms 132 are disposed between a base plate 162 and a top plate 164 (FIG. 3F). Access apertures 168 (FIG. 3E) define portions of central reservoir 134, loading reservoirs 138, and buffer chambers 140 and 144. The depths of central reservoir 134, loading reservoirs 138, and buffer chambers 140 and 144 is thus defined in part by the thickness of top plate 164 (FIG. 3F). In the illustrated embodiment, central reservoir 134, loading reservoirs 138, and buffer chambers 140 and 144 are all deeper than the thickness of separation medium 136 (FIG. 3F).

In the illustrated embodiment, central reservoir 134 is of a generally triangular shape, with rounded or trimmed corners 135. Central reservoir 134 is shaped to minimize any potential distortions to the electric field used to move sample particles in arms 132.

In the illustrated embodiment of FIGS. 3C and 3D, loading reservoir 138 has a relatively wider middle portion 180. However, loading reservoir 138 can be of the same width as separation arms 132, as shown in FIG. 3D. In FIGS. 3B and 3C, tapered portion 182 narrows from middle portion 180 toward an injection surface 184 on separation arm 132. A second tapered portion 186 narrows from middle portion 180 toward an electrode chamber 188 for receiving a loading electrode, shown schematically as 146B. A separate loading buffer chamber 144 receives loading electrode 146A.

In some embodiments, loading of sample into the separation arms is enhanced. For example, in the embodiment illustrated in FIGS. 3B and 3C, loading reservoir 138 has a greater depth than the thickness of separation medium 136. Providing a loading reservoir 138 with a height greater than the thickness of separation medium 136 allows the sample volume to be increased, without making the surface area required for loading reservoir 138 unduly large. In other embodiments, as depicted in FIG. 3D, sample loading can be enhanced with the inclusion of electrical streamlines 183. Electrical streamlines 183 are in the same plane as the gel of separation arms 132, and help constrain the sample to a narrow physical window during injection. When used, a voltage is applied from the agarose dam 181 and electrical streamlines 183 to the electrode across the separation arm 132. When used to load nucleic acids, for example, the configuration in FIG. 3D reduces loading losses due to nucleic acid spreading upon injection. Such techniques are especially useful when evaluating high value samples, such as forensic crime samples, where any nucleic acid loss can skew the results.

Figure 3E:
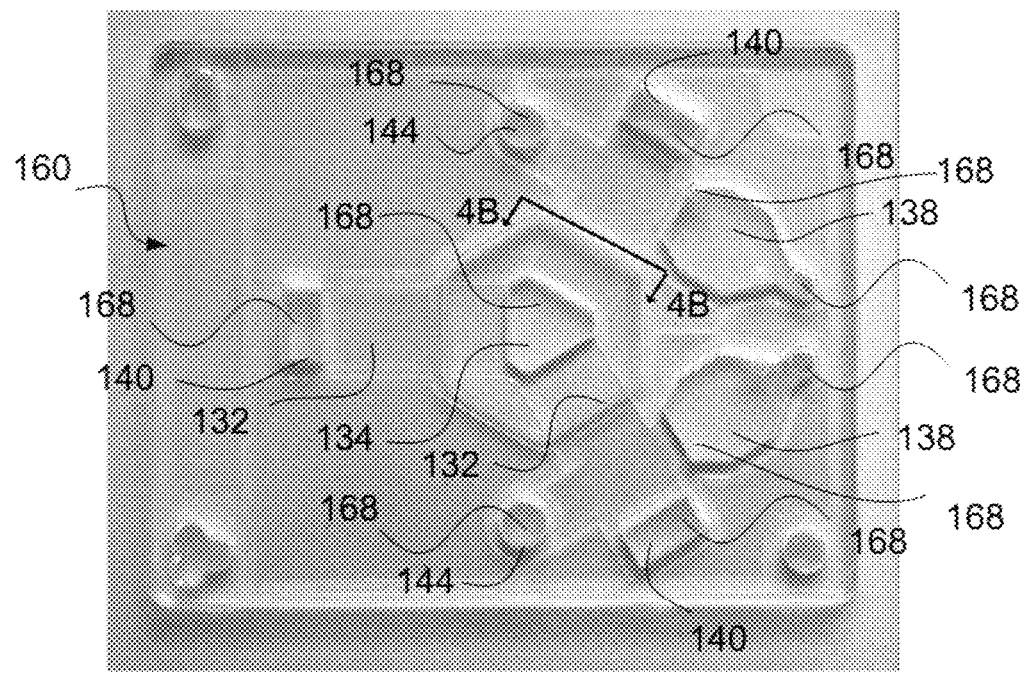
FIG. 3E shows is a top view of a photograph of a gel cassette for use with the apparatus of FIGS. 3B and 3C.
Figure 3F:
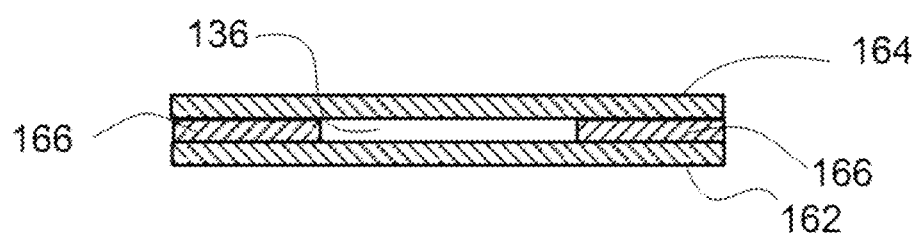
FIG. 3F is a schematic cross-sectional drawing of the cassette of FIG. 3E.

With reference to FIGS. 3E and 3F, in one embodiment a cassette 160 for use with apparatus 130 has a base plate 162 and a top plate 164. Plates 162, 164 may be made of any suitable non-electrically-conductive material, for example plastic, acrylic or glass. In embodiments in which temperature is used as the mobility altering field, at least one of base plate 162 and top plate 164 should be made from a material with good thermal conductivity, for example, glass.

Base plate 162 may be secured to top plate 164 in any suitable manner, for example by being integrally formed therewith, clamped thereto, secured thereto with an acceptable adhesive, or the like. In the illustrated embodiment of FIGS. 3E and 3F, base plate 162 is secured to top plate 164 using a layer of pressure sensitive adhesive 166. Pressure sensitive adhesive 166 maintains the spacing between base plate 162 and top plate 164. Pressure sensitive adhesive is cut to provide the desired configuration of separation medium 136. That is, portions of pressure sensitive adhesive 166 are removed where pressure sensitive adhesive 166 would otherwise interfere with separation arms 132, central reservoir 134, loading reservoir 138, electrode buffer chambers 140, loading buffer chambers 144, or the like. For example, where the separation medium is a gel such as polyacrylamide or agarose, pressure sensitive adhesive 166 can be cut to the desired shape, bonded between base plate 162 and top plate 164, and the gel can be poured in each separation arm 132. Where the separation medium is relatively thin, e.g. 100 µm, capillary action will draw the gel between plates 162, 164, and the gel will take on the shape defined by pressure sensitive adhesive 166. Access apertures 168 are provided in the top plate to provide access to loading reservoirs 138, central reservoir 134, to enable electrodes 140, 142, 146 to be inserted into the corresponding buffer chambers. In embodiments in which the gel is sufficiently thick that capillary action will not prevent the gel from entering loading reservoirs 138, central reservoir 134, electrode buffer chambers 140 or loading buffer chambers 144, suitable gel dams or other structures can be used to prevent the gel from flowing into these regions when being poured.

In the illustrated embodiment, the thickness of separation medium 136 is defined by the thickness of the layer of pressure sensitive adhesive 166. Separation medium 136 may have any desired thickness. In some exemplary embodiments, separation medium 136 is 100 µm thick. The thickness of separation medium 136 could be increased to increase the sample capacity of cassette 160. However, if separation medium 136 is made too thick, separation medium 136 will take longer to heat and cool (i.e. the thermal response time of separation medium 136 will be increased), which may be undesirable in some embodiments that use temperature as the mobility altering field. The thermal relaxation time of a separation arm filled with separation medium approximately 100 µm thick has been found to be on the order of ~200 ms in one exemplary embodiment. If separation medium 136 is made too thin, the capacity of cassette 160 may become undesirably low. The capacity of cassette 160 is determined by the volume of a sample to be loaded, the mass of charged target particle (e.g. DNA) to be loaded, and the concentration of electrically charged species (including salts) in the sample.

In some embodiments, a filter gel can be used upstream of a separation medium to reduce the level of contaminants present in a sample before target particles are subjected to separation, as well as to increase the capacity of the separation medium. The capacity of an apparatus can depend on all of the volume and salinity of a sample and the amount of charged target and contaminant particles present in a sample. That is, the capacity of an apparatus may be limited by any of the volume of a sample (a sample which is too large in volume may not be loaded), the salinity of a sample (i.e. the presence of too many ions may interfere with electrophoresis if the salinity of the sample is too high), or the amount of target particle in a sample (e.g. the presence of too much nucleic acid in the sample, whether target or contaminating sequence, may interfere with electrophoresis). A filter gel as described below allows for a larger volume of sample to be loaded, allows for the removal of excess ions in the sample during loading, and/or allows for the removal of particles similar in nature to the target particle but which do not interact as strongly with the immobilized affinity agent in the filter gel (e.g. for the removal of nucleic acids that have a sequence that is not similar to a target nucleic acid). In use, a filter gel can be positioned upstream of the separation apparatus, so that particles can be first loaded into the separation gel, and then loaded onto the separation apparatus.

A filter gel is a separation medium (for example agarose or polyacrylamide gel) that has an affinity agent immobilized therein. The affinity agent is selected to have a binding affinity for target particles of interest (e.g. oligonucleotides having a particular sequence). A sample is injected into the filter gel by application of an electric field under conditions such that the target particles of interest bind to the immobilized affinity agent (or alternatively the sample could be mixed with the filter gel when the filter gel is poured). Under the influence of the electric field, contaminating particles that do not bind to the affinity agent pass through the filter gel. In some embodiments, the contaminating particles can be removed via an exhaust gel downstream of the filter gel during sample loading, so that contaminating particles do not enter the separation medium.

After contaminating particles have passed through the filter, conditions are changed so that the target particles do not bind the affinity agent (e.g. the temperature is raised), and an electric field is applied to inject the target particles from the filter gel into the separation medium. A filter gel can be used together with any apparatus for conducting electrophoresis to reduce the level of contaminants present and/or to increase the capacity of the apparatus. For example, a filter gel could be provided upstream of a conventional electrophoresis gel used to separate oligonucleotides based on size. In preferred embodiments, the probes for each mutation have a density in the scodaphoresis medium sufficient that DNA affected by the mutation will encounter, bind to, and be released from corresponding probes many times in the course of being concentrated at the focus location.

In some embodiments, the probes used in the scodaphoresis medium are selected to be a perfect match for DNA molecules having the wild type sequence, but to have one or more mismatches for DNA molecules having a mutation. Operating conditions can be selected based on the difference in the melting temperature of the wild type sequence versus the mutant sequences for the immobilized probe so that DNA having the wild type sequence (i.e. a perfect complementary match for the immobilized probe) and background DNA (i.e. DNA having a sequence significantly different from the complement of the immobilized probe) is washed out of a distal end of the gel, while DNA having a mutant sequence (i.e. a sequence complementary to the immobilized probe but with one or more mismatches) is concentrated in a central portion of the medium (referred to as "wild-type rejection").

In this manner, DNA having mutations can be enriched in a sample, without a requirement to know specifically what mutation is present in the DNA or to provide a probe specific for each potential point mutation at a given location in the DNA sequence. In one exemplary test demonstrating wild type rejection, DNA having a BRAF wild-type sequence was separated from DNA having a single base mutation encoding for BRAF V600E using a scodaphoresis medium containing an immobilized probe complementary to the wild type sequence. Three different replicates collected 39.4%, 34.3% and 32.3%, respectively, of the loaded BRAF V600E DNA in the central extraction well, while the amount of loaded BRAF wild type DNA collected was only 0.107%, 0.105% or 0.137%, respectively (i.e. wild type rejection factors of 370 times, 328 times and 238 times, respectively).

Figure 4:
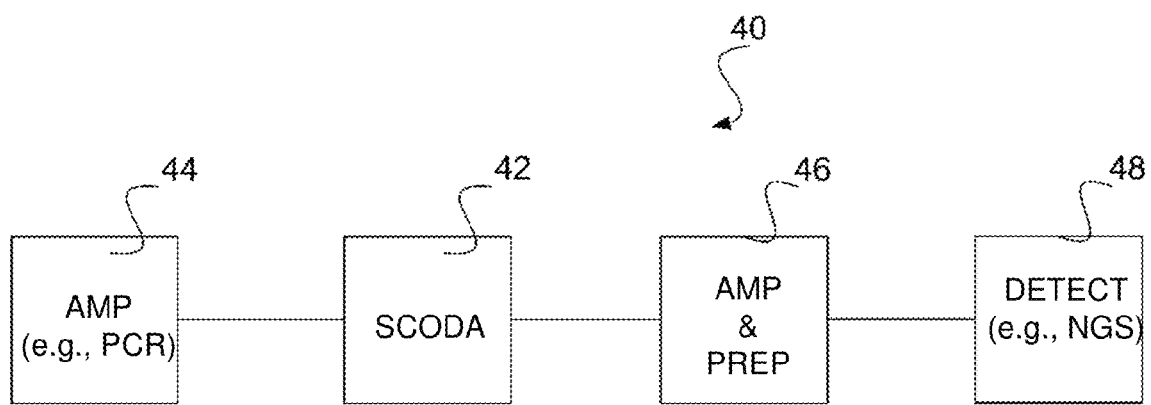
FIG. 4 is a schematic diagram of an apparatus according to one embodiment of the invention.

FIG. 4 illustrates apparatus 40 according to a further example embodiment of the invention. Apparatus 40 comprises scodaphoresis apparatus 42. Upstream from scodaphoresis apparatus 42 is a stage 44 of selective DNA amplification. Stage 44 advantageously exploits the polymerase chain reaction (PCR) to amplify DNA in regions of the genome containing the mutations to which the probes correspond. In some embodiments, stage 44 is a multiplexed PCR reaction, i.e. stage 44 includes a plurality of different of 5' and 3' primer pairs to amplify different regions of the genome. Because the products of the PCR reaction performed at stage 44 will be subject to purification by scodaphoresis and detection as described below, the plurality of different 5' and 3' primer pairs do not need to be differentiated from one another (e.g. it is not necessary to use different labels on the primer pairs or to select the primer pairs to produce differently-sized amplicons). Other forms of DNA amplification may be applied in place of PCR. For example, rolling circle amplification or multiple displacement amplification could also or alternatively be used at amplification stage 44.

A benefit of performing selective amplification using PCR is that the resulting strands of DNA to be processed by scodaphoresis apparatus 42 can be made uniform or nearly uniform in length. Examples of other amplification techniques that can be used to provide strands of DNA that are of uniform length under appropriate conditions include rolling circle amplification (RCA) and multiple displacement amplification (MDA). Producing DNA of uniform or nearly uniform length during amplification stage 44 can facilitate selective concentration of DNA that binds preferentially to any of the types of probes in the medium. Initial PCR amplification at stage 44 can also be used to attach bar codes and adaptors to the target DNA for eventual sample pooling and for compatibility with certain DNA sequencing methods.

Where stage 44 comprises PCR, PCR primers may be selected such that the amplified DNA corresponds to one or more sections of the DNA that may contain mutations corresponding to probes immobilized in a medium of scodaphoresis stage 42. In some embodiments, the PCR primers are selected to amplify portions of the genome at locations including the position of each of the mutations set forth in Table 1 (Appendix A) or Table 2 (Appendix B), or a subset of these mutations, or any other mutations of interest. In other embodiments, the amplification method can be selected to amplify portions of the genome including at least the position of each of the mutations that can be concentrated using immobilized probes present in the medium used to conduct scodaphoresis stage 42, including for example at least the position of each of the mutations set forth in Table 1 or Table 2, or a subset of those mutations, or any other mutations of interest.

In some embodiments where stage 44 comprises PCR, PCR primers are selected to produce an amplicon of at least 20 nucleotides in length. In some embodiments, PCR primers are selected to produce an amplicon of less than 1000 nucleotides in length. In some embodiments, the PCR primers are selected to produce an amplicon of between 30 nucleotides and 1000 nucleotides in length, or any value there between, e.g. 30, 40, 50, 60, 70, 80, 90, 100, 120, 150, 200, 250, 300, 350, 400, 450, 500, 550, 600, 650, 700, 750, 800, 850, 900 or 950 nucleotides in length. In some embodiments in which stage 44 is a multiplexed PCR stage, the PCR primer pairs used are selected to produce amplicons that are of approximately uniform length, e.g. that have a length that is the same to within ±2 bases, ±5 bases, or ±10 bases. The yield of scodaphoresis stage 42 is improved in some embodiments if the target DNA on which scodaphoresis is conducted is of relatively uniform length.

In some embodiments, the PCR technique used to conduct amplification stage 44 is suitable for amplification of short fragments (i.e. fragments having a length of 50 bases or less, e.g. 40 bases, 30 bases or 20 bases), and/or another technique is used to render short fragments of nucleic acids, for example as short as 20 bases in length, in the sample suitable for amplification by PCR.

In some embodiments, molecular inversion probes (MIP) are used in amplification step 44. MIPs are designed to anneal next to the mutation or SNP of interest in the genomic DNA sample, and then the mutation or SNP is incorporated into the MIP, for example by gap filling using DNA polymerase followed by ligation. The MIP can then be denatured from the genomic DNA and a target region within the MIP can be amplified using PCR. In some embodiments in which MIPs are used, the target genomic DNA only needs to be as long as the primers on the ends of the MIP probe (approximately 30-40 bases total).

In some embodiments, an enzymatic reaction such as ligation is used to convert a short nucleic acid target fragment into a larger fragment that can be more easily amplified. In one exemplary embodiment, the target nucleic acid fragment is 20 bases or more in length, and ligation or amplification with extended primers is used to increase the length of the target nucleic acid fragment to e.g. 40, 50, 60, 70, 80, 90 or 100 bases in length prior to amplification or detection.

In some embodiments, the yield of scodaphoresis stage 42 is improved if the target DNA fragments on which scodaphoresis is conducted are of relatively shorter length. Amplifying short fragments can facilitate amplification of a greater portion of the nucleic acids in the sample; for example, the shorter the amplicon, the less likely there will be random shearing of that amplicon in the starting sample.

In some embodiments, linear PCR is conducted at amplification stage 44, either alone or together with conventional PCR. Linear PCR produces single-stranded products. The preferential production of single-stranded target can be beneficial in scodaphoresis stage 42 as the complementary DNA strands would not be present to re-anneal to the target DNA strands.

Advantageously, amplification stage 44 may be configured to include only a few cycles of PCR or other amplification method. Amplification stage 44 may be selected such that if DNA containing mutations is present in a sample then that DNA will be amplified enough to be detected after scodaphoresis. Limiting the amplification provided by stage 44 can significantly reduce the likelihood that stage 44 will create mutations not otherwise present in the sample (which would increase the risk of a false positive result).

In some embodiments, amplification stage 44 is selected to amplify DNA sufficiently to compensate for losses in scodaphoresis stage 42. For example, if scodaphoresis stage 42 has an efficiency of 60% (meaning 60% of the DNA in a sample that has a specific mutation will be concentrated and presented at the output of scodaphoresis stage 42) then amplification stage 44 may be configured to ensure that if any DNA having the mutation is present in the sample then there is a high likelihood (e.g. greater than 90% or 95% or 99% or 99.9%) that a detectable quantity of DNA having the mutation will be present at the output of scodaphoresis stage 42. In some embodiments, this can be achieved with a few cycles (e.g. less than 15 cycles, including 11, 12, 13 or 14 cycles) of PCR. In some embodiments, amplification stage 44 comprises 4 to 10 cycles of PCR or any number there between, e.g. 5, 6, 7, 8 or 9 cycles. In some embodiments, amplification at stage 44 may include 16, 17, 18, 19 or 20 cycles of PCR.

In some embodiments, amplification stage 44 is configured to provide sufficient amplification such that the output of amplification stage 44 can be diluted prior to entering scodaphoresis stage 42. Dilution of the output of amplification stage 44 can reduce the amount of template DNA entering scodaphoresis stage 42. Excess template DNA may cause performance degradation in stage 42.

In some embodiments, further processing of the sample is carried out either before or after amplification stage 44. For example, ligation reactions or extension reactions can be conducted that do not amplify the target nucleic acid in the sample, but change the nature of the target nucleic acid. For example, DNA may be converted from double-stranded to single-stranded, the length of target nucleic acid molecules may be adjusted, and/or sequences relevant to downstream processing can be attached to the target nucleic acid molecules. In some embodiments, barcoded sequencing adaptors are coupled to target nucleic acid molecules through ligation.

In some embodiments, a first unique barcode sequence is coupled to the target nucleic acid molecules in a sample obtained from a first subject using ligation after amplification stage 44, a second unique barcode sequence is coupled to the target nucleic acid molecules in a sample obtained from a second subject using ligation after amplification stage 44, and so on for samples obtained from other subjects, so that multiple samples can be processed together in downstream steps. In some embodiments, the unique barcode sequences are included in the primers used to conduct the amplification step, and thus the barcode sequences are incorporated into the amplified target nucleic acid molecules during the process of amplification. In some embodiments, the unique barcode sequence used is the same for all target nucleic acid molecules in a sample obtained from a particular patient. In some embodiments, one or more different unique barcode sequences are used to identify the target nucleic acid molecules in a sample obtained from a particular patient.

In some embodiments, the amplification conducted at amplification stage 44 produces a double stranded DNA product. The double stranded DNA is then converted to single stranded DNA through any suitable method, including e.g. linear PCR or heating, prior to scodaphoresis stage 42. In some embodiments, suitable positive and/or negative controls are added to a sample prior to amplification stage 44.

In some embodiments, prior to amplification stage 44, a sample is assayed for nucleic acid content or for the abundance of specific sequences to provide a baseline reading of how much wild-type DNA is present in the sample. Any of detection schemes 48 may be applied in a fraction of the sample prior to amplification stage 44 to also rapidly determine which samples have substantial mutations, thus extending the dynamic range in mutation quantification of the system. In some embodiments, the detectable range of abundance of mutant nucleic acid to wild type nucleic acid is between 0.01% to 100% abundance of nucleic acid having the mutant sequence. In some embodiments, the detectable range of abundance of mutant nucleic acid to wild type nucleic acid is as low as 0.001%, or lower in some embodiments. In some embodiments where sufficient nucleic acid is present in the sample, amplification stage 44 is not conducted and the prepared sample is passed directly to scodaphoresis stage 42 without amplification.

Apparatus 40 has a further DNA amplification stage 46 after scodaphoresis stage 42. DNA amplification stage 46 may comprise a further application of PCR to amplify any DNA that passes scodaphoresis stage 42. Because scodaphoresis stage 42 can be configured to not pass wild type DNA, the output of scodaphoresis stage 42 is greatly depleted in wild type DNA as compared to the original sample. Therefore PCR errors which create mutations of wild type DNA are relatively unlikely to produce more mutant PCR products than is amplification of template mutant DNA strands obtained from scodaphoresis phase 42.

DNA amplification stage 46 is followed by a detection stage 48. Detection stage 48 may provide either or both of a qualitative or quantitative evaluation as to the presence of selected mutations. In some example embodiments, detection stage 48 comprises application of mass spectrometry, microarray techniques, DNA sequencing (e.g. Sanger sequencing or next generation sequencing, single molecule sequencing, including nanopore-based sequencing, sequencing by synthesis approaches, pyrosequencing, or sequencing by hydrogen ion release detection), quantitative PCR, and/or combinations thereof to detect mutated DNA sequences. In some embodiments, single base extension, ion semiconductor sequencing, or personal sequencing techniques, such as SNaPshot™, IonTorrent™, or MiSeq™ techniques are used at detection stage 48.

After enrichment and/or amplification, various methods and combination of techniques such as sequencing and array based technologies may be used to determine the sequence of the nucleic acids, and/or the level of nucleic acid expression, and/or nucleic acid copy number.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

One example of a sequencing technology that can be used in the methods of the provided invention is Illumina sequencing (e.g., the MiSeq™ platform), which is a polymerase-based sequence-by-synthesis that may be utilized to amplify DNA or RNA. Illumina sequencing for DNA is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. When using Illumina sequencing to detect RNA the same method applies except RNA fragments are being isolated and amplified in order to determine the RNA expression of the sample.

Another example of a DNA sequencing technique that may be used in the methods of the provided invention is Ion Torrent™ sequencing, offered by Life Technologies. See U.S. patent application numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In Ion Torrent™ sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton (H$^+$), which signal detected and recorded in a sequencing instrument. The signal strength is proportional to the number of nucleotides incorporated.

Another example of a DNA and RNA sequencing technique that can be used in the methods of the provided invention is 454™ sequencing (Roche) (Margulies, M et al. 2005, Nature, 437, 376-380). 454™ sequencing is a sequencing-by-synthesis technology that utilizes also utilizes pyrosequencing. 454™ sequencing of DNA involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed. In another embodiment, pyrosequencing is used to measure gene expression. Pyrosequecing of RNA applies similar to pyrosequencing of DNA, and is accomplished by attaching applications of partial rRNA gene sequencings to microscopic beads and then placing the attachments into individual wells. The attached partial rRNA sequence are then amplified in order to determine the gene expression profile. Sharon Marsh, *Pyrosequencing®* *Protocols in Methods in Molecular Biology*, Vol. 373, 15-23 (2007).

Another example of a DNA and RNA detection techniques that may be used in the methods of the provided invention is SOLiD™ technology (Applied Biosystems). SOLiD™ technology systems is a ligation based sequencing technology that may utilized to run massively parallel next generation sequencing of both DNA and RNA. In DNA SOLiD™ sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In other embodiments, SOLiD™ Serial Analysis of Gene Expression (SAGE) is used to measure gene expression. Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997, the contents of each of which are incorporated by reference herein in their entirety).

Another sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ Sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a sequencing technology that may be used in the methods of the provided invention includes the single molecule, real-time (SMRT) technology of Pacific Biosciences to sequence both DNA and RNA. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated. In order to sequence RNA, the DNA polymerase is replaced with a with a reverse transcriptase in the ZMW, and the process is followed accordingly.

Another example of a sequencing technique that can be used in the methods of the provided invention is nanopore sequencing (Soni G V and Meller, AClin Chem 53: 1996-2001) (2007). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Additional detection methods can utilize binding to microarrays for subsequent fluorescent or non-fluorescent detection, barcode mass detection using a mass spectrometric methods, detection of emitted radiowaves, detection of scattered light from aligned barcodes, fluorescence detection using quantitative PCR or digital PCR methods. A comparative nucleic acid hybridization array is a technique for detecting copy number variations within the patient's sample DNA. The sample DNA and a reference DNA are differently labeled using distinct fluorophores, for example, and then hybridized to numerous probes. The fluorescent intensity of the sample and reference is then measured, and the fluorescent intensity ratio is then used to calculate copy number variations. Methods of comparative genomic hybridization array are discussed in more detail in Shinawi M, Cheung S W *The array CGH and its clinical applications*, Drug Discovery Today 13 (17-18): 760-70.

Another method of detecting DNA molecules, RNA molecules, and copy number is fluorescent in situ hybridization (FISH). In Situ Hybridization Protocols (Ian Darby ed., 2000). FISH is a molecular cytogenetic technique that detects specific chromosomal rearrangements such as mutations in a DNA sequence and copy number variances. A DNA molecule is chemically denatured and separated into two strands. A single stranded probe is then incubated with a denatured strand of the DNA. The signals stranded probe is selected depending target sequence portion and has a high affinity to the complementary sequence portion. Probes may include a repetitive sequence probe, a whole chromosome probe, and locus-specific probes. While incubating, the combined probe and DNA strand are hybridized. The results are then visualized and quantified under a microscope in order to assess any variations.

In another embodiment, a MassARRAY™-based gene expression profiling method is used to measure gene expression. In the MassARRAY™-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059 3064 (2003).

Further PCR-based techniques include, for example, differential display (Liang and Pardee, Science 257:967 971 (1992)); amplified fragment length polymorphism (iAFLP) (Kawamoto et al., Genome Res. 12:1305 1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); Beads Array for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888 1898 (2001)); and high coverage expression profiling (HiCEP) analysis (Fukumura et al., Nucl. Acids. Res. 31(16) e94 (2003)). The contents of each of which are incorporated by reference herein in their entirety.

In certain embodiments, variances in gene expression can also be identified, or confirmed using a microarray techniques, including nylon membrane arrays, microchip arrays and glass slide arrays, e.g., such as available commercially from Affymetrix (Santa Clara, Calif.). Generally, RNA samples are isolated and converted into labeled cDNA via reverse transcription. The labeled cDNA is then hybridized onto either a nylon membrane, microchip, or a glass slide with specific DNA probes from cells or tissues of interest. The hybridized cDNA is then detected and quantified, and the resulting gene expression data may be compared to controls for analysis. The methods of labeling, hybridization, and detection vary depending on whether the microarray support is a nylon membrane, microchip, or glass slide. Nylon membrane arrays are typically hybridized with P-dNTP labeled probes. Glass slide arrays typically involve labeling with two distinct fluorescently labeled nucleotides. Methods for making microarrays and determining gene product expression (e.g., RNA or protein) are shown in Yeatman et al. (U.S. patent application number 2006/0195269), the content of which is incorporated by reference herein in its entirety.

In some embodiments, mass spectrometry (MS) analysis can be used alone or in combination with other methods (e.g., immunoassays or RNA measuring assays) to determine the presence and/or quantity of the one or more biomarkers disclosed herein in a biological sample. In some embodiments, the MS analysis includes matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated by reference herein in their entirety.

In some embodiments the presence and/or relative abundance of a plurality of different mutations are detected in detection stage 48. In some embodiments, the quantitative amount of one or more mutations in a sample is determined relative to an internal positive control, or relative to a housekeeping gene such as GAPDH in detection stage 48. In some embodiments, scodaphoresis stage 42 is configured to selectively concentrate DNA molecules having mutant sequences while rejecting DNA molecules having wild-type sequences. In some such embodiments, after scodaphoresis stage 42, a known amount of DNA molecules having the wild-type sequence(s) is added to the sample as a positive control that aids quantitation of mutation in the final assay. For example, an amount of DNA having the wild-type sequence equal to 0.01% of the original amount of DNA present in the sample may be added such that a mutation comprising 0.01% of the original DNA would appear to be at the same signal amplitude as the wild-type positive control at detection stage 48.

In some embodiments, decisions about which drug to administer to a particular patient are made based on the identity of specific mutations detected in detection stage 48 and/or the relative abundance of some or all of those specific mutations. In some embodiments, the selected drug is then administered to the patient in a therapeutically effective amount.

Figure 5:
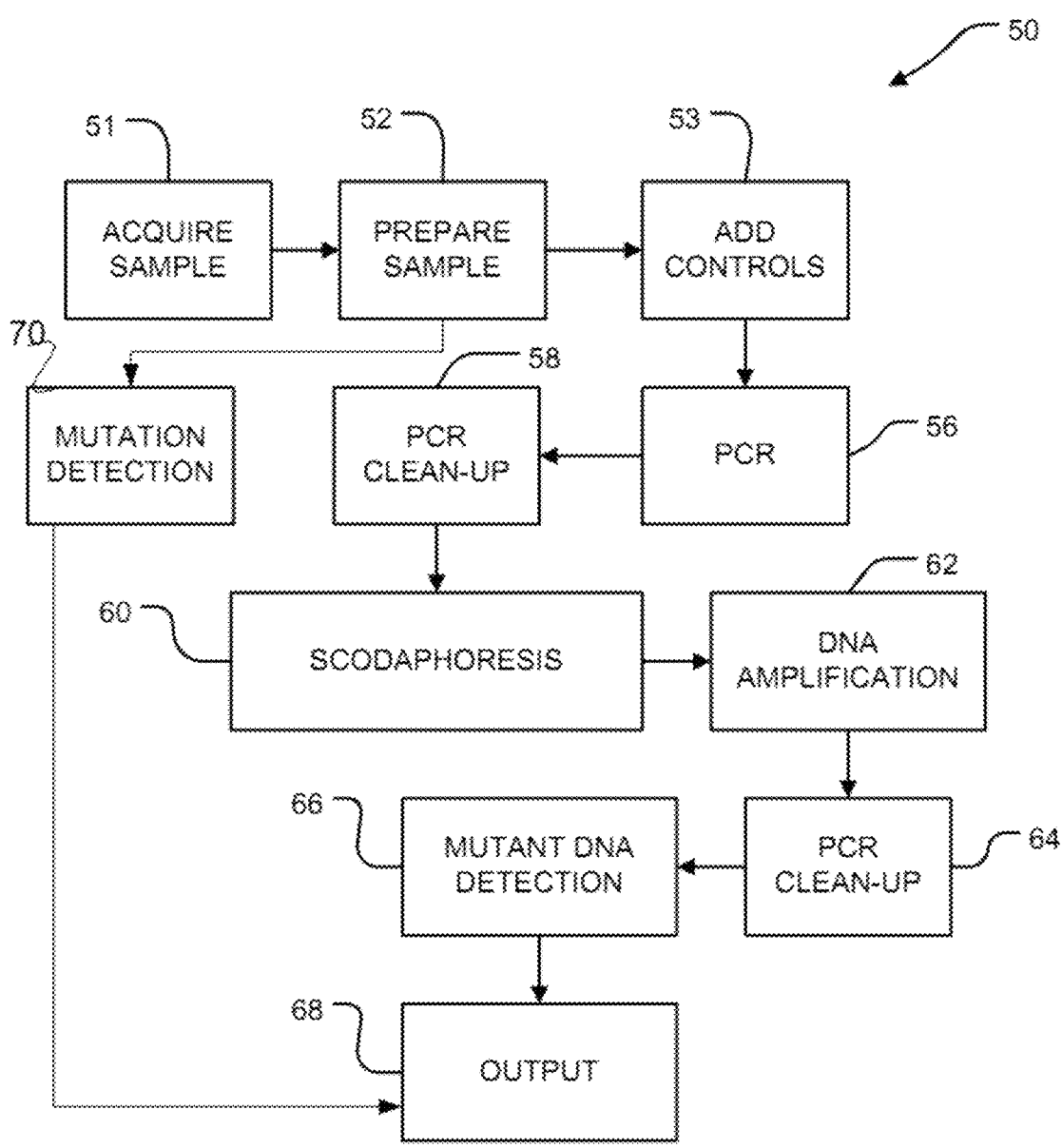
FIG. 5 shows a method for detecting DNA mutations in biological samples according to one embodiment of the invention.

FIG. 5 shows a method 50 for measuring and/or detecting DNA mutations in biological samples according to a more detailed example embodiment. A biological sample is obtained or provided at block 51. The biological sample may, for example, comprise a liquid sample, such as a sample of blood or plasma, a tissue sample, or the like. A tissue sample may be a fresh sample or preserved. For example, in some embodiments the sample comprises a formalin-fixed paraffin-embedded (FFPE) sample. In some embodiments, a tissue sample or blood sample is obtained from a patient in any suitable manner, e.g. by withdrawing blood, excising a portion of a tumor, or the like. In some embodiments, the sample is blood, whole blood, blood plasma, serum, stool, urine, saliva, tissue or any other sample containing biological material of the patient.

Sample preparation is performed in block 52. Sample preparation may, for example, comprise homogenizing the sample and lysing cells, if required, and removing from the sample and/or neutralizing contaminants and factors that could inhibit DNA amplification. For example, in some embodiments, blood plasma is the sample and lysing cells is not necessary. In some embodiments, the sample is whole blood and cells are lysed to capture all DNA sequences in the sample, including those present in cells. In some embodiments, block 52 includes enzymatic degradation of certain nucleic acids and/or proteins. In some embodiments, block 52 includes mechanical or other shearing of longer DNA fragments to reduce their overall size. Block 52 may include, for example, applying a Qiagen™ circulating nucleic acid kit or Qiagen™ FFPE kit available from Qiagen Inc. of Valencia, Calif., USA in cases where the sample comprises plasma or an FFPE tissue sample, respectively. In some embodiments, amplification may be performed directly on cell lysates without further purification. In some embodiments, total nucleic acids in the sample are quantified following sample preparation. For example, a NanoDrop™ spectrophotometer or quantitative PCR can be used to quantify total nucleic acids.

In some embodiments, an aliquot of the sample is removed for further analysis as a control at block 70. For example, real time PCR can be used to measure the number of genome copies present in the extracted DNA. The presence of suitable housekeeping genes such as GAPDH can be used for this purpose. In some embodiments, the presence of two or more controls is measured to quantify the number of genome copies present in the extracted DNA. In some embodiments, the lengths of the nucleic acid fragments that are selected as controls are selected so that at least one of the controls is a shorter fragment than the target fragments concentrated during scodaphoresis stage 60, and so that at least one of the controls is a longer fragment than the target fragments concentrated during scodaphoresis stage 60. The yield can be measured for a range of nucleic acid fragment lengths, as would be present in the sample.

In some embodiments, any of the detection methods described below with reference to block 66 can be used at block 70 in an initial mutation detection step. Initial mutation detection at block 70 can be used to quantitatively assess the abundance of mutations that are present at a high level (i.e. at a level within the detection range of the selected detection method) within the sample. Output from block 70 feeds into block 68 where all data is considered to provide a quantitative measure of one or more mutations in the sample. Combining data from an initial mutation detection step at block 70 and detection step 66 can expand the dynamic range of a selected detection method. For example, a particular detection method may be able to reliably detect mutations with a mutant abundance ranging from 1% to 100% of the sample, or from 0.1% to 10% of the sample, but not from 0.1% to 100% of the sample. As one example, for a detection method with a dynamic range of from 1% to 100% of a sample, a mutation with an abundance of from 1% to 100% could be detected in an initial mutation detection step at block 70, whereas a mutation with an abundance of from 0.01% to 1% abundance could be detected at detection step 66 following wild-type depletion at scodaphoresis stage 60 and spiking with suitable controls prior to detection step 66 (e.g. adding a known amount of DNA having the wild type sequence). In this example, the dynamic detection range of method 50 could span the range of 0.01% to 100%.

Block 53 comprises optionally introducing controls for a subsequent nucleic acid amplification reaction. The controls permit proper functioning of the amplification reaction to be verified. The controls may include positive controls and/or negative controls. In some embodiments, controls including a known abundance of a mutation, e.g. 0.1%, are added.

In block 56 an amplification step is performed. In some embodiments, exponential PCR is performed in block 56. In block 56 PCR may be performed for a limited number of cycles, e.g. less than 15 cycles or less than 20 cycles, including 11, 12, 13, 14, 15, 16, 17, 18, 19 or 20 cycles. In an example embodiment, 4-10 cycles of exponential PCR or any number there between, e.g. 5, 6, 7, 8 or 9 cycles, are carried out in block 56. In another example embodiment, 7 cycles of exponential PCR are carried out in block 56. Primers used in the PCR of block 56 may be selected to selectively amplify a portion of the genome in which the mutations of interest are located.

In some embodiments, amplification step 56 includes linear PCR, either alone or in combination with exponential PCR. In some embodiments, the linear PCR is performed for a limited number of cycles, e.g. 4-20 cycles, or any number there between, e.g. 5, 6, 7, 8, 9, 10, 11, 12, 13, 14, 15, 16, 17, 18, 19 or 20 cycles. In some embodiments, amplification step 56 includes rolling circle amplification (RCA) or multiple displacement amplification (MDA). In some embodiments where step 56 is a multiplexed amplification step, the different primer pairs used in the PCR of block 56 are selected to produce amplicons that are of approximately the same length, e.g. a length that is the same with a range of variation of only about 2 bases, 5 bases, 10 bases or about 20 bases in length. In some embodiments, the different primer pairs used in the PCR of block 56 are selected to have a melting temperature that is approximately the same for each primer, or that varies by only a small amount, e.g. ±2° C. or ±5° C.

In some embodiments, the PCR primers are selected to produce an amplicon of less than 1000 nucleotides in length. In some embodiments, the PCR primers are selected to produce an amplicon of between 20 nucleotides and 1000 nucleotides in length, or any value there between, e.g. 30, 40, 50, 60, 70, 80, 90, 100, 120, 150, 200, 250, 300, 350, 400, 450, 500, 550, 600, 650, 700, 750, 800, 850, 900 or 950 nucleotides in length. In some embodiments, the PCR primers are selected to be between 17 and 20 bases in length, and to be separated by only a few bases on the target sequence, such that the resulting amplicon is between 30 and 50 bases in length, including any length there between, e.g. 35, 40 or 45 bases.

In some embodiments, the PCR primers include adaptor sequences that may be used for subsequent amplification and incorporation of indices and DNA sequencing adaptor sequences. The PCR primers may also include sequences that contain the complementary sequence to primers used in a downstream amplification step, such as SNaPshot™ primers. In some embodiments, the PCR primers include a sequence that reconstructs the original gene sequence near the mutation to allow detection probes to bind to the reconstructed target following amplification.

In some embodiments, further modification of target DNA prior to or after amplification stage 56 is conducted. In some embodiments, target DNA strands are extended and/or adaptors or indices are attached to the target DNA strands as may be desired to facilitate further processing of the sample. In some embodiments, adaptors or indices are attached to the target DNA strands by using Y-adaptors, molecular inversion probes (MIP), ligation, or other enzymatic or chemical methods. In some embodiments, unique identifiers such as unique sequences or barcodes are incorporated into target DNA during amplification stage 56, for example by including such sequences in primers used during amplification stage 56.

In some embodiments, amplification step 56 is designed to accommodate the entire volume of the output of sample preparation conducted in block 52. In some embodiments, the entire volume of the output of sample preparation is accommodated by using large PCR reactions. In some embodiments, the entire volume of the output of sample preparation is accommodated by using multiple PCR reactions that are pooled and loaded into scodaphoresis step 60.

In block 58 a PCR clean-up is optionally performed. PCR cleanup block 58 may, for example, remove controls and/or primers from the reaction products. In some embodiments, primers are removed by adding an enzyme that selectively degrades only the primers, for example ExoI. In some embodiments, enzymes in the reaction mix, including any enzymes added to degrade the primers, are inactivated by heating the sample for a sufficient length of time to inactivate and/or denature such enzymes. In some embodiments, PCR is conducted using a commercial PCR clean-up kit, e.g. as can be obtained from Qiagen™. In some embodiments, the buffer that is used to elute the DNA from the PCR clean-up kit is selected to be compatible with the subsequent scodaphoresis step. In some embodiments, a buffer exchange is performed so that the buffer is compatible with the subsequent scodaphoresis step. In some embodiments, the PCR products are diluted into a suitable buffer to provide an ultimate buffer composition that is compatible with the subsequent scodaphoresis step. For example, the PCR products may be eluted from a PCR clean-up column in distilled water, and then a concentrated buffer solution can be added to yield a final salt concentration suitable for conducting scodaphoresis. In some embodiments, the buffer is selected to have or is treated to adjust the buffer so that the electrical conductivity of the buffer is between 1 and 20 mS/cm, or any value there between, e.g. 2, 4, 6, 8, 10, 12, 14, 16 or 18 mS/cm.

PCR cleanup block 58 may also separate strands of DNA to provided single-stranded DNA for a subsequent scodaphoresis step. In some embodiments, strands of DNA can be separated by increasing a temperature of the sample, e.g. to boiling or to a sufficiently high temperature that the strands of DNA separate. In some embodiments, linear PCR is performed to produce single-stranded target DNA and a further step to provide single-stranded DNA is not required.

In some embodiments, no PCR cleanup is performed. In some such embodiments, the output of amplification step 56 is designed to be compatible with scodaphoresis step 60, e.g. the salinity and volume of the solution produced as a result of amplification step 56 is selected to be acceptable for input directly to scodaphoresis step 60. In some embodiments, PCR products are denatured by heating the sample in the loading chamber of the apparatus used to conduct scodaphoresis, for example to a temperature of 70° C.

In some embodiments, controls are added prior to scodaphoresis in block 60. Controls can be added to assist in the quantification of the abundance of a particular mutation or SNP in the original sample. In some embodiments, a known amount of DNA having a particular mutation or SNP, or a known amount of DNA having a wild type sequence is added prior to conducting scodaphoresis in block 60. The controls added prior to scodaphoresis can optionally be labelled, e.g. with a fluorescent label, to facilitate optical monitoring of the progress of scodaphoresis. In some embodiments, the control sequences are added before the limited number of amplification steps preceding scodaphoresis.

Figure 11:
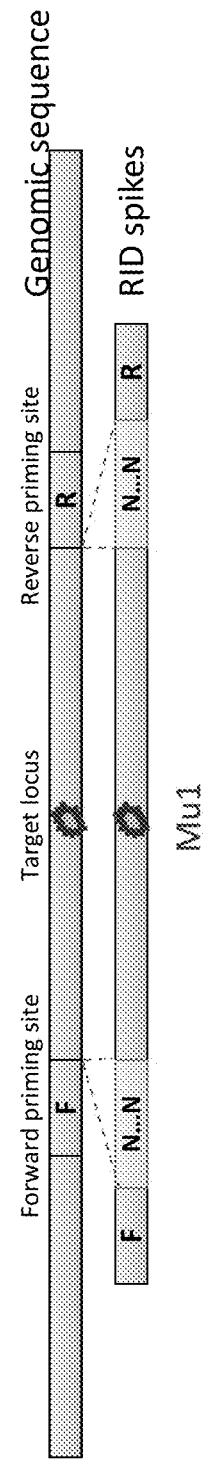
FIG. 11 illustrates control nucleic acids having random IDs that are used to track the amplification, enrichment, and characterization of targeted nucleic acids.

An exemplary control is shown in FIG. 11. The sequence of the control is identical to the target mutant sequence except for the addition of a number of degenerate bases ("N") just inside the primer section. The degenerate bases serve as Random IDs which can uniquely identify individual molecules, so that they can be identified at the conclusion of the workflow and used as a control to assure that the targeted mutant was enriched and characterized, and to establish a normalization factor in the event that quantitative analysis is (e.g., copy number) is desired. The number of degenerate bases should be large enough that for a given number of control nucleic acids, the chance of getting two molecules with the identical Random ID is low. For example, for 10 Ns in the degenerate sequence, there are approximately one million unique sequences. Thus, if 50 molecules are chosen at random, the chance of getting two with the same ID is 0.12%. In some embodiments, some of the control nucleic acids comprise sequences for COG5 and ALB, which are typically not part of a screening panel, but give information about the general fidelity of the workflow. In some embodiments, a sample is spiked with 50 copies of each control nucleic acid and 5000 copies of COG5 and ALB. In some embodiments, each control nucleic acid comprises five degenerate bases inside the forward and reverse primer sites, as shown in FIG. 11.

In some embodiments the control sequences provide an internal positive control. The control sequences should be amplified, enriched, and characterized identically to the targeted nucleic acids, and to the extent that the controls are not identified in the final characterization, all, or portions of, the assay should be suspect. Additionally, the control sequences can be used for internal quantification control. Because every input control sequence has a unique ID, the yield for the entire workflow can be calculated by counting how many times a given control sequence is read on the sequencer. Furthermore, once the yield is determined, it is possible to back-calculate the amount of a targeted nucleic acid that was in the starting material. This calculation can be done for every mutation and for every sample, even when the samples are multiplexed through enrichment and/or sequencing. Finally, it is not necessary to know ahead of time exactly how many copies of each control sequence were spiked in to the sample, because this can be measured by counting the number of unique random ID sequences. (It is, however, important to spike nominally x copies (within a factor of ~2), where x is determined by the number of degenerate bases per molecule, to avoid choosing two molecules with the same random ID and to utilize sequencing bandwidth efficiently.)

Block 60 comprises selectively concentrating DNA having selected mutations by scodaphoresis. In preferred embodiments the DNA comprising mutations is concentrated into a well containing a buffer. In some embodiments in which more than one mutation is selected for using scodaphoresis, the oligonucleotide probes contained within the medium used to conduct scodaphoresis are selected to have similar melting temperatures with their complementary target sequence. That is, the oligonucleotide probes are selected so that the melting temperature of each different type of oligonucleotide probe and its complementary sequence are within about 2° C. or within about 5° C. of one another. In some embodiments, an intentional mismatch for both the wild type and mutant sequences may be included in the probe to help achieve a desired melting temperature. In some embodiments, other modifications such as the use of locked nucleic acid (LNA) bases or bridge nucleic acid (BNA) bases may be used to help achieve a desired melting temperature.

In some embodiments the buffer used to conduct scodaphoresis is selected to have a salt content and electrical conductivity compatible with a subsequent PCR process. For example, the output buffer may have a composition of 89 mM TRIS; 89 mM borate; and 100 mM KCl. Such a buffer may have an electrical conductivity for example of 13 mS/cm. In some embodiments, the volume of sample removed from scodaphoresis block 60 corresponds to a volume of sample required to carry out amplification step 62.

In some embodiments, further modification of target DNA purified at scodaphoresis block 60 is conducted. In some embodiments, target DNA strands are extended and/or adaptors or indices are attached to the target DNA strands as may be desired to facilitate further processing of the sample. In some embodiments, adaptors or indices are attached to the target DNA strands by using Y-adaptors, molecular inversion probes (MIP), ligation, or other enzymatic or chemical methods.

In some embodiments, scodaphoresis block 60 is configured to selectively concentrate DNA molecules having mutant sequences while rejecting DNA molecules having wild type sequences. In some such embodiments, after scodaphoresis at block 60, a known amount of DNA molecules having the wild-type sequence(s) is added to the sample as a positive control that aids quantitation of mutation in the final assay. For example, an amount of DNA having the wild-type sequence equal to 0.01% of the original amount of DNA present in the sample may be added such that a mutation comprising 0.01% of the original DNA would appear to be at the same signal amplitude as the wild-type positive control at detection stage 66.

In block 62 a further DNA amplification is performed. Block 62 may comprise another PCR process that amplifies DNA that has been concentrated and recovered from scodaphoresis in block 60. The same or different primers may be used for the PCR reaction in block 62 as were used in the initial PCR of block 56. PCR in block 62 may be carried on for more cycles than the PCR of block 56. For example, in some embodiments, the PCR in block 62 is carried out for 35 to 50 cycles, or any number there between. In an example embodiment, PCR in block 62 is carried out for 45 cycles.

In some embodiments, the buffer used to conduct DNA amplification at block 62 is selected so that when the end product of conducting scodaphoresis in block 60 is added to the buffer in which the DNA amplification reaction will be conducted, the salts remaining in the buffer used to conduct scodaphoresis step 60 are diluted to yield a final salt concentration that is amenable to amplification at block 62. In some embodiments in which amplification stages at blocks 56 and 62 are both PCR, the primers used to conduct PCR are the same in both of blocks 56 and 62. In some embodiments, the primers used to conduct PCR in block 62 are different from the primers used to conduct amplification at block 56.

In block 64, the resulting DNA is optionally processed to remove primer and/or enzymes left over from the PCR stages, for example by addition of appropriate enzymes.

In block 66 mutant DNA is detected and/or measured. Mutations may be detected and/or measured by any of DNA sequencing (e.g. Sanger sequencing or next generation sequencing, single molecule sequencing, including nanopore-based sequencing, sequencing by synthesis approaches, pyrosequencing, or sequencing by hydrogen ion release detection), quantitative PCR, mass spectrometry and/or combinations thereof or any other suitable method to detect mutated DNA sequences and/or SNPs. In some embodiments, single base extension, ion semiconductor sequencing, or personal sequencing techniques, such as SNaPshot™, IonTorrent™, or MiSeq™ techniques are used at detection stage 66.

A signal representing the relative amount of a particular mutation or SNP detected may be compared to a control signal or to a signal representing some other component such as GAPDH. GAPDH is a so-called housekeeping gene. The abundance of GAPDH in the DNA output from the process represents a measure of the total amount of DNA input to the process. Therefore, comparison of the absolute abundance of different mutations to GAPDH permits estimation of the concentration of the mutation in the original sample. In some embodiments, the medium used to conduct scodaphoresis stage 60 includes probes specific for GAPDH, so that DNA that includes the GAPDH sequence will be passed from scodaphoresis stage 60 to detection stage 66. In such embodiments, primers specific for amplification of GAPDH can be included in amplification step 56 so that GAPDH DNA is amplified prior to scodaphoresis stage 60.

Block 68 stores, prints, displays, transmits or otherwise outputs information representing the results detected in block 66. In some embodiments, block 68 calculates the percentage content of a specific mutation or SNP relative to the total amount of DNA for a specific gene (i.e. mutant/SNP and wild type sequences). In some embodiments, block 68 calculates the percentage content of a specific mutation or SNP based on the amount of the mutation detected at block 66, the amounts and ratios of positive controls, and the abundance of mutant/SNP and wild type DNA measured at block 70.

In any of the descriptions herein, as an alternative to amplification by PCR, linear amplification may be performed (although linear amplification can be less efficient than PCR and is therefore not preferred in some embodiments). Amplification could also or alternatively be carried out by rolling circle amplification (RCA) or multiple displacement amplification (MDA).

While in the above exemplary embodiment, the amplification performed at block 62 has been described as being conducted prior to detection in block 66, in some embodiments, the measurement and/or detection method could include an amplification step, and therefore a separate amplification step may not be required.

Some embodiments include a step for removing probes and/or markers that may be used in scodaphoresis block 60 from the sample. In some embodiments, this step is facilitated by using probes and/or markers in which a base has been replaced with an analog that can be selectively degraded. For example, the probes may be made in such a manner that the base thymine (T) is replaced with uracil (U). Where this is done, in a cleaning step, the probes and/or markers containing uracil can be selectively degraded. Selective degradation may be triggered by application of a suitable enzyme. In some embodiments, exonuclease I (ExoI) is added to digest any remaining single stranded DNA (e.g. primers). In some embodiments, a phosphatase such as shrimp alkaline phosphatase (SAP) is added to dephosphorylate dNTPs.

In some embodiments there are two sequentially performed scodaphoresis steps. The two sequentially performed scodaphoresis steps may be performed using separate probes. In this manner it may be possible to select only DNA in which two separate mutations are present in combination—a mutation concentrated by the first scodaphoresis stage and a second mutation concentrated by the second scodaphoresis stage.

In one exemplary embodiment, detection in block 66 includes conducting SNaPshot™ PCR to amplify selected mutations and/or SNPs and then conducting Sanger extension and Sanger sequencing. In such embodiments, measurement and/or detection at block 68 can include reading the absolute amplitude of mutant/SNP peaks versus control signals. The absolute quantitative level of a particular mutant/SNP can also be compared to the absolute quantitative level of a housekeeping gene such as GAPDH. The abundance of a particular mutant/SNP relative to a corresponding wild-type sequence can be determined.

Figure 6:
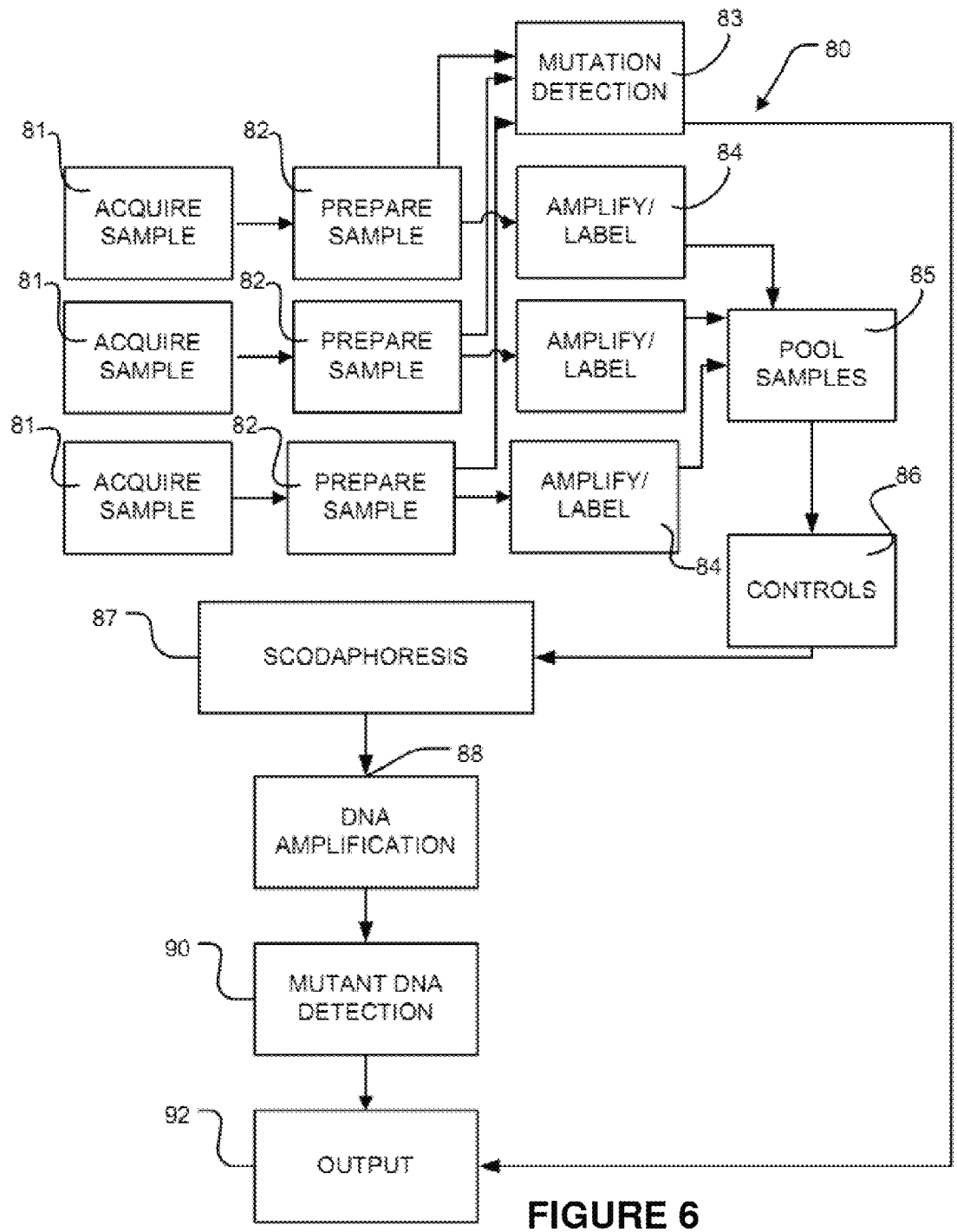
FIG. 6 shows a method for detecting DNA mutations in biological samples from a plurality of different subjects according to one embodiment of the invention.

The methods and apparatus described herein can be expanded for multiplex analysis of a plurality of nucleic acids. With reference to FIG. 6, an embodiment of a method 80 in which samples from a plurality of different subjects are pooled for analysis is described. Method 80 is generally similar to method 50 and any of the steps described with respect to method 50 can be used in method 80, but method 80 includes features to uniquely identify nucleic acids obtained from each individual subject after the samples have been pooled. Samples are acquired from a plurality of subjects at block 81 in any suitable manner, for example as described with reference to block 51.

Sample preparation is optionally conducted at block 82 in any suitable manner, for example as described with reference to block 52. At block 83, an aliquot is removed from each sample for further analysis. In some embodiments, the further analysis performed at block 83 includes using real time PCR to measure the number of genome copies present in extracted DNA in each sample, for example by measuring the amount of one or more housekeeping genes such as GAPDH in each sample. In some embodiments, the further analysis performed at block 83 includes an initial mutation detection step using any suitable detection technique for each sample, for example those detection methods described above with reference to block 66. Data collected at block 83 feeds into block 88, where all data is considered to provide a quantitative measure of one or more mutations in the sample.

At block 84, an amplification step is conducted and further nucleic acid modifications, such as ligation or extension, are optionally carried out. At block 84, nucleic acids in the samples obtained from each different subject are uniquely labelled, so that DNA originating from each subject can be identified after the samples have been pooled for further analysis. In some embodiments, unique labelling of nucleic acids in each sample is achieved by conducting PCR using primers that include one or more unique sequences that can be used to identify DNA from each sample in downstream processing. In some embodiments, barcoded sequencing adaptors are coupled to target nucleic acid molecules through ligation either prior to or after amplification. In some embodiments, adaptors or indices are attached to the target nucleic acid molecules using Y-adaptors, molecular inversion probes (MIP), ligation, or other enzymatic or chemical methods. In some embodiments, amplification is carried out for a limited number of cycles using any of the methods and performing any of the modifications described above with reference to amplification at block 56.

Figure 7:
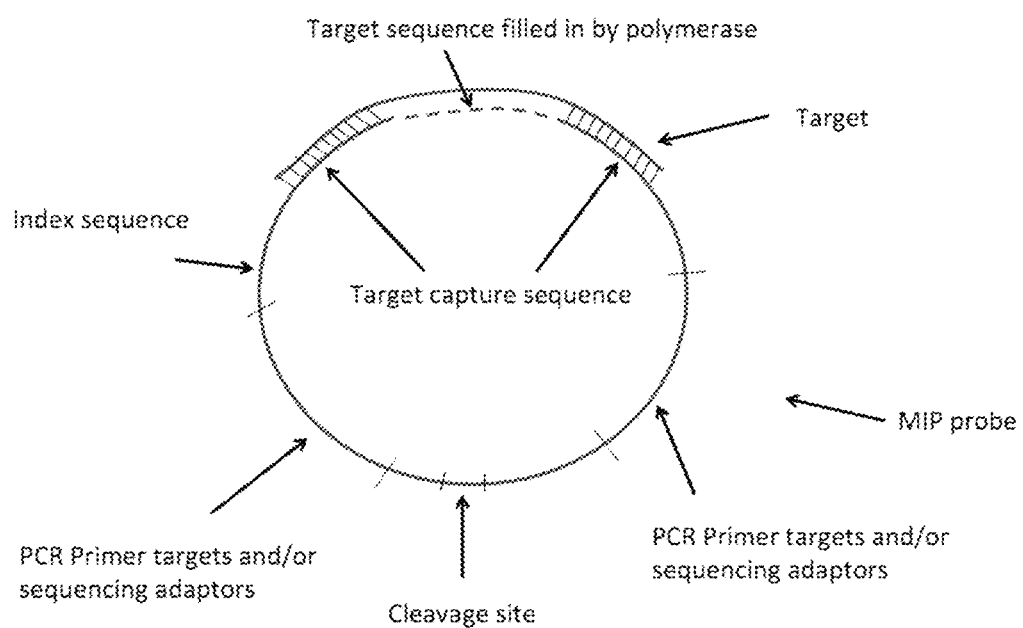
FIG. 7 is a schematic diagram showing an example molecular inversion probe (MIP) that can be used for conversion of short DNA fragments to longer DNA fragments for use with certain embodiments of the invention.

In one exemplary embodiment, amplification at block 84 includes the steps of conducting PCR using molecular inversion probes (MIP) designed to include binding sites for standard primers, together with a unique sequence that acts as an index for each sample. A simplified schematic diagram of an exemplary molecular inversion probe bound to a short DNA target is illustrated in FIG. 7. The probe contains sequences that hybridize to the target (target capture sequences), as well as any additional sequences desired (PCR primers, indices, adaptors etc.). The MIP probe also contains a cleavage site that is targeted by a restriction enzyme. Once the MIP probe is hybridized to the target, the remaining target complementary sequence is filled in through enzymatic extension and the MIP probe ultimately becomes circular by means of ligation. It is then cleaved at the cleavage site, forming a linear strand of DNA that can be replicated by PCR. In this manner, the target sequence is replicated in a DNA strand which also contains PCR primers and potentially sample indexing sequences.

Where multiple different mutations are to be measured in the same sample, MIPs specific for each such mutation are used, but all MIPs used on a particular sample can optionally include the same index and can optionally include the same binding sites for the standard primers. The MIP PCR product is optionally cleaned, and is then subjected to further amplification using the standard primers. The PCR product is then optionally cleaned. PCR clean up may be performed for example using any of the methods described with reference to block 58 above, including optionally separating strands of DNA to provide single-stranded DNA for the subsequent scodaphoresis step.

At block 85, the samples are pooled for further analysis. While in this exemplary embodiment amplification takes place before samples are pooled, in some embodiments amplification takes place after samples are pooled. For example, in embodiments in which unique identifiers are coupled to nucleic acids from each sample by ligation, the samples could be pooled prior to amplification. In alternative embodiments, samples can be pooled after scodaphoresis in block 87.

At block 86, controls are optionally added. In some embodiments, positive controls are introduced at a known mutant abundance of 0.1%. In some embodiments, at least some of the controls added include a label to facilitate optical monitoring of the progress of scodaphoresis, for example a fluorescent label.

At block 87, scodaphoresis is conducted, with probes specific to each one of the mutations to be detected (or specific to the wild type sequence corresponding to each one of the mutations to be detected) immobilized in the separation medium in any suitable manner, for example as described above.

At block 88, a second stage of DNA amplification is conducted in any suitable manner, for example as described with reference to block 62 above. In some embodiments, the second stage of DNA amplification comprises PCR using standard primer sequences added to the DNA molecules in block 84. As described with reference to method 50, any suitable techniques can be used to avoid contamination or interference between the steps of method 80, including for example synthesizing the probes for scodaphoresis to contain uracil (U) in place of thymine (T) to facilitate selective digestion of any probes that may pass through to the output of scodaphoresis block 87 and/or appropriate PCR clean up steps. Steps may be taken (e.g. dilution, buffer exchange or the like) to ensure that the output from one stage is compatible with the output of a subsequent stage.

At block 90, mutant DNA is measured and/or detected by any suitable means, including for example those methods described with reference to block 66 above. Sequence data including the sequences of the unique identifiers associated with each data are obtained to read both the mutation and the indices to deconvolute strands. Output from blocks 90 and 83 is passed to block 92 where an assessment of the relative abundance of one or more mutations in the samples obtained from each subject is evaluated. In some embodiments, block 92 calculates the percentage content of a specific mutation in the sample from each subject based on the amount of the mutation detected for that sample as detected at block 90 with reference to the unique identifier for each subject's sample, the amounts and ratios of positive controls, and the amount of mutant and wild type DNA measured for that sample at block 83.

In one exemplary embodiment, the samples used in method 80 are plasma obtained from a plurality of subjects, the plasma is subjected to purification using a circulating free DNA purification kit, e.g. a Qiagen™ cfDNA kit, amplification is conducted using molecular inversion probe (MIP) PCR using a probe containing standard primer sequences and an index followed by 4 cycles of PCR using the standard primers, positive controls are introduced at 0.1% mutant abundance, up to 96 samples are then pooled together with four controls and subjected to scodaphoresis, amplification, and sequencing using a MiSeq™ sequencer.

Thus, the invention enables characterization of rare nucleic acids that are biomarkers for disease or the progression of a disease. Further embodiments are disclosed in the below examples and claims.

Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms. Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

While blocks in example processes are presented in a given order, alternative examples may have steps, or employ systems having blocks, in a different order. While exemplary embodiments have been described as including specific steps, alternative embodiments may have steps drawn from other exemplary embodiments, and/or in a different order. Such processes may be modified by moving, deleting, adding, subdividing, combining, and/or modifying blocks and/or steps to provide alternative processes or subcombinations. Each of these processes or blocks may be implemented in a variety of different ways. Also, while processes or blocks or steps are at times shown as being performed in series, these processes or blocks may instead be performed in parallel, or may be performed at different times. In addition, while elements are at times shown as being performed sequentially, they may instead be performed simultaneously or in different sequences.

Where a component (e.g. a medium, power supply, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the claims hereafter introduced are interpreted to include all such modifications, permutations, additions, omissions and sub-combinations as may reasonably be inferred. The scope of the claims should not be limited to the example embodiments described above, but should be given the broadest interpretation consistent with the description as a whole. It will be apparent to those skilled in the art that embodiments of the invention include a number of aspects, including the following:

EXAMPLES

Embodiments of the invention are further described with reference to the following examples, which are intended to be illustrative and not limiting in nature.

Example 1.0

Allele Enrichment: BRAF V600E Vs. BRAF Wild-Type Alleles

In one example, DNA having the sequence BRAF V600E was separated from BRAF wild-type DNA using a 3-arm scodaphoresis apparatus similar to that illustrated in FIGS. 3A-F and the accompanying text.

In this example, the target sequence was DNA coding for the BRAF V600E mutation, modified to include unique primer sequences at both the 5' and 3' ends. The target had the following sequence, wherein the point mutation 1799T>A is indicated in bold and the PCR primers are underlined:

SEQ ID NO. 21:
5' - <u>ACT GCG GTC CTG AGC GAG</u> TGA TTT TGG TCT AGC

TAC AGA GAA ATC TCG ATG GAG TGG GTC CCA TCA

<u>GGC CAA CCT CCA CCG TCG</u> - 3'

The wild type DNA coding for BRAF wild type, modified to include unique primer sequences at both the 5' and 3' ends, had the following sequence, wherein the location of T 1799 is indicated in bold and the PCR primers are underlined:

SEQ ID NO. 22:
5' - <u>GCC AAC CTC CAC CGT CGG</u> TGA TTT TGG TCT AGC

TAC AGT GAA ATC TCG ATG GAG TGG GTC CCA TCA

<u>GAC TGC GGT CCT GAG CGA</u> - 3'

The medium used to conduct scodaphoresis included a probe having the following sequence: SEQ ID NO. 23: 5'-CAT CGA GAT TT+C+T+CT GTA GC-3', wherein a "+" precedes a locked nucleic acid base and the base complementary to the point mutation T 1799 A is indicated in bold.

Scodaphoresis was conducted in 1× tris-borate (TB) running buffer including 100 mM KCl. The medium was a 4% polyacrylamide gel, with immobilized probes therein at a concentration of 10 μM. $3 \times 10^7$ copies of the mutant sequence were inputted and $1.4 \times 10^9$ copies of the wild type sequence were inputted into scodaphoresis.

The operating conditions were selected so that DNA molecules having the mutant BRAF V600E sequence migrated toward a central extraction well of the apparatus, while DNA molecules having the wild type BRAF sequence were washed out of a distal end of the separation arms of the apparatus. The sample was injected into the gel at a voltage of 50 V; SCODA focusing with a washing bias was conducted using a rotating electric field at 400 V with a SCODA cycle of 2 seconds application to Arm A, 2.75 seconds application to Arm B, and 2.75 seconds application to Arm C for 8 minutes. A final focusing step of 400 V applied for 2 seconds on each arm was applied for 2 minutes to collect target DNA in the central extraction well.

Scodaphoresis produced 25 μL, of output volume. 2 μL, of this output volume was analyzed with qPCR for the presence of both mutant and wild type DNA sequences, using the unique primer sequences for both mutant and wild type sequences. 62% of the mutant copies were recovered from the central extraction well, whereas only 0.00003% of the wild type copies were recovered from the central extraction well. This represents an enrichment ratio of the mutant to the wild type sequence of approximately 2,200,000, i.e. a greater than 1,000,000-fold reduction in the level of wild-type sequence present in the initial sample.

Example 2.0

Improvement of qPCR Assay Sensitivity

A TrimGen™ qPCR assay was challenged with a mixture of DNA from a cell line containing a BRAF V600E mutant and wild type human genomic DNA (Roche) from 0% to 7% abundance.

PCR was conducted on the sample at the BRAF locus for 15 cycles using forward primer SEQ ID. NO. 24: 5'-CTACT-GTTTTCCTTTACTTACTACACC-3' and reverse primer SEQ ID NO. 25: 5'-CTCAATTCTTACCATCCA-CAAAATG-3'. DNA was sheared for 25 minutes, and scodaphoresis was performed using the conditions outlined above, including the probe present in the gel. PCR cleanup was performed to remove excess probe, and then TrimGen™ eQ-PCR was performed using TrimGen™ primers.

Figure 8A:
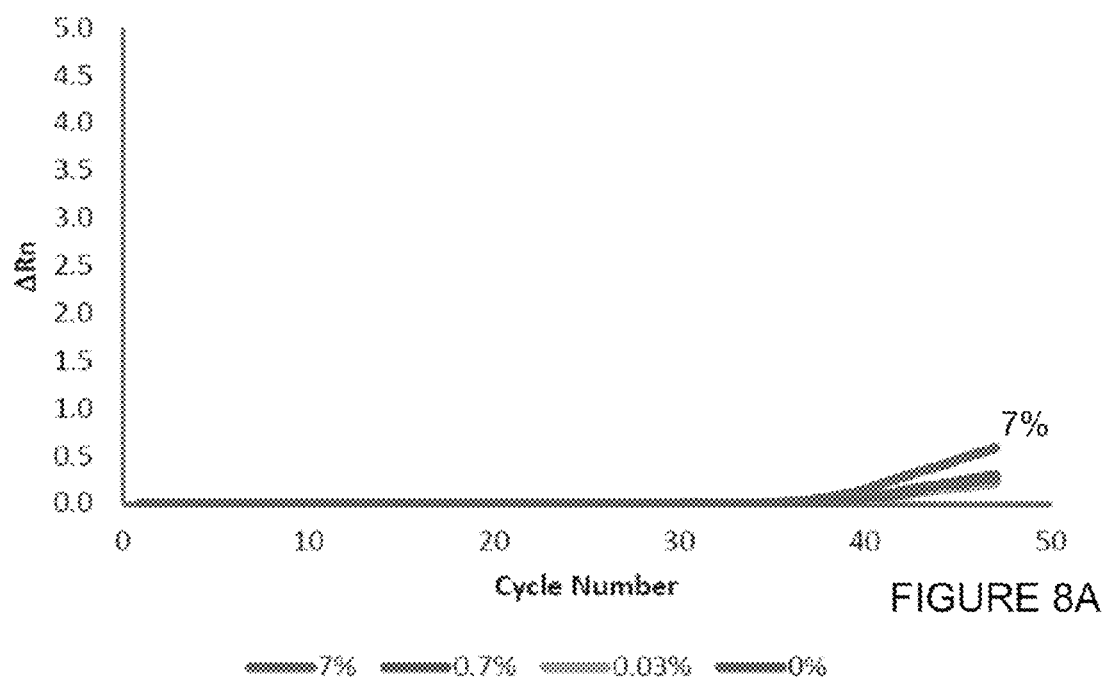
FIG. 8A shows the results of a qPCR assay for the presence of BRAF V600E mutant in a mixed sample containing BRAF V600E and BRAF wild-type cell lines conducted according to state-of-the art protocols.
Figure 8B:
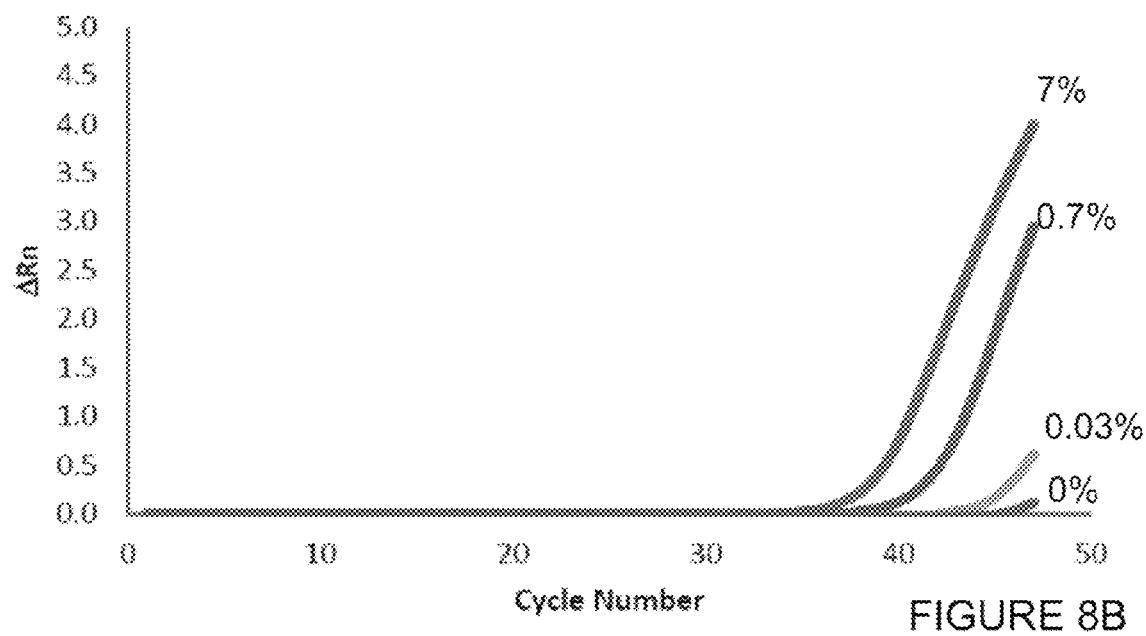
FIG. 8B shows the results of a qPCR assay for the presence of BRAF V600E mutant in a mixed sample containing BRAF V600E and BRAF wild-type cell lines after processing of the sample according to one embodiment of the invention.

As shown in FIGS. 8A and 8B, the limit of detection of qPCR alone as conducted in this example is approximately 7% abundance of BRAF V600E mutant cell line, as indicated by the overlapping results for samples having 0%, 0.03% or 0.7% BRAF V600E mutant cell line abundance (FIG. 8A), in which ΔRn is the normalized fluorescence of the reporter dye for detection of DNA having the BRAF V600E sequence. In FIG. 8A, the blue line representing the results for 7% abundance of the BRAF V600E mutant cell line shows a detectable signal after approximately 35 cycles of PCR, while the red, orange and purple lines representing 0.7%, 0.03% and 0% abundance of the BRAF V600E mutant cell line essentially overlap.

After enrichment of DNA having the BRAF V600E sequence, performing qPCR results in a distinct signal above baseline (i.e. the signal for the 0% abundance sample) for each of the 7% (blue line farthest to the left), 0.7% (red line second from left) and 0.03% (green line third from left) samples as compared with the 0% (purple line farthest to the right) abundance of BRAF V600E sample (FIG. 8B). Additionally, the point at which the 0% abundance baseline sample yields a detectable signal is increased to approximately 45 cycles of PCR.

Example 3.0

Enrichment of Mutant DNA from Formalin-Fixed Tissue Samples Improves SNaPshot Limit of Detection A SNaPshot™ assay was used to detect the presence of DNA having the BRAF wild-type sequence (red curve, visible in FIG. 9A) and the BRAF V600E mutant sequence (green curve, visible in FIG. 9B) in a formalin-fixed, paraffin-embedded (FFPE) tissue sample having 5% mutant content. A Qiagen™ FFPE kit was used to extract DNA from the FFPE tissues, and the FFPE DNA was mixed to 5% mutant content. A 163 base pair amplicon of the BRAF locus was amplified by PCR for 7 cycles using the same primers as for Example 2 and DNA was sheared by sonication.

Scodaphoresis was carried out under the same conditions as described for Example 1, except that the probes immobilized in the gel included uracil (U) in place of the thymine (T) bases. The same 163 base pair amplicon of the BRAF locus was amplified by PCR for 45 cycles, and then PCR cleanup was conducted by adding Exonuclease I and alkaline phosphatase to the sample to degrade remaining PCR primers and inactivate the dNTPs.

A BRAF SNaPshot assay was performed using a 46 base SBE primer SEQ ID NO. 26: 5'-GACTGACTGACTGACT-GACTGACTGTGATTTTGGTCTAGCTACAG-3' for 25 cycles using fluoro dideoxy nucleoside triphosphates (ddNTPs). Underlined bases represent the primer sequence. The remainder of the primer sequence is a tag. Alkaline phosphatase was added to the reaction mixture to inactivate remaining dNTPs, and then mutation analysis was conducted by sequencing the DNA.

Figure 9A:
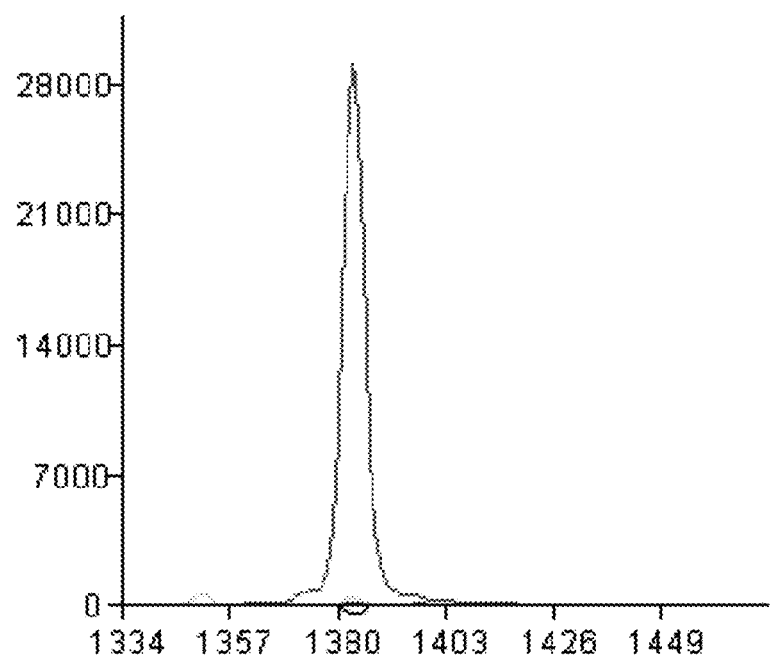
FIG. 9A shows the results of a SNaPshot™ assay for BRAF V600E mutant DNA from formalin-fixed paraffin-embedded (FFPE) tissue containing 5% mutant BRAF V600E in a background of wild-type BRAF according to state-of-the art protocols.
Figure 9B:
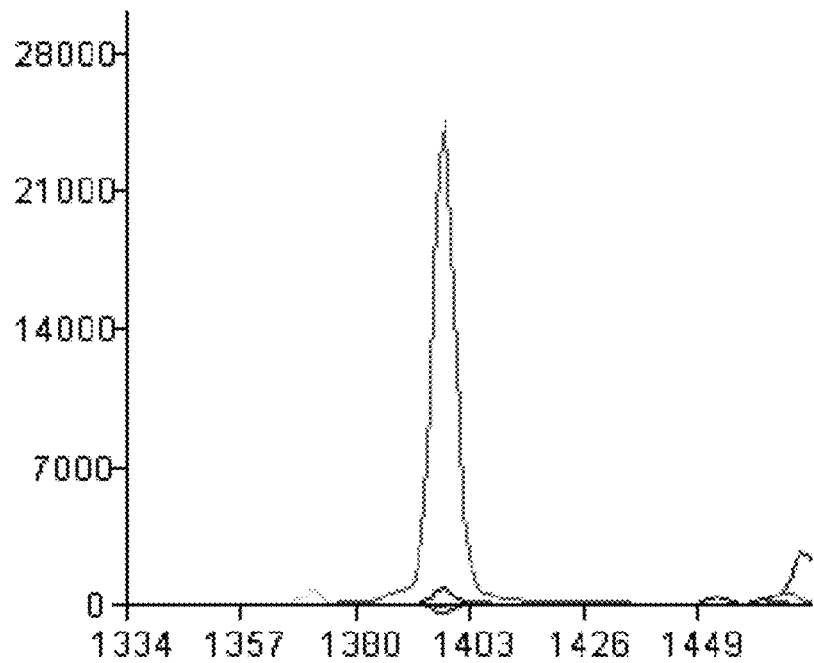
FIG. 9B shows the results of a SNaPshot™ assay for BRAF V600E mutant DNA from formalin-fixed paraffin-embedded (FFPE) tissue containing 5% mutant BRAF V600E in a background of wild-type BRAF according to one embodiment of the invention.

As shown in FIG. 9A, a SNaPshot™ carried out according to standard protocols is not able to detect the presence of a 5% abundance BRAF V600E mutation in the FFPE sample (the large curve in FIG. 9A is red, indicating the results of amplification of DNA having the BRAF wild-type sequence in the SNaPshot™ PCR). As shown in FIG. 9B, after performing scodaphoresis to enrich for DNA having the BRAF V600E mutation, the SNaPshot™ is able to detect the presence of the 5% abundance BRAF V600E mutation in the FFPE sample (the large curve in FIG. 9B is green, indicating the results of amplification of DNA having the BRAF V600E mutation in the SNaPshot™ PCR).

Example 4.0

Multiplex Enrichment with BRAF and EGFR Mutants

A plurality of synthetic DNA representing both mutant (green label) and wild type (red label) sequences for five different biologically relevant mutations was separated in a multiplexed separation using scodaphoresis under the conditions described for Example 1. Synthetic target DNA molecules 100 nucleotides in length having mutant sequences complementary to the probes identified below were prepared by placing the sequence in the center of a DNA molecule filled out on either side of the sequence with T's. Corresponding wild type target DNA molecules 100 nucleotides in length were prepared in a similar manner, but using the wild type sequence instead of the mutant sequence. The melting temperature of each of the perfect match mutant sequences for its corresponding probe was designed to be approximately 68° C.

A plurality of unique probes having the following sequences were immobilized in the gel used to conduct scodaphoresis (wherein "+" preceding a base indicates a locked nucleic acid base). Bases in bold indicate the position of the mutation in the DNA sequence for point mutations. Deletions occur between the underlined bases in deletion mutations. For deletion mutations, the wild type sequence is the complete DNA sequence, without the deletion:

```
BRAF V600E (T1799A): SEQ ID NO. 27:
5'-CAT CGA GAT TT+C +T+CT GTA GC -3'

EGFR T790M (2369C > T) - SEQ ID NO. 28:
5'-GGC AUG AGC UGC +AUG AUG A -3'

EGFR E746_A750del15 c.2235-2249 - SEQ ID NO. 29:
5'-CTT TCG GAG ATG TTT TGA TAG CGA CG-3'

EGFR E746_A750del15 c.2236-2250 - SEQ ID NO. 30:
5'-TTT CGG AGA CTT GAT AGC GAC G-3'

EGFR L858R - SEQ ID NO. 31:
5'-GCC CGC CCA AAA TCT -3'
```

Mutant and wild type target DNA for each of the above mutations were injected into a scodaphoresis apparatus in a known series to provide spatial separation across the width of one separation arm (FIG. 10A). With reference to FIG. 10A, the loaded samples are, from left to right, BRAF V600E, EGFR T790M, EGFR E746_A750del15 c.2235-2249, EGFR E746_A750del15 c.2236-2250, and EGFR L858R.

Mutant and wild type DNA molecules are then separated from one another at the same time through the application of SCODA fields with a washing bias, as described with reference to Example 1. As shown in FIGS. 10B-10E, DNA molecules having the mutant sequences (green label) simultaneously all migrate towards the central extraction well of the scodaphoresis apparatus, while DNA molecules having the wild type sequences (red label) are washed out of the distal end of the separation arm.

Example 5.0

Example Workflow Protocols

Figure 12A:
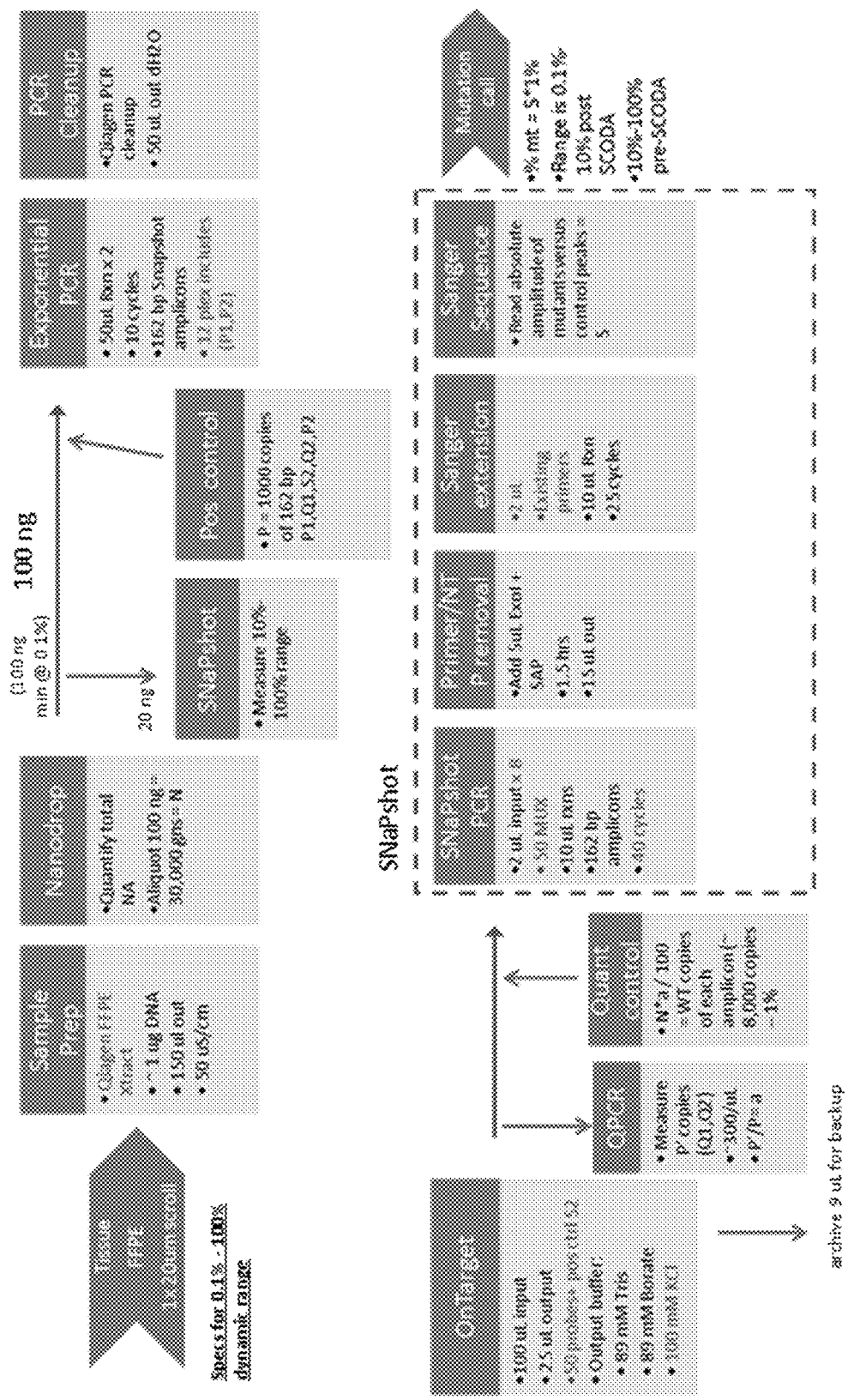
FIGS. 12A-12C show example workflows according to exemplary embodiments for mutation detection according to embodiments using various different samples and/or detection methods.

FIG. 12A illustrates a prospective example workflow protocol for detecting mutations in formalin-fixed paraffin-embedded tissue samples with an abundance ranging from 0.1% to 100% in tissue using a SNaPshot™ assay for detection. Briefly, DNA is extracted from tissue using conventional methods such as a Qiagen™ kit. Extracted DNA is quantified with a Nanodrop™ spectrophotometer to estimate the total amount of DNA present in the sample. From this sample, 100 ng (equal to ~30,000 genomes) is carried to the rest of the workflow. An additional 20 ng of DNA is processed through a SNapShot™ assay to determine whether high abundance (10%-100% abundance) mutations are present. The 100 ng sent for further analysis is spiked with a positive control that contains regions complementary to PCR primers in the subsequent PCR reaction (P1, P2), as well as a sequence complementary to a probe immobilized in the medium used to conduct scodaphoresis (S2), and additional target sequences complementary to the primers used in subsequent qPCR reaction (Q1, Q2). Exponential PCR is performed on the sample to amplify the gene loci of interest, and, if required, subsequent dilution is used to decrease the amount of total DNA present in the sample. A PCR reaction clean-up may be carried out at this point to reduce the salinity of the sample and to remove unwanted components from the PCR reaction (including enzyme and primers). Amplified DNA is now subjected to scodaphoresis, in a gel system that incorporates up to 50 or more immobilized probes for concentration of specific mutations. The output of the scodaphoresis concentration is tested with qPCR to determine how much of the positive control is present, and therefore the yield of the process to this point. Copies of wild-type DNA for each locus being tested are now spiked into the sample to provide a comparison for SNaPshot™, in order to allow quantitation of the mutation. SNaPshot™ is carried out with 50-fold multiplexing, and the ratio of the detected mutation amount compared to the spiked wild-type DNA amount is used to calculate the original percent mutation in the sample. Existing primers (i.e. probes already used in the SNaPshot™ process) can be used to conduct the Sanger extension.

Figure 12B:
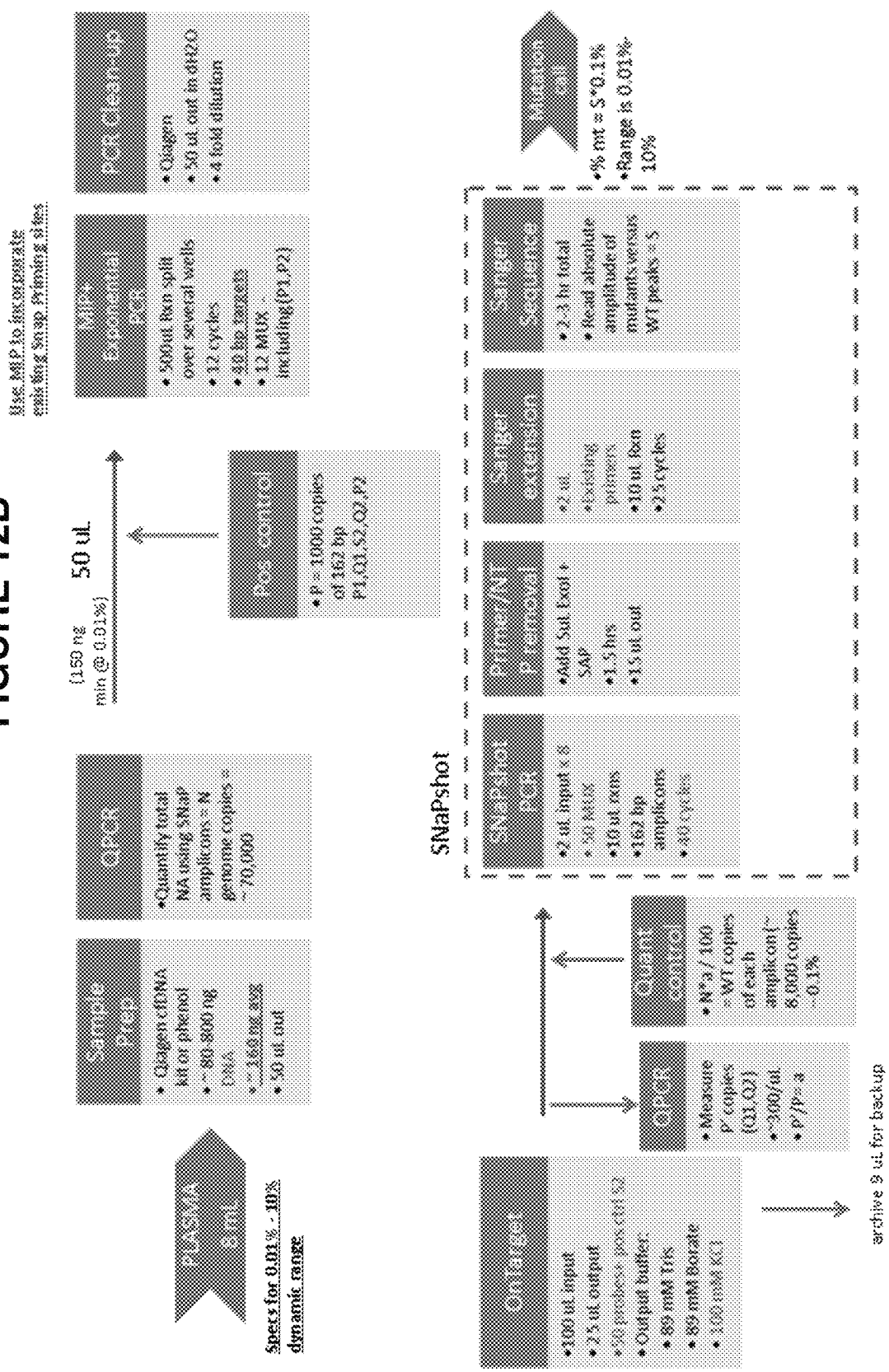

FIG. 12B illustrates a similar prospective exemplary workflow for use with plasma as the sample, where mutation abundance is expected to be lower than in formalin-fixed paraffin-embedded tissue. Here the working range of mutation abundance detected by the process is 0.01% to 10%. Steps in this workflow are similar to the example described with reference to FIG. 12A except that SNaPshot™ is not used to test the sample prior to scodaphoresis enrichment. Instead, a different amount of wild-type DNA control is spiked into the enriched sample prior to SNaPshot™ detection, such that a range of 0.01% to 10% mutation content may be detected. Another difference in this workflow is that, due to the limited amount of DNA present in the sample, and due to its fragmented nature, molecular inversion probes (MIP) are used to convert short (40 bp) DNA fragments into longer fragments that are easily amplifiable with PCR. Alternatively, multiplexed PCR with closely spaced primer sequences may be used to amplify short (40 base pair) fragments. MIP conversion (e.g. using the probe shown schematically in FIG. 7), also attaches priming sites (P1, P2) to the converted DNA such that PCR and SNaPshot™ can proceed as they would with a regular DNA fragment of longer length originating directly from the sample. The PCR can also attach indices and priming sites to the amplified strand, as well as reconstruct missing parts of the original target gene sequence, such that PCR and SNaPshot™ can proceed as they would with a regular DNA fragment of longer length originating directly from the sample.

Figure 12C:
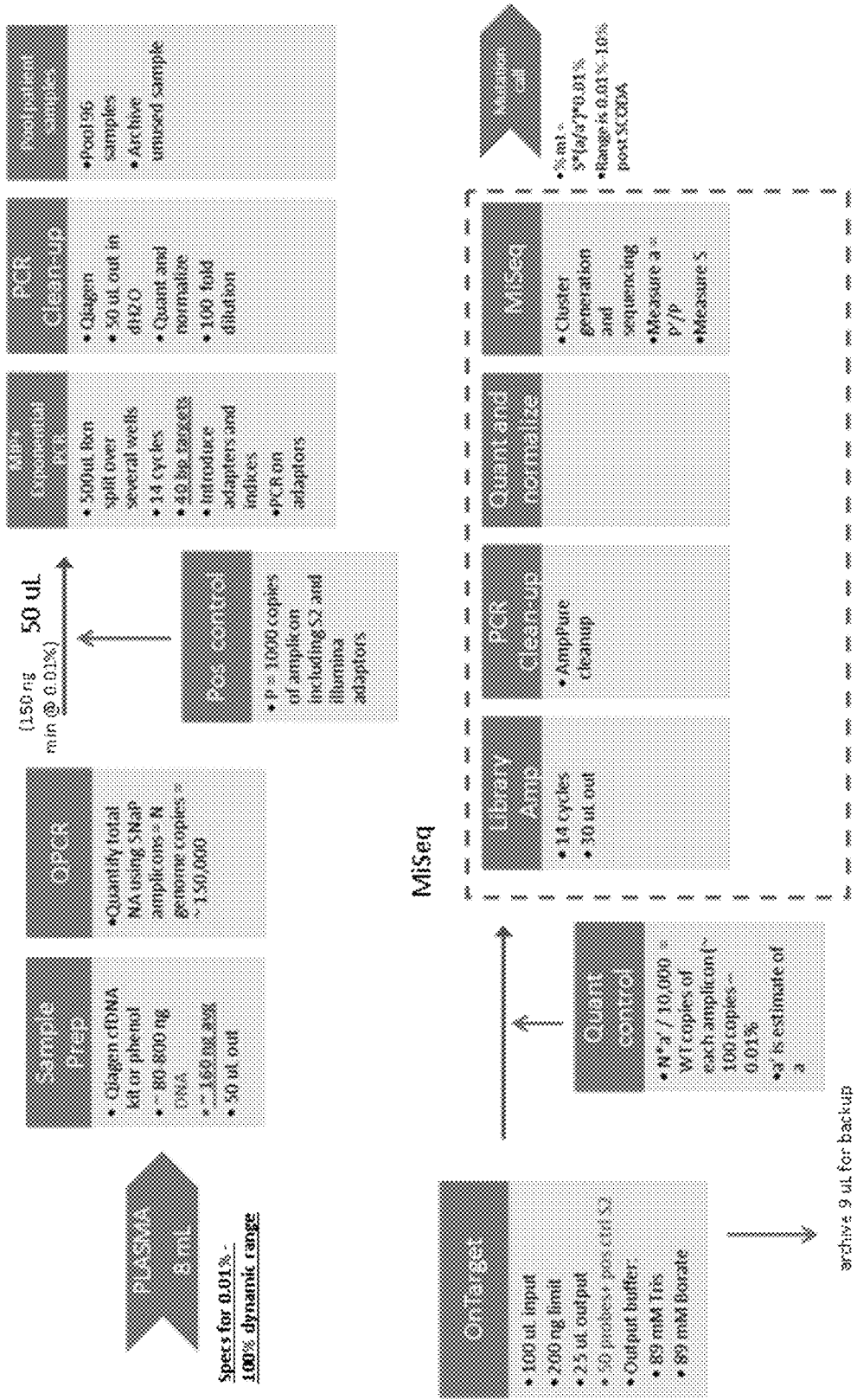

FIG. 12C illustrates a further exemplary prospective workflow using a DNA sequencer, in this example an Illumina MiSeq™ sequencer, although other sequencers could be used, combined with scodaphoresis to detect mutations in a plasma sample. In this case, the extended dynamic range of the sequencer allows detection of mutations ranging from 0.01% to 100% of the original sample. As in the example described with reference to FIG. 12B, MIP conversion is used to convert short DNA fragments to longer fragments, while at the same time introducing DNA indices that will identify each specific patient's DNA, and adapter sequences required by the DNA sequencing process. With indices attached to each DNA fragment, many patient samples may be pooled (96 in this example) and analyzed at the same time. As in exemplary workflows described above, a positive DNA control is added prior to MIP or PCR amplification, and in this case detected in the sequencing process to allow an estimation of process yield during data analysis. P' is measured by counting DNA sequences generated by the sequencing process. Positive wild-type controls are introduced prior to sequencing to provide a benchmark DNA quantity against which the mutation abundances can be compared.

Example 6.0

Comparison of MiSeq™ and MiSeq™ Plus OnTarget™ for Determining Low Level KRAS Mutations in Blood Plasma Human blood plasma was titrated with wild-type KRAS sequences containing no or 0.01% KRAS G12V mutant sequences. Each sample was divided in half, and amplified with eight cycles of PCR using appropriate primers. After amplification, one half of each sample was sequenced using MiSeq® (Illumina) alone. The other half was enriched for the KRAS G12V mutant using Scodaphoresis (OnTarget™ assay, Boreal Genomics) prior to sequencing with MiSeq®. Because only eight cycles of PCR were used prior to sequencing, there were few sequence errors resulting from the initial amplification.

Figure 13A:
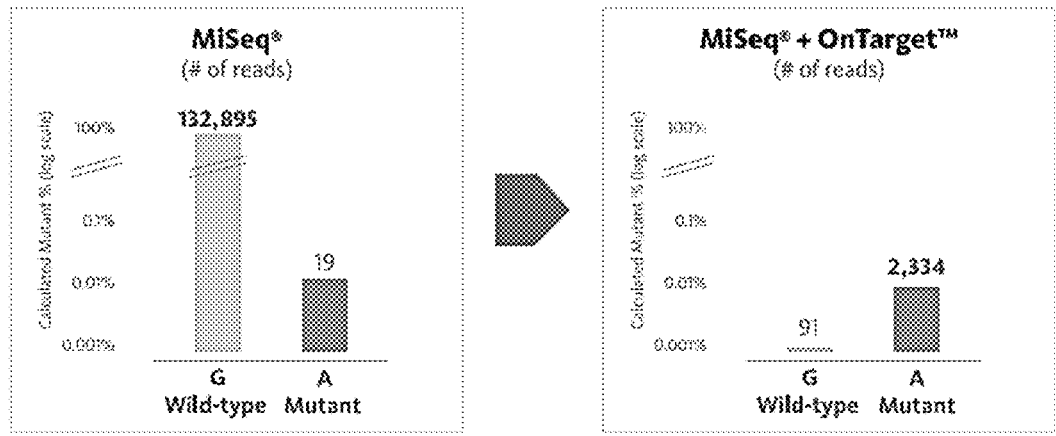
FIG. 13A illustrates that enrichment of targeted mutants (KRAS G12V) results in more efficient sequencing of the mutant strains. After enriching with Scodaphoresis, 100 times fewer total MiSeq™ reads are necessary to achieve 100 times more sequence reads of the mutant strain.

As shown in FIG. 13A, the sample spiked with 0.01% KRAS G12V yielded almost 133,000 reads of wild type KRAS compared to 19 reads of the mutant, when sequenced without further enrichment. Furthermore, as discussed below, it is difficult to know how many of the 19 reads are due to the KRAS G12V mutant versus wild type sequences that experienced some error during the sequencing process. In contrast, the portion of the spiked sample that was enriched with Scodaphoresis produced 2,300 KRAS G12V reads and only 19 wild-type reads, unequivocally confirming the presence of the mutant. It is also notable that scodaphoresis removed most of the wild-type from the sample, resulting in 1000-fold fewer reads. In practice, reducing unnecessary wild-type reads will reduce reagent consumption and allow higher throughput of mutant samples.

Figure 13B:
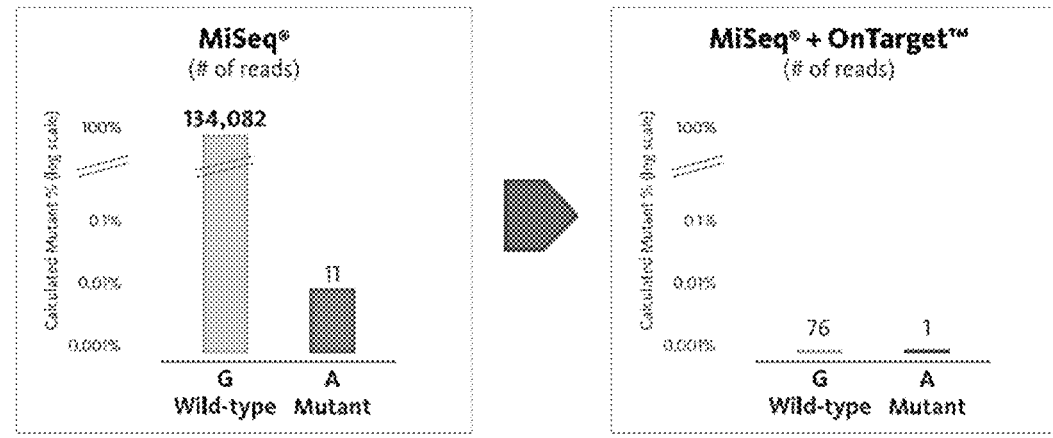
FIG. 13B illustrates that the enrichment protocol of FIG. 13A results in rejection of most of the wild type nucleic acids.

The effectiveness of scodaphoresis in removing wild-type background sequences can be seen in the right-hand panel of FIG. 13B, where a pure wild-type sample "enriched" with scodaphoresis results in about the same number of KRAS reads as the spiked sample. More telling, however is the left-hand panel of FIG. 13B, which shows a similar number of KRAS reads and mutant reads in a sample that was not spiked with 0.01% KRAS G12V. Based upon the comparison of the left-hand panels of FIGS. 13A and 13B, it would be impossible to make a "call" for the presence of KRAS G12V.

Nonetheless, as is seen by comparing the right-hand panels of FIGS. 13A and 13B, when the samples are enriched for a target sequence with Scodaphoresis, it is very evident which sample contained the mutant, and which sample did not. Thus, using Scodaphoresis enrichment prior to sequencing makes it is easier to quantify trace mutants while requiring substantially fewer reads to sequence those mutants. Overall, these improvements will allow greater reliance on biomarker screening while reducing the time and costs required for biomarker screening.

Example 7.0

Comparisons of Levels of Detection (LOD) Using MiSeq™ and MiSeq™ plus OnTarget™

As in Example 6.0, human blood plasma was titrated with wild-type and mutant KRAS sequences. In this Example, two types of wild-type DNA (varying at codons 12 and 13) were used in addition to three different concentrations of KRAS G12V (0.01%, 0.1%, and 1%), for a total of eight samples. As in Example 6.0, each sample was divided in half, and amplified with eight cycles of PCR. After amplification, one half of each sample was sequenced using MiSeq® alone, while the other half was enriched for the KRAS G12V mutant using Scodaphoresis prior to sequencing with MiSeq®.

Figure 14A:
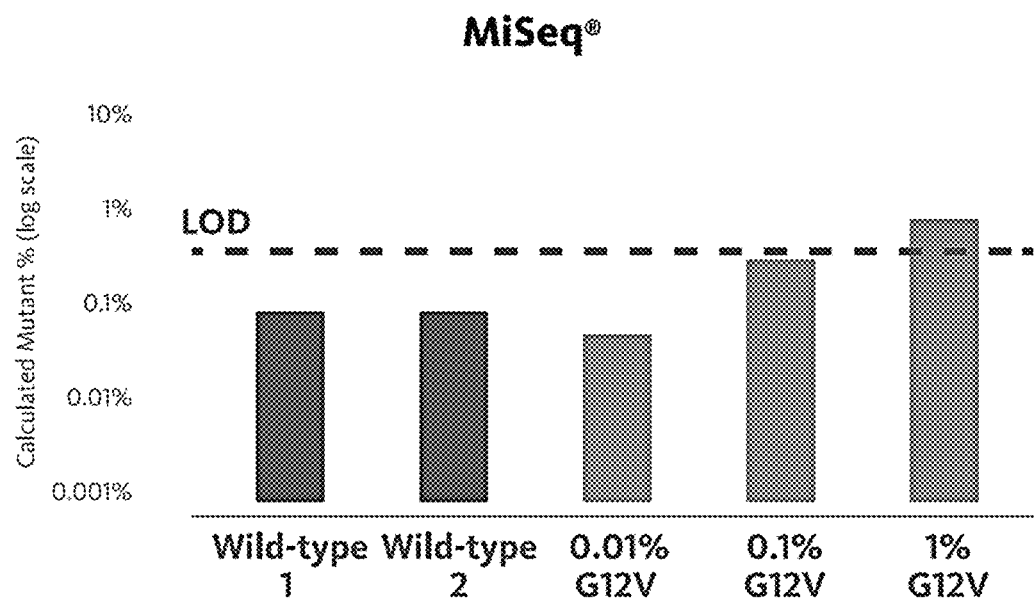
FIG. 14A shows the level of detection (LOD) for various concentrations of mutants using state-of-the-art characterization methods.
Figure 14B:
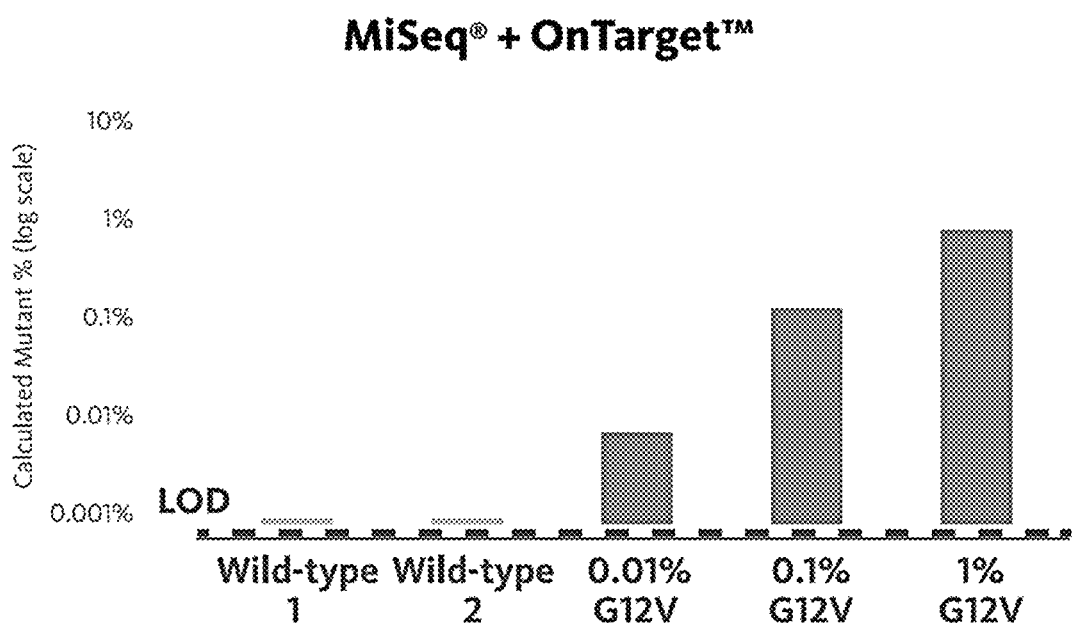
FIG. 14B shows that level of detection (LOD) for various concentrations of mutants using the methods of the invention. Using the methods of the invention, it is possible to identify/characterize a KRAS G12V mutant present at only 0.01% as compared to the wild-type nucleic acid.

As shown in FIG. 14A, using MiSeq, alone, both wild-type-only samples resulted in KRAS G12V sequence reads on the order of the samples comprising 0.1% KRAS G12V. Furthermore, calculating a Level of Detection (LOD), it is clear that the reads of the 0.01% and 0.1% mutant samples are not significant. In fact, only at 1% mutant do the reads have enough significance for the presence of the KRASG12V mutant to be "called." In contrast, as shown in FIG. 14B, all of the samples that were enriched for KRAS G12V with scodaphoresis are easily detectable at all of the tested concentrations, while the wild-type-only samples clearly do not contain any mutant.

Example 8.0

Figure 15A:
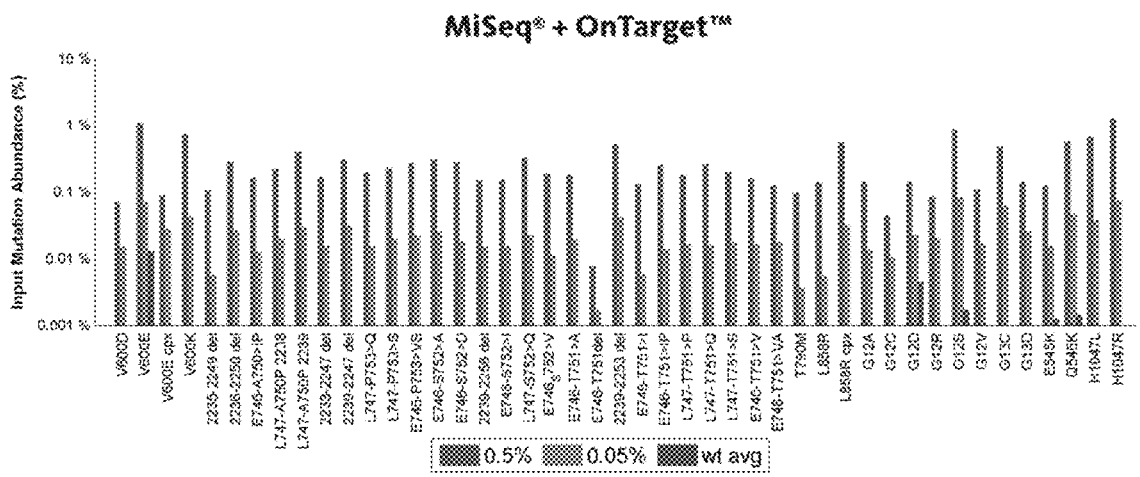
FIG. 15A shows the ability of the methods and apparatus of the invention to identify the presence of 45 different mutants in a single sample present at a concentration of 0.05% or lower.

Comparisons of Levels of Detection (LOD) Using MiSeq™ and MiSeq™ Plus OnTarget™ in a Sample Containing 45 Different Mutations To illustrate the feasibility of multiplexed analysis, blood plasma samples were spiked with 45 mutations in EGFR, KRAS, BRAF, and PIK3CA genes. One sample was spiked at 0.5% for each mutation, and another sample was spiked at 0.05% for each mutation. As shown in FIG. 15A, Scodaphoresis enrichment allowed detection of every mutation at a concentration of only 0.05% in the presence of EGFR, KRAS, BRAF, and PIK3CA wild-type sequences. For each sample, the Scodaphoresis enrichment was completed on a single OnTarget™ chip having a separation medium with probes for each of the 45 mutations. For comparison, the level of wild-type reads that after scodaphoresis are shown in red.

Figure 15B:
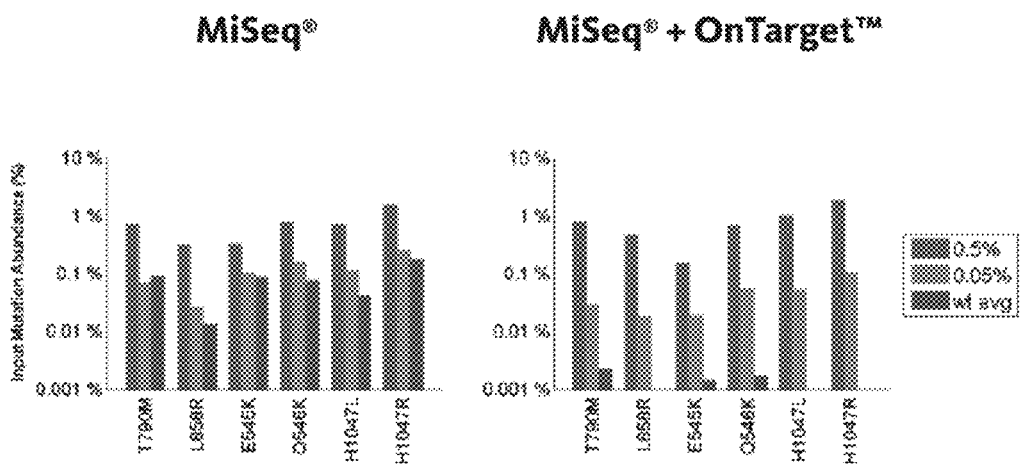
FIG. 15B compares the reporting of multiplexed wild-type and mutant nucleic acids using state-of-the-art characterization or the methods of the invention.

As shown in FIG. 15B, sequencing without enrichment was unable to identify most of the mutant sequences, even at even 0.5% concentration.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

TABLE 1

Exemplary Mutations for Cancer Analysis Panel.

| Gene | Accession Number | Mutation | Base Change | COSMIC ID |
| --- | --- | --- | --- | --- |
| BRAF | NM_004333 | V600E | 1799T>A | 476 |
| n = 7 | SEQ ID NO.: 1 | V600E (complex) | 1799_1800TG>AA (Complex) | 475 |
| | | V600D | 1799_1800TG>AT (Complex) | 477 |
| | | V600K | 1798_1799GT>AA (Complex) | 473 |
| | | V600A | 1799T>C | 18443 |
| | | V600G | 1799T>G | 6137 |
| | | V600M | 1798G>A | 1130 |
| KRAS | NM_004985 | G12A | GGT>GCT (35G>C) | 522 |
| n = 7 | SEQ ID NO.: 2 | G12D | GGT>GAT (35G>A) | 521 |
| | | G12R | GGT>CGT (34G>C) | 518 |
| | | G12C | GGT>TGT (34G>T) | 516 |
| | | G12S | GGT>AGT (34G>A) | 517 |
| | | G12V | GGT>GTT (35G>T ) | 520 |
| | | G13D | GGC>GAC (38G>A) | 532 |

TABLE 1-continued

Exemplary Mutations for Cancer Analysis Panel.

| Gene | Accession Number | Mutation | Base Change | COSMIC ID |
|---|---|---|---|---|
| EGFR n = 29 | NM_005228 SEQ ID NO.: 3 | L858R | 2573T>G | 6224 |
| | | T790M | 2369C>T | 6240 |
| | | L861Q | 2582T>A | 6213 |
| | | S768I | 2303G>T | 6241 |
| | | G719A | 2156G>C | 6239 |
| | | G719S | 2155G>A | 6252 |
| | | G719C | 2155G>T | 6253 |
| | | V769_D770insASV | 2307_2308ins9 | 12376 |
| | | H773_V774insH | 2319_2320insCAC | 12377 |
| | | D770_N771insG | 2310_2311insGGT | 12378 |
| | | E746_A750del | 2235_2249del15 | 6223 |
| | | E746_T751>I | 2235_2252>AAT (complex) | 13551 |
| | | E746_T751del | 2236_2253del18 | 12728 |
| | | E746_T751>A | 2237_2251del15 | 12678 |
| | | E746_S752>A | 2237_2254del18 | 12367 |
| | | E746_S752>V | 2237_2255>T (complex) | 12384 |
| | | E746_A750del | 2236_2250del15 | 6225 |
| | | E746_S752>D | 2238_2255del18 | 6220 |
| | | L747_A750>P | 2238_2248>GC (complex) | 12422 |
| | | L747_T751>Q | 2238_2252>GCA (complex) | 12419 |
| | | L747_E749del | 2239_2247del9 | 6218 |
| | | L747_T751del | 2239_2253del15 | 6254 |
| | | L747_S752del | 2239_2256del18 | 6255 |
| | | L747_A750>P | 2239_2248TTAAGAGAAG>C (complex) | 12382 |
| | | L747_P753>Q | 2239_2258>CA (complex) | 12387 |
| | | L747_T751>S | 2240_2251del12 | 6210 |
| | | L747_P753>S | 2240_2257del18 | 12370 |
| | | L747_T751del | 2240_2254del15 | 12369 |
| | | L747_T751>P | 2239_2251>C (complex) | 12383 |
| PIK3CA n = 16 | NM_006218.1 SEQ ID NO.: 4 | R88Q | 263G>A | 746 |
| | | E542K | 1624 G>A | 760 |
| | | E542Q | 1624G>C | 17442 |
| | | E545D | 1635 G>T | 765 |
| | | E545K | 1633 G>A | 763 |
| | | E545Q | 1633G>C | 27133 |
| | | Q546E | 1636C>G | 6147 |
| | | Q546K | 1636C>A | 766 |
| | | Q546L | 1637A>T | 25041 |
| | | Q546P | 1637A>C | 767 |
| | | Q546R | 1637A>G | 12459 |
| | | H1047L | 3140A>T | 776 |
| | | H1047Y | 3139C>T | 774 |
| | | H1047R | 3140 A>G | 775 |
| | | G1049R | 3145G>C | 12597 |
| | | G1049S | 3145G>A | 777 |
| ALK n = 10 | NM_004304 SEQ ID NO.: 5 | T1151_L1152insT | 3453_3454insACG | 144252 |
| | | L1152R | 3455T>G | 97185 |
| | | C1156Y | 3467G>A | 99136 |
| | | F1174L | 3522C>A | 28055 |
| | | F1174L | 3520T>C | 28057 |
| | | F1174L | 3522C>G | 28061 |
| | | L1196M | 3586C>A | 99137 |
| | | G1202R | 3604G>A | 144250 |
| | | S1206Y | 3617C>A | 144251 |
| | | G1269A | 3806G>C | n/a |
| APC n = 13 | NM_000038 SEQ ID NO.: 6 | R1114X | 3340C>T | 13125 |
| | | E1306X | 3916G>T | 18760 |
| | | E1309X | 3925G>T | 18775 |
| | | G1312X | 3934G>T | 18817 |
| | | E1322X | 3964G>T | 18702 |
| | | Q1338X | 4012C>T | 13129 |
| | | Q1378X | 4132C>T | 18862 |
| | | Q1429X | 4285C>T | 18836 |
| | | R1450X | 4348C>T | 13127 |
| | | T1556fs*3 | 4660_4661insA | 19695 |
| | | T1556fs*3 | 4662_4663insA | 18734 |
| | | T1556fs*3 | 4665_4666insA | 19020 |
| | | T1556fs*3 | 4666_4667insA | 18561 |

TABLE 1-continued

Exemplary Mutations for Cancer Analysis Panel.

| Gene | Accession Number | Mutation | Base Change | COSMIC ID |
|---|---|---|---|---|
| CTNNB n = 26 | NM_001904 SEQ ID NO.: 7 | D32A | 95A>C | 5690 |
| | | D32G | 95A>G | 5681 |
| | | D32H | 94G>C | 5668 |
| | | D32N | 94G>A | 5672 |
| | | D32V | 95A>T | 5691 |
| | | D32Y | 94G>T | 5661 |
| | | S33C | 98C>G | 5677 |
| | | S33F | 98C>T | 5669 |
| | | S33Y | 98C>A | 5673 |
| | | G34E | 101G>A | 5671 |
| | | G34V | 101G>T | 5670 |
| | | S37A | 109T>G | 5675 |
| | | S37C | 110C>G | 5679 |
| | | S37F | 110C>T | 5662 |
| | | S37P | 109T>C | 5687 |
| | | S37Y | 110C>A | 5666 |
| | | T41A | 121A>G | 5664 |
| | | T41I | 122C>T | 5676 |
| | | T41P | 121A>C | 5688 |
| | | T41S | 122C>G | 5701 |
| | | T41S | 121A>T | 5716 |
| | | S45A | 133T>G | 5685 |
| | | S45C | 134C>G | 5689 |
| | | S45F | 134C>T | 5667 |
| | | S45P | 133T>C | 5663 |
| | | S45Y | 134C>A | 5692 |
| IDH1 n = 5 | NM_005896.2 SEQ ID NO.: 8 | R132H | 395G>A | 28746 |
| | | R132C | 394C>T | 28747 |
| | | R132L | 395G>T | 28750 |
| | | R132S | 394C>A | 28748 |
| | | R132G | 394C>G | 28749 |
| IDH2 n = 7 | NM_002168.2 SEQ ID NO.: 9 | R172G | 514A>G | 33731 |
| | | R172M | 515G>T | 33732 |
| | | R172K | 515G>A | 33733 |
| | | R172S | 516G>T | 34090 |
| | | R140Q | 419G>A | 41590 |
| | | R140L | 419G>T | 41875 |
| | | R140W | 418C>T | 41877 |
| NRAS n = 19 | NM_002524 SEQ ID NO.: 10 | G12A | 35G>C | 565 |
| | | G12C | 34G>T | 562 |
| | | G12D | 35G>A | 564 |
| | | G12R | 34G>C | 561 |
| | | G12S | 34G>A | 563 |
| | | G12V | 35G>T | 566 |
| | | G13A | 38G>C | 575 |
| | | G13C | 37G>T | 570 |
| | | G13D | 38G>A | 573 |
| | | G13R | 37G>C | 569 |
| | | G13S | 37G>A | 571 |
| | | G13V | 38G>T | 574 |
| | | Q61E | 181C>G | 581 |
| | | Q61H | 183A>T | 585 |
| | | Q61H | 183A>C | 586 |
| | | Q61K | 181C>A | 580 |
| | | Q61L | 182A>T | 583 |
| | | Q61P | 182A>C | 582 |
| | | Q61R | 182A>G | 584 |
| PTEN n = 8 | NM_000314.4 SEQ ID NO.: 11 | R130X | 388C>T | 5152 |
| | | R130G | 388C>G | 5219 |
| | | R130Q | 389G>A | 5033 |
| | | R173C | 517C>T | 5089 |
| | | R233X | 697C>T | 5154 |
| | | R335X | 1003C>T | 5151 |
| | | K267fs*9 | 800delA | 5809 |
| | | K267fs*9 | 799delA | 5862 |

TABLE 1-continued

Exemplary Mutations for Cancer Analysis Panel.

| Gene | Accession Number | Mutation | Base Change | COSMIC ID |
|---|---|---|---|---|
| TP53 n = 26 | NM_000546 SEQ ID NO.: 12 | C141Y | 422G>A | 43708 |
| | | P151S | 451C>T | 10905 |
| | | P152L | 455C>T | 10790 |
| | | R158H | 473G>A | 10690 |
| | | Y163C | 488A>G | 10808 |
| | | R175H | 524G>A | 10648 |
| | | R175L | 524G>T | 10718 |
| | | H179R | 536A>G | 10889 |
| | | R213X | 637C>T | 10654 |
| | | Y220C | 659A>G | 10758 |
| | | G245C | 733G>T | 11081 |
| | | G245R | 733G>C | 10957 |
| | | G245S | 733G>A | 6932 |
| | | G245D | 734G>A | 43606 |
| | | G245V | 734G>T | 11196 |
| | | R248G | 742C>G | 11564 |
| | | R248L | 743G>T | 6549 |
| | | R248P | 743G>C | 11491 |
| | | R248Q | 743G>A | 10662 |
| | | R248W | 742C>T | 10656 |
| | | R249S | 747G>T | 10817 |
| | | R273C | 817C>T | 10659 |
| | | R273H | 818G>A | 10660 |
| | | R273L | 818G>T | 10779 |
| | | R273P | 818G>C | 43896 |
| | | R306X | 916C>T | 10663 |
| PDGFR n = 3 | NM_006206 SEQ ID NO.: 13 | D842V | 2525A>T | 736 |
| | | D842_H845del | 2524_2535del12 | 737 |
| | | S566_E571>R | 1698_1712del15 | 12418 |
| AKT1 n = 1 | ENST000003493 SEQ ID NO.: 14 | E17K | 49G>A | 33765 |
| HRAS n = 9 | NM_005343 SEQ ID NO.: 15 | G12C | 34G>T | 481 |
| | | G12D | 35G>A | 484 |
| | | G12S | 34G>A | 480 |
| | | G12V | 35G>T | 483 |
| | | G13R | 37G>C | 486 |
| | | G13V | 38G>T | 489 |
| | | Q61L | 182A>T | 498 |
| | | Q61K | 181C>A | 496 |
| | | Q61R | 182A>G | 499 |
| GNAQ n = 3 | NM_002072.2 SEQ ID NO.: 16 | Q209P | 626A>C | 28758 |
| | | Q209L | 626A>T | 28757 |
| | | Q209R | 626A>G | 28760 |
| GNA11 n = 2 | NM_002067.1 SEQ ID NO.: 17 | Q209P | 626A>C | 52970 |
| | | Q209L | 626A>T | 52969 |
| KIT n = 12 | NM_000222 SEQ ID NO.: 18 | D816V | 2447A>T | 1314 |
| | | D816H | 2446G>C | 1311 |
| | | D816Y | 2446G>T | 1310 |
| | | D820Y | 2458G>T | 12710 |
| | | K642E | 1924A>G | 1304 |
| | | L576P | 1727T>C | 1290 |
| | | V559A | 1676T>C | 1255 |
| | | V559D | 1676T>A | 1252 |
| | | V559G | 1676T>G | 1253 |
| | | W557R | 1669T>A | 1216 |
| | | W557R | 1669T>C | 1219 |
| | | W557G | 1669T>G | 1221 |
| ABL1 n = 11 | X16416 SEQ ID NO.: 19 | M244V | 730A>G | 12608 |
| | | G250E | 749G>A | 12577 |
| | | Q252H | 756G>C | 12609 |
| | | Y253H | 757T>C | 12576 |
| | | E255K | 763G>A | 12573 |
| | | E255V | 764A>T | 12574 |
| | | T315I | 944C>T | 12560 |
| | | F317L | 951C>G | 12575 |
| | | M351T | 1052T>C | 12578 |
| | | F359V | 1075T>G | 12605 |
| | | H396R | 1187A>G | 12604 |

TABLE 1-continued

Exemplary Mutations for Cancer Analysis Panel.

| Gene | Accession Number | Mutation | Base Change | COSMIC ID |
|---|---|---|---|---|
| MEK1 | NM_002755 | Q56P | 167A>C | n/a |
| n = 6 | SEQ ID NO.: 20 | K57N | 171G>T | n/a |
| | | D67N | 199G>A | n/a |
| | | P124S | 370C>T | n/a |
| | | C121S | 362G>C | n/a |
| | | I111S | 332T>G | n/a |

TABLE 2

Exemplary Cancer Detection Panel.

| Gene | Mutation | Base Change |
|---|---|---|
| BRAF | V600E | 1799T>A |
| n = 4 | V600E | 1799_1800TG>AA |
| | V600D | 1799_1800TG>AT |
| | V600K | 1798_1799GT>AA |
| KRAS | G12A | GGT>GCT (35G>C) |
| n = 7 | G12D | GGT>GAT (35G>A) |
| | G12R | GGT>CGT (34G>C) |
| | G12C | GGT>TGT (34G>T) |
| | G12S | GGT>AGT (34G>A) |
| | G12V | GGT>GTT (35G>T) |
| | G13D | GGC>GAC (38G>A) |
| ALK | L1196M | 3586C>A |
| n = 8 | C1156Y | 3467G>A |
| | F1174L | 3522C>A |
| | L1152R | 3455T>G |
| | G1202R | 3604G>A |
| | S1206Y | 3617 C>A |
| | G1269A | 3806G>C |
| | T1151_11152insT | 3453_3454insACG |
| EGFR | L858R | 2573T>G |
| n = 29 | T790M | 2369C>T |
| | L861Q | 2582T>A |
| | S7681 | 2303G>T |
| | G719A | 2156G>C |
| | G719S | 2155G>A |
| | G719C | 2155G>T |
| | V769_D770insASV | 2307_2308ins9 |
| | H773_V774insH | 2319_2320insCAC |
| | D770_N771insG | 2310_2311insGGT |
| | E746_A750del | 2235_2249del15 |
| | E746_T751>I | 2235_2252>AAT |
| | E746_T751del | 2236_2253del18 |
| | E746_T751>A | 2237_2251del15 |
| | E746_S752>A | 2237_2254del18 |
| | E746_S752>V | 2237_2255>T |
| | E746_A750del | 2236_2250del15 |
| | E746_S752>D | 2238_2255del18 |
| | L747_A750>P | 2238_2248>GC |
| | L747_T751>Q | 2238_2252>GCA |
| | L747_E749del | 2239_2247del9 |
| | L747_T751del | 2239_2253del15 |
| | L747_S752del | 2239_2256del18 |
| | L747_A750>P | 2239_2248TTAAGAGAAG>C |
| | L747_P753>Q | 2239_2258>CA |
| | L747_T751>S | 2240_2251del12 |
| | L747_P753>S | 2240_2257del18 |
| | L747_T751del | 2240_2254del15 |
| | L747_T751>P | 2239_2251>C |
| PI3K | E542K | 1624 G>A |
| n = 4 | E545D | 1635 G>T |
| | E545K | 1633 G>A |
| | H1047R | 3140 A>G |

The invention claimed is:

1. A method of characterizing a biomarker in a sample, the method comprising:
providing a sample comprising a wild-type nucleic acid and a corresponding mutant nucleic acid that is a biomarker for a disease;
introducing a plurality of positive controls to the sample, the plurality of positive controls comprising a sequence identical to the mutant nucleic acid and a unique control sequence comprising a number of degenerate bases;
amplifying the mutant nucleic acid and the plurality of positive controls in the sample;
loading the amplified nucleic acid sample and the plurality of positive controls on a separation medium, the separation medium comprising an immobilized probe, the immobilized probe comprising a nucleic acid sequence complementary to the mutant nucleic acid;
enriching the amplified nucleic acid sample for the mutant nucleic acid and the plurality of positive controls over the wild type nucleic acid by applying a time-varying driving field and a time-varying mobility-varying field to the separation medium;
characterizing the enriched nucleic acid in the sample with a technique selected from nucleic acid sequencing, quantitative PCR (qPCR), mass spectrometry, and hybridization assay; and
quantifying abundance of the mutant nucleic acid in the provided sample using the plurality of positive controls.

2. The method of claim 1, wherein characterizing the enriched nucleic acid comprises determining a sequence of the nucleic acid, determining an amount of the enriched nucleic acid as compared to another nucleic acid, or determining an absolute number of nucleic acid molecules in the sample.

3. The method of claim 1, wherein nucleic acid sequencing is selected from Sanger sequencing, single molecule sequencing, nanopore-based sequencing, sequencing by synthesis, sequencing by ligation, pyrosequencing, sequencing by hydrogen ion release detection, ion semiconductor sequencing, and atomic force microscopy sequencing.

4. The method of claim 1, wherein the nucleic acid is between about 20 and 100 nucleotides in length.

5. The method of claim 1, wherein the sample is obtained from a tissue sample of a subject, a body fluid of a subject, a cell sample of a subject, or a stool sample of a subject.

6. The method of claim 5, wherein the body fluid is selected from blood, a portion of whole blood, saliva, tears, sweat, sputum, urine, and nipple aspirate.

7. The method of claim 6, wherein the portion of whole blood is blood plasma or cell-free nucleic acid.

8. The method of claim 5, wherein the tissue sample is a formalin-fixed paraffin-embedded (FFPE) tissue sample.

9. The method of claim 1, wherein amplifying comprises conducting between 1 and 10 cycles of PCR.

10. The method of claim 1, wherein the amplified nucleic acid is cleaned prior to enrichment.

11. The method of claim 10, wherein the amplified nucleic acid is cleaned using a commercial PCR clean-up column, by addition of an enzyme to specifically digest primers, by heat inactivation of enzymes remaining after amplification, or a combination thereof.

12. The method of claim 1, wherein amplifying additionally comprises producing amplicons comprising barcodes.

13. The method of claim 1, wherein applying a time-varying driving field and a time-varying mobility-varying field comprises applying two non-collinear time-dependent electric fields.

14. A method of characterizing a plurality of nucleic acids, comprising:

providing a sample comprising wild-type and mutant versions of a first nucleic acid and wild type and mutant versions of a second nucleic acid;

introducing a plurality of positive controls to the sample, each of the plurality of positive controls comprising a sequence identical to the mutant version of the first or second nucleic acid and a unique control sequence comprising a number of degenerate bases;

amplifying the mutant versions of the first and second nucleic acids and the plurality of controls in the sample;

loading the nucleic acid sample on a separation medium, the separation medium comprising:
- a first immobilized probe comprising a nucleic acid sequence complementary to the mutant version of the first nucleic acid; and
- a second immobilized probe comprising a nucleic acid sequence complementary to the mutant version of the second nucleic acid;

enriching the amplified nucleic acid sample for the mutant versions of the first and second nucleic acids and the plurality of positive controls by applying a time-varying driving field and a time-varying mobility-varying field to the separation medium;

characterizing the enriched first and second nucleic acids in the sample with a technique selected from nucleic acid sequencing, quantitative PCR (qPCR), mass spectrometry, and hybridization assay; and quantifying abundance of the mutant versions of the first and second nucleic acids present in the provided sample using the plurality of positive controls.

15. The method of claim 14, wherein the first and second nucleic acids comprise barcodes.

16. The method of claim 14, wherein the first and second nucleic acids are PCR amplified with primers including barcode sequences.

17. The method of claim 16, wherein the PCR is multiplexed.

18. The method of claim 14, wherein the first nucleic acid and the second nucleic acids are from different subjects.

19. The method of claim 14, wherein the first nucleic acid and the second nucleic acids are from the same subject.

20. The method of claim 1, wherein the mutant nucleic acid is present at a 0.01% to 0.1% abundance relative to the wild-type nucleic acid in the sample.

21. The method of claim 14, wherein at least one of the mutant versions of the first and second nucleic acids is present at a 0.01% to 0.1% abundance relative to the respective wild-type version.

* * * * *